United States Patent
Pordy et al.

(10) Patent No.: US 10,934,349 B2
(45) Date of Patent: Mar. 2, 2021

(54) METHODS FOR INCREASING LEAN BODY MASS WITH RESISTANCE TRAINING AND A GDF8 INHIBITOR THAT IS AN ANTI-GDF8 ANTIBODY

(71) Applicant: Regeneron Pharmaceuticals, Inc., Tarrytown, NY (US)

(72) Inventors: Robert C. Pordy, Ardsley, NY (US); Xiaobing Qian, Briarcliff Manor, NY (US); Stephen Donahue, Princeton, NJ (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 15/099,701

(22) Filed: Apr. 15, 2016

(65) Prior Publication Data

US 2016/0304595 A1  Oct. 20, 2016

Related U.S. Application Data

(60) Provisional application No. 62/147,853, filed on Apr. 15, 2015, provisional application No. 62/234,899, filed on Sep. 30, 2015, provisional application No. 62/261,528, filed on Dec. 1, 2015.

(51) Int. Cl.
| | |
|---|---|
| *A61K 39/395* | (2006.01) |
| *C07K 16/22* | (2006.01) |
| *C07K 14/47* | (2006.01) |
| *C07K 14/475* | (2006.01) |
| *A61K 39/00* | (2006.01) |

(52) U.S. Cl.
CPC .......... *C07K 16/22* (2013.01); *A61K 39/3955* (2013.01); *A61K 2039/505* (2013.01); *C07K 14/4703* (2013.01); *C07K 14/475* (2013.01); *C07K 14/4716* (2013.01); *C07K 2317/21* (2013.01); *C07K 2317/34* (2013.01); *C07K 2317/56* (2013.01); *C07K 2317/76* (2013.01)

(58) Field of Classification Search
CPC ... A61K 39/3955; C07K 16/22; C07K 14/475
See application file for complete search history.

(56) References Cited

U.S. PATENT DOCUMENTS

| | | | |
|---|---|---|---|
| 5,500,362 A | 3/1996 | Robinson et al. | |
| 5,821,337 A | 10/1998 | Carter et al. | |
| 6,096,506 A | 8/2000 | Lee et al. | |
| 6,368,597 B1 | 4/2002 | Strassmann et al. | |
| 6,468,535 B1 | 10/2002 | Lee et al. | |
| 6,858,208 B2 | 2/2005 | Lee et al. | |
| 7,070,784 B1 | 7/2006 | Halkier et al. | |
| 7,241,444 B2 | 7/2007 | Goetsch et al. | |
| 7,261,893 B2 | 8/2007 | Veldman et al. | |
| 7,320,789 B2 | 1/2008 | Aghajanian et al. | |
| 7,534,432 B2 | 5/2009 | Lee et al. | |
| 7,632,499 B2 | 12/2009 | Davies et al. | |
| 7,635,760 B2 | 12/2009 | Han et al. | |
| 7,655,763 B2 | 2/2010 | Veldman et al. | |
| 7,731,961 B1 | 6/2010 | Aghajanian et al. | |
| 7,745,583 B2 | 6/2010 | Han et al. | |
| 7,785,587 B2 | 8/2010 | Whittemore et al. | |
| 7,807,159 B2 | 10/2010 | Chin et al. | |
| 7,807,631 B2 | 10/2010 | Knopf et al. | |
| 7,888,486 B2 | 2/2011 | Walsh et al. | |
| 7,892,561 B2 | 2/2011 | Junker et al. | |
| 7,910,107 B2 | 3/2011 | Walsh et al. | |
| 8,309,082 B2 | 11/2012 | Han et al. | |
| 8,415,459 B2 | 4/2013 | LaVallie et al. | |
| 8,496,934 B2 | 7/2013 | Walsh et al. | |
| 8,586,713 B2 | 11/2013 | Davis et al. | |
| 8,840,894 B2 | 9/2014 | Stitt et al. | |
| 8,871,209 B2 | 10/2014 | Stitt et al. | |
| 8,940,874 B2 | 1/2015 | Veldman et al. | |
| 8,992,913 B2 | 3/2015 | Mader et al. | |
| 8,999,343 B2 | 4/2015 | Han et al. | |
| 9,260,515 B2 | 2/2016 | Stitt et al. | |
| 2004/0142382 A1 | 7/2004 | Veldman et al. | |
| 2005/0175612 A1 | 8/2005 | Lee et al. | |
| 2006/0034831 A1 | 2/2006 | Tobin | |
| 2007/0178095 A1 | 8/2007 | Smith et al. | |
| 2007/0280945 A1 | 12/2007 | Stevens et al. | |
| 2008/0187543 A1 | 8/2008 | Kambadur et al. | |

(Continued)

FOREIGN PATENT DOCUMENTS

| | | |
|---|---|---|
| EP | 1773041 | 4/2007 |
| EP | 2594280 | 5/2013 |

(Continued)

OTHER PUBLICATIONS

Record for Clinical Trial NCT01910220, version dated Feb. 2, 2014, available at https://clinicaltrial.gov/archive/NCT01910220/2014_02_12, 3 pages as printed, no author listed.*
Willis et al, 2012. J Appl Physiol. 113(12): 1831-1837.*
Rudikoff et al (Proc Natl Acad Sci USA 1982 vol. 79 pp. 1979-1983).*
MacCallum et al. (Journal of Molecular. Biology, 1996, vol. 262, pp. 732-745).*
Pascalis et al (Journal of Immunology, 2002, vol. 169, pp. 3076-3084).*
Casset et al (Biochemical and Biophysical Research Communications, 2003, vol. 307, pp. 198-205).*
Vajdos et al (Journal of Molecular biology, 2002, vol. 320, pp. 415-428).*
Holm et al (Molecular Immunology, 2007, vol. 44, pp. 1075-1084).*

(Continued)

*Primary Examiner* — Zachary C Howard
(74) *Attorney, Agent, or Firm* — Merchant & Gould, P.C.

(57) ABSTRACT

The disclosure provides compositions, kits, and methods of using a GDF-8 inhibitor to increase lean muscle mass. In embodiments, a GDF-8 inhibitor is an antibody or antigen binding fragment thereof that specifically binds GDF-8. In embodiments, a method comprises providing an exercise regimen for the subject, and administering a composition comprising an effective amount of a GDF-8 inhibitor.

29 Claims, 7 Drawing Sheets

Specification includes a Sequence Listing.

(56) References Cited

U.S. PATENT DOCUMENTS

| | | |
|---|---|---|
| 2008/0299126 A1 | 12/2008 | Han et al. |
| 2009/0136481 A1 | 5/2009 | Kambadur et al. |
| 2009/0148436 A1 | 6/2009 | Lavallie et al. |
| 2009/0227497 A1 | 9/2009 | Sun et al. |
| 2009/0311252 A1 | 12/2009 | Knopf et al. |
| 2010/0080811 A1 | 4/2010 | Davies et al. |
| 2010/0166764 A1 | 7/2010 | Sayers et al. |
| 2010/0272734 A1 | 10/2010 | Berger et al. |
| 2010/0322942 A1 | 12/2010 | Whittemore et al. |
| 2011/0008375 A1 | 1/2011 | Hq et al. |
| 2011/0020330 A1 | 1/2011 | Aghajanian et al. |
| 2011/0256132 A1 | 10/2011 | Ashman et al. |
| 2011/0293630 A1 | 12/2011 | Stitt et al. |
| 2012/0015877 A1 | 1/2012 | Seehra et al. |
| 2012/0237521 A1 | 9/2012 | Berger et al. |
| 2013/0142788 A1 | 6/2013 | Ashman et al. |
| 2013/0209489 A1 | 8/2013 | Han et al. |
| 2013/0336982 A1 | 12/2013 | Mader et al. |
| 2015/0037339 A1 | 2/2015 | Gromada et al. |
| 2016/0340421 A1 | 11/2016 | Stitt et al. |
| 2017/0226197 A1 | 8/2017 | Stitt et al. |

FOREIGN PATENT DOCUMENTS

| | | | |
|---|---|---|---|
| JP | 2012-512641 A | 6/2012 | |
| JP | 2013-528608 A | 7/2013 | |
| JP | 2014-534239 A | 12/2014 | |
| WO | 2004/037861 | 5/2004 | |
| WO | 2005/094446 A2 | 10/2005 | |
| WO | 2005/103081 A2 | 11/2005 | |
| WO | 2006/116269 A2 | 11/2006 | |
| WO | 2007/044411 A2 | 4/2007 | |
| WO | 2007/047112 | 4/2007 | |
| WO | 2008/031061 A2 | 3/2008 | |
| WO | 2009/058346 A1 | 5/2009 | |
| WO | 2009/059943 A1 | 5/2009 | |
| WO | 2010/070094 | 6/2010 | |
| WO | 2011/063018 A1 | 5/2011 | |
| WO | 2011/150008 | 12/2011 | |
| WO | 2012/064771 | 5/2012 | |
| WO | 2013/074557 A1 | 5/2013 | |
| WO | 2013/186719 A1 | 12/2013 | |
| WO | WO 2015022658 A2 * | 2/2015 | ......... C07K 16/2863 |
| WO | 2016/168613 | 10/2016 | |

OTHER PUBLICATIONS

Chen et al. (Journal of Molecular Biology, 1999, vol. 293, pp. 865-881.*

Wu et al. (Journal of Molecular Biology, 1999, vol. 294, pp. 151-162).*

Mosier et al (2014. Physiol Rep 2(3): 1-13; published on-line Mar. 20, 2014).*

Lowe et al (2002. J Orthop Sports Phys Ther. 32: 36-43).*

Siparsky et al (Jan. 2014. Sports Health. 6(1):36-40).*

International Search Report and Written Opinion dated Jun. 30, 2016 in corresponding PCT/US2016/027774, 22 pages total.

Wagner et al., "A phase I/II trial of MYO-29 in adult subjects with muscular dystrophy," Annals of Neurology, vol. 63, No. 5, May 1, 2008, pp. 561-571.

LeBrasseur et al., "Myostatin inhibition enhances the effects of exercise on performance and metabolic outcomes in aged mice," Journals of Gerontology, Series A, Biological Sciences and Medical Sciences, vol. 64A, No. 9, Sep. 1, 2009, pp. 940-948.

Padhi et al., Pharmacological inhibition of myostatin and changes in lean body mass and lower extremity muscle size in patients receiving androgen deprivation therapy for prostate cancer, Journal of Clinical Endocrinology and Metabolism, vol. 99, No. 10, Oct. 1, 2014, pp. E1967-E1975.

Sharp et al., "The effects of a myostatin inhibitor on lean body mass, strength, and power in resistance trained males," Journal of the International Society of Sports Nutrition, vol. 11, No. Suppl 1, Dec. 1, 2014, p. P42.

Smith et al., "Myostatin inhibitors as therapies for muscle wasting associated with cancer and other disorders," Current Opinion in Supportive and Palliative Care, vol. 7, No. 4, Dec. 2013, p. 352-360.

Allen et al., "Expression and function of myostatin in obesity, diabetes, and exercise adaptation," Medicine and Science in Sports and Exercise, vol. 43, No. 10, Oct. 1, 2011, pp. 1828-1835.

Abbott et al., "Current approaches to fine mapping of antigen-antibody interactions," Immunology.; 142(4):526-535 (Aug. 2014).

Al-Lazikani et al., "Standard Conformations for the Canonical Structures of Immunoglobulins"; J Mol Biol; 273(4):927-948 (1997).

Altschul et al., "Basic local alignment search tool"; J Mol Biol; 215(3):403-410 (1990).

Altschul et al., "Gapped BLAST and PSI-BLAST: a new generation of protein database search programs"; Nucleic Acids Res; 25(17):3389-33402 (1997).

Angal et al., "A single amino acid substitution abolishes the heterogeneity of chimeric mouse/human (IgG4) antibody"; Molecular Immunology; 30(1):105-108 (Jan. 1993).

Boder et al., "Directed evolution of antibody fragments with monovalent femtomolar antigen-binding affinity," Proc Natl Acad SCi USA.; 97(20):10701-10705 (Sep. 26, 2000).

Brown et al., "Tolerance of single, but Not Multiple, Amino Acid Replacements in Antibody $V_H$ CDR2: A Means of Minimizing B Cell Wastage from Somatic Hypermutation?"; The J of Immunology; 156(9):3285-3291. (May 1, 1996).

Cadena et al., "Administration of a soluble activin type IIb receptor promotes muscle growth independent of fiber type," Journal of Applied Physiology, vol. 109, pp. 635-642 (2010).

Canziani et al., "Characterization of neutralizing affinity-matured human respiratory syncytial virus F binding antibodies in the sub-picomolar affinity range"; J of Molecular Recognition; 25(3):136-146 (Mar. 28, 2012).

Chilean Substantive Report issued on Oct. 10, 2014, in corresponding Chilean Patent Application 3283-2012.

Clynes et al., "Fc receptors are required in passive and active immunity to melanoma"; Immunology, Proc. Nat'l. Acad. Sci. USA; 95:652-656 (Jan. 1998).

Cochrane et al., "Renal Structural and Functional Repair in a Mouse Model of Reversal of Ureteral Obstruction"; J Am Soc Nephrol; 16(12):3623-3630 (Dec. 1, 2005).

Colombian Office Action dated Aug. 19, 2014 for related Colombian patent application 12233131.

Cook et al., Structural basis for a functional antagonist in the transforming growth factor beta superfamily. J Biol Chem.; 280(48): 40177-40186. (Epub Sep. 26, 2005) (Dec. 2, 2005).

Davies et al., "Affinity improvement of single antibody VH domains: residues in all three hypervariable regions affect antigen binding" Immunotechnology, 2(3):169-179 (Sep. 1996).

Dufner et al., "Harnessing phage and ribosome display for antibody optimisation"; Trends in Biotechnology; 24(11):523-529 (Nov. 1, 2006).

Ehring, "Hydrogen Exchange/electrospray Ionizatino Mass Spectrometry Sudies of Structural Features of Proteins and Protein/Protein Interactions"; Analytical Biochemistry; 267(2):252-259 (Feb. 15, 1999).

Engen et al., "Investigating protein structure and dynamics by hydrogen exchange MS"; Anal. Chem.; 73(9):256A-265A (May 1, 2001).

Giusti et al., "Somatic diversification of S107 from an antiphosphocholine to an anti-DNA autoantibody is due to a single base change in its heavy chain variable region"; PNAS, USA, 84(9):2926-2930 (May 1987).

Gonnet et al., "Exhaustive Matching of the Entire Protein Sequence Database"; Science; 256(5062):1443-1445 (Jun. 5, 1992).

Goodson, "Dental applications"; Medical Applications of Controlled Release; 2:115-138 (1984).

Hanes et al., "Picomolar Affinity Antibodies from a Fully Synthetic Naïve Library Selected and Evolved by Ribosome Display"; Nature Biotechnology; 18(12):1287-1292 (Dec. 2000).

He et al., "Activin A inhibits formation of skeletal muscle during chick development"; Anat. Embryol (Berl); 209(5):401-407 (Jun. 2005).

(56) References Cited

OTHER PUBLICATIONS

Holt et al., "Domain antibodies: proteins for therapy"; Trends in Biotechnology; 21(11):484-490 (Nov. 2003).
Hoogenboom, "Selecting and screening recombinant antibody libraries"; Nature Biotechnology; 23(9):1105-1116 (Sep. 1, 2005).
International Search Report dated Sep. 21, 2011, in corresponding PCT/US2011/037837.
International Search Report dated May 23, 2013, in corresponding PCT/US2012/064911.
International Search Report dated Jan. 8, 2015, in PCT/US2014/048957.
Junghans et al., "Anti-Tac-H, a Humanized Antibody to the Interleukin 2 Receptor with New Features for Immunotherapy in Malignant and Immune Disorders"; Cancer Res.; 50:1495-1502 (Mar. 1, 1990).
Kabat, "Sequences of Proteins of Immunological Interest"; National Institutes of Health (U.S.); 6 pages (1991).
Kazane et al., "Self-Assembled Antibody Multimers through Peptide Nucleic Acid Conjugation"; J Am Chem Soc.; 135(1):340-346 (Jan. 9, 2013).
Khurana et al., "Pharmacological Strategies for Muscular Dystrophy"; Nature Reviews/Druq Discovery; 2.379-390 (2003).
Klein et al., "Progress in overcoming the chain association issuein bispecific heterodimeric IgG antibodies"; mAbs 4(6):653-663 (Nov./Dec. 2012).
Kufer et al.; "A revival of bispecific antibodies"; Trends Biotechnol; 22(5):238-244 (May 2004).
Kussie et al., "A Single Engineered Amino Acid Substitution Changes Antibody Fine Specificity"; J of Immunology; 152:146-152 (1994).
Langer, "New Methods of Drug Delivery"; Science; 249:1527-1533 (Sep. 23, 1990).
Lee et al., "Regulation of muscle growth by multiple ligands signaling through Activin type II receptors"; PNAS USA; 102(50):18117-18122 (Dec. 13, 2005) (Epub Dec. 5, 2005).
Lee et al., "Regulation of GDF-11 and myostatin activity by GASP-1 and GASP-2"; PNAS USA.; 110(3):E3713-E3722 (Sep. 9, 2013).
Lin et al., "The structural basis of TGF-beta, bone morphogenetic protein, and activing ligand binding." Reproduction 132(2): 179-190 (Aug. 2006).
Liu et al., "Fine mapping of the antigen-antibody interaction of scFv215, a recombinant antibody inhibiting RNA polymerase II from *Drosophila melanogaster*"; J of Molecular Recognition; 12(2):103-111 (1999).
MacCallum et al., "Antibody-Antigen Interactions: Contact Analysis and Binding Site Topography"; J. Mol. Biol.; 262(5):732-745 (Oct. 11, 1996).
Martin et al., "Modeling antibody bypervariable loops: A combined algorithm"; PNAS USA; 86(23):9268-9272 (Dec. 1989).
Maynard et al., "Antibody Engineering"; Annu. Rev. Biomed. Eng.; 02:339-376 (2000).
McPherron et al., "Regulation of skeletal muscle mass in mice by a new TGF-p superfamily member"; Nature; 387(6628):83-90 (May 1997).
McPherron et al., "Redundancy of myostatin and growth/differentiation factor 11 function"; BMC Dev Biol; 9:24 (9 pgs) (Mar. 19, 2009).
Mordenti et al., "Interspecies Scaling of Clearance and Volume of Distribution Data for Five Therapeutic Proteins"; Pharm Res; 8(11):1351-1359 (Nov. 1991).
Munoz et al., "Biologicals Targeting Myostatin/GDF-11/Activins Prevent Burn-Induced Muscle Loss in Mice"; Journal of Surgical Research; 186(2)(abstract 34.6):591-592 (Feb. 2014).
Orcutt et al., "Engineering an antibody with picomolar affinity to DOTA chelates of multiple radionuclides for pretargeted radioimmunotherapy and imaging"; Nuclear Medicin and Biology; 38(2):223-233 (Aug. 31, 2010).
Pearson, "Using the FASTA program to search protein and DNA sequence databases"; Methods Mol Biol,; 24(Ch 26): 307-331 (1994).

Pearson, "Flexible sequence similarity searching with the FASTA3 program package", Methods Mol Biol 132: 185-219 (2000).
Pini et al., "Design and Use of a Phage Display Library: Human Antibodies with Subnanomolar Affinity Against a Marker of Angiogenesis Eluted from a Two-Dimentional Gel", The Journal of Biological Chemistry, 273(34):21769-21776 (Aug. 21, 1998).
Powell et al., "Compendium of Excipients for Parenteral Formulations"; J of Pharm Science & Technology; 52(5):238-311 (Sep.-Oct. 1998).
Rajpal et al., "A general method for greatly improving the affinity of antibodies by using combinatorial libraries"; Proceedings of the Nat'l Academy of Sciences US; 102(24)8466-8471 (Jun. 14, 2005).
Reddy et al., "Elimination of Fc Receptor-Dependent Effector Functions of a Modified IgG4 Monoclonal Antibody to Human CD4"; J Immunol; 164:1925-1933 (2000).
Reineke, "Antibody epitope mapping using arrays of synthetic peptides"; Methods Mol Biol; 248(26):443-463 (2004).
Rudikoff et al., "Single amino acid substitution altering antigen-binding specificity". PNAS, USA, 79:1979-1983, (Mar. 1982).
Schildbach et al., Heavy Chain Position 50 Is a Determinant of Affinity and Specificity for the Anti-digoxin Antibody 26-10. The Journal of Biological Chemistry, 268(29):21739-21747 (Oct. 15, 1993).
Schildbach et al., "Contribution of a single heavy chain residue to specificity of an anti-digoxin monoclonal antibody", Protein Science, 3(5):737-749 (1994).
Sefton, "Implantable Pumps"; CRC Crit. Ref. Biomed. Eng. 14:201-240 (1987).
Shields et al., "Lack of fucose on human IgG1 N-linked oligosaccharide improves binding to human Fcgamma RIII and antibody-dependent cellular toxicity"; J Biol Chem; 277(30):26733-26740 (Jul. 26, 2002).
Souza et al., "Proteomic identification and functional validation of activins and bone morphogenetic protein 11 as candidate novel muscle mass regulators"; Mol Endocrinol; 22(12):2689-2702 (Dec. 2008).
Sozzani et al., "The yin and yang of Activin A"; Blood; 117(19):5013-5015 (May 12, 2011).
Sutcliffe et al., "Antibodies that React with Predetermined Sites on Proteins"; Science; 219:660-666(Feb. 11, 1983).
Taylor et al., "A Transgenic Mouse that Expresses a Diversity of Human Sequence Heavy and Light Chain Immunoglobulins"; Nucleic Acids Research; 20{23}:6287-6295 (1992).
Thompson et al., "Structures of an ActRIIB:activin A complex reveal a novel binding mode for TGF-beta ligand: receptor interactions." EMBO J.; 22(7): 1555-1566 (Apr. 1, 2003).
Tomer, Hochleitner et al., "Characterization of a discontinuous epitope of the human immunodeficiency virus (HIV) core protein p24 by epitope excision and differential chemical modification followed by mass spectrometric peptide mapping analysis"; Protein Science; 9:487-496 (2000).
Tornetta et al., "Antibody Fab display and selection through fusion to the pIX coat protein of filamentous phage"; J. Immunological Methods; 360(1-2):39-46 (Aug. 31, 2010).
Tsuchida et al., "Activin signaling as an emerging target for therapeutic interventions"; Cell Commun Signal; 7:15 (Jun. 18, 2009).
Tutt et al., "Trispecific F(ab')3 derivatives that use cooperative signaling via the TCR/CD3 complex and CD2 to activiate and redirect resting cytotoxic T cells"; J Immunol; 147(1):60-69 (1991).
Vajdos et al., "Comprehensive Functional Maps of the Antigen-Binding Site of an Anti-ErbB2 Antibody Obtained with Shotgun Scanning Mutagenesis"; J. Mol. Biol. 320{2}:415-428 (Jul. 2002).
Wark et al., "Latest technologies for the enhancement of antibody affinity"; Advanced Drug Delivery Reviews; 58(5-6):657-670 (Aug. 7, 2006).
Whittemore et al., "Inhibition of myostatin in adult mice increases skeletal muscle mass and strength"; Biochem, Biophys. Res. Commun 300:965-971 (2003).
Wu et al., "Receptor-Mediated in Vitro Gene Transformation by a Soluble DNA Carrier System"; Journal of Biological Chemistry; 262(10):4429-4432 (1987).

(56) References Cited

OTHER PUBLICATIONS

Wu et al., "Humanization of a Murine Monoclonal Antibody by Simultaneous Optimization of Framework and CDR Residues", J. Mol. Biol.; 294(1): 151-162 (Nov. 19, 1999).

Xia et al., "The biology of activing: recent advances in structure, regulation, and function," J Endocrinol.; 202(1):1-12. (Jul. 2009) (Epub Mar. 9, 2009).

Xiang et al., "Study of B72.3 combining sites by molecular modeling and site-directed mutagenesis", Protein Eng. 13(5):339-344 (May 2000).

Bogdanovich et al., "Myostatin blockade improves function but not histopathology in a murine model of limb-girdle muscular dystrophy 2C," Muscle Nerve, Mar. 2008, vol. 37, pp. 308-316.

Holzbaur et al., "Myostatin inhibition slows muscle atrophy in rodent models of amyotrophic lateral sclerosis," Nuerobiology of Disease, 2006, vol. 23, pp. 697-707.

Lee et al., "Extracellular regulation of myostatin: a molecular rheostat for muscle mass," Immunol Endocr Metab Agents Med Chem, 2010, vol. 10, pp. 183-194.

McPherron, "Metabolic functions of myostatin and GDF11," Immunol Endocr Metab Agents Med Chem, Dec. 2010, 10(4):217-231.

Musculoskeletal Diseases, in MESH Database, National Center for Biotechnology Information, Bethesda, Maryland, USA [online], [retrieved on Jan. 9, 2017]. Retrieved from the Internet: <URL: https://www.ncbi.nlm.nih.gov/mesh/?term=musculoskeletal+diseases> 4 pages total.

Singapore Search Report and Written Opinion dated Mar. 1, 2017 in corresponding application SG 11201600731W, 11 pages total.

Zhou et al., "Reversal of cancer cachexia and muscle wasting by ActRIIB antagonism leads to prolonged survival," Cell, Aug. 20, 2010, vol. 142, pp. 531-543.

Saremi A. et al., "Twelve-week resistance training decreases myostatin level and improves insulin sensitivity in overweight-obese woman", Int. J. Diabetes & Metab. vol. 19: 63-68 (2011).

Saremi A et al., "Effects of oral creatine and resistance training on serum myostatin and GASP-1", Molecular and Cellular Endocrinology, vol. 317: 25-30 (2010).

Gould D.W. et al., "Cancer cachexia prevention via physica exercise: molecular mechanisms", Jounal of Cachexia, Sarcopenia and Muscle, vol. 4(2): 111-124 (2013).

Communication pursuant to Article 94(3) EPC for European Patent Application No. 16718831.7 (May 7, 2020).

Office Action for Japanese Patent Application No. 2017-553974 (dated Mar. 31, 2020).

Kim et. al. "Impact of resistance loading on myostatin expression and cell cycle regulation in young and older men and women", Am Physiol Endocrinol Metab 288: E1110-1119, 2005.

Office Action dated Nov. 18, 2020 in Eurasian Patent Application No. 201792298 and English translation thereof, 5 pages total.

* cited by examiner

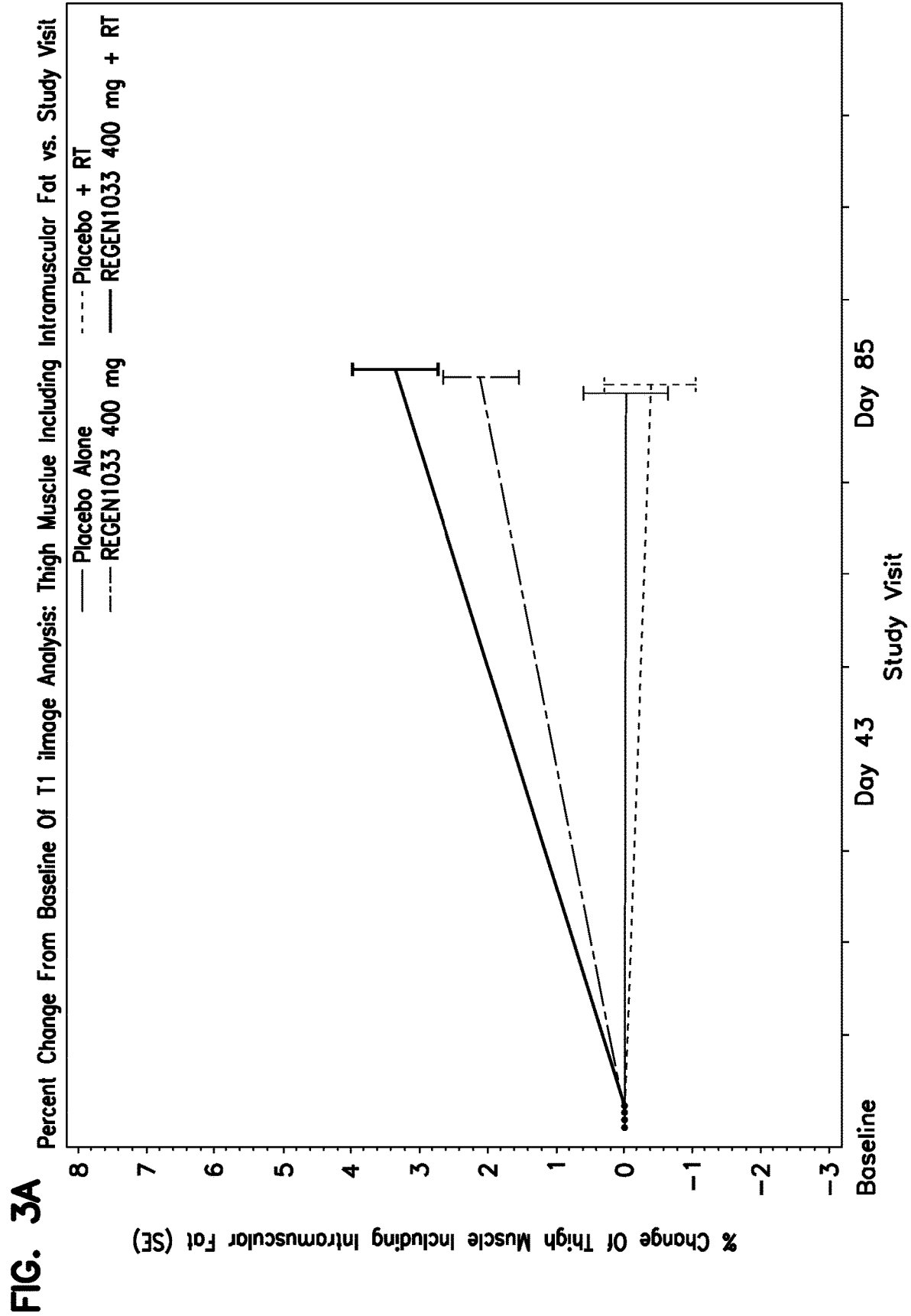

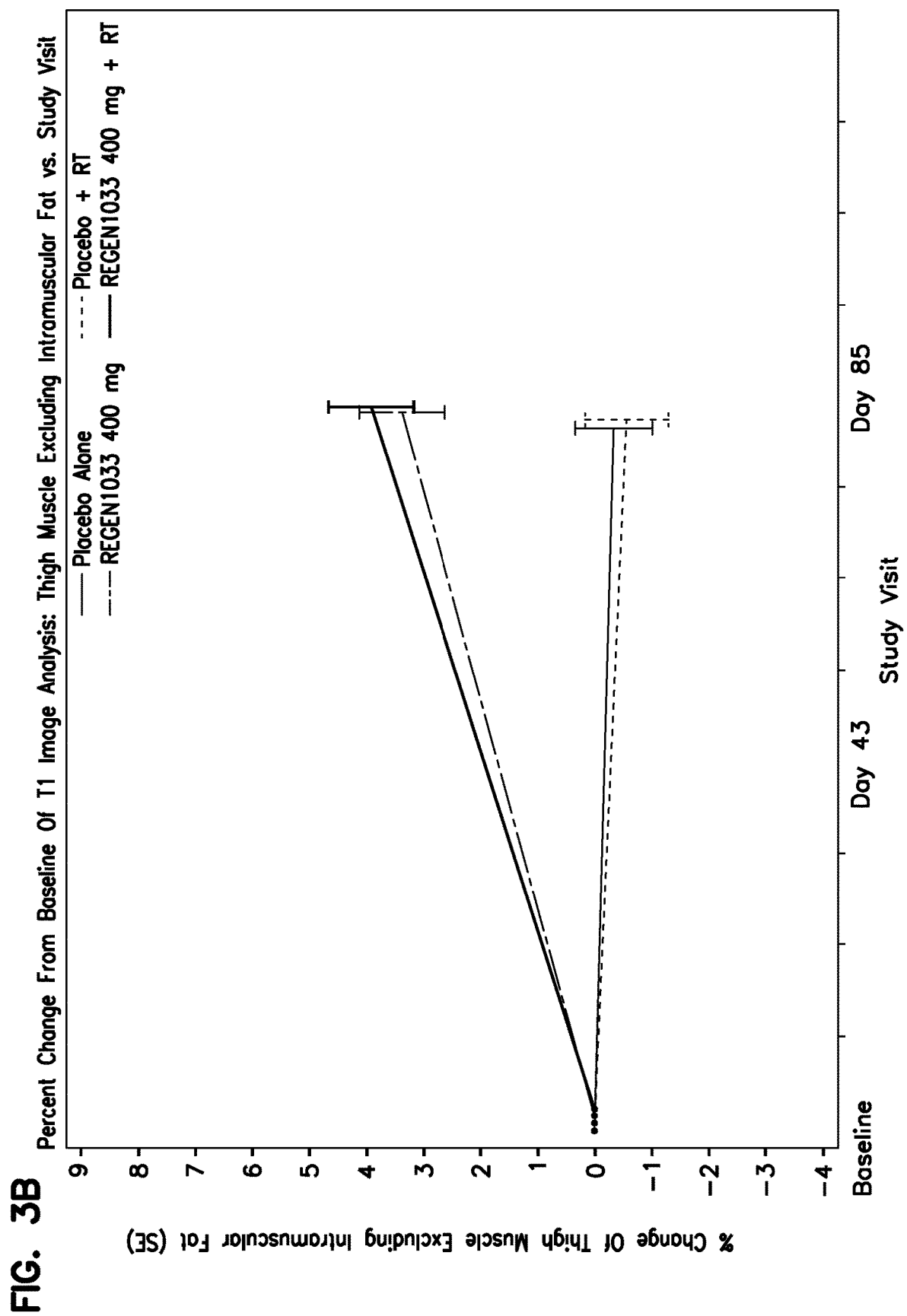

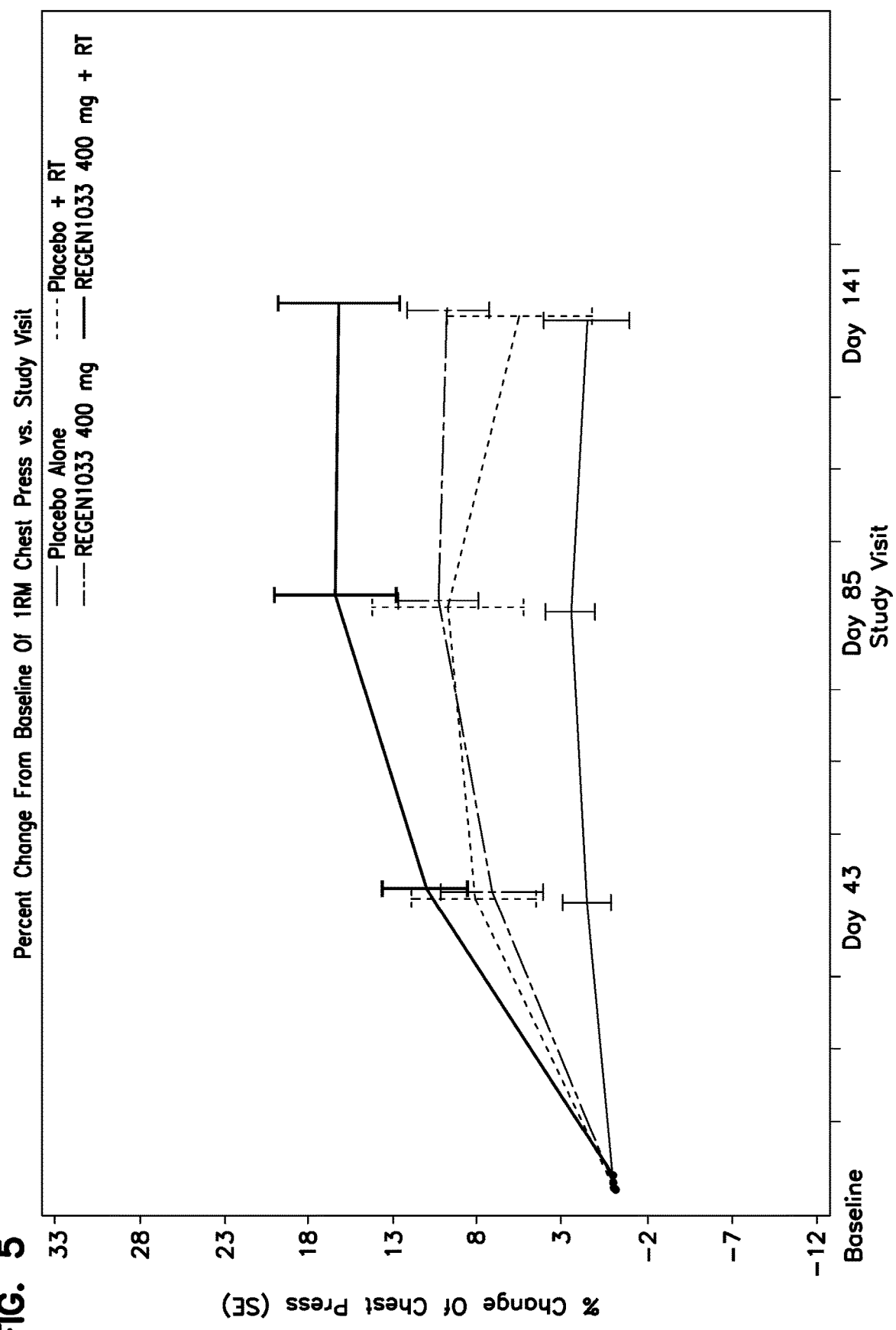

SEQUENCE LISTING

<160> NUMBER OF SEQ ID NOS: 391

<210> SEQ ID NO 1
<211> LENGTH: 366
<212> TYPE: DNA
<213> ORGANISM: Artificial Sequence
<220> FEATURE:
<223> OTHER INFORMATION: Synthetic

<400> SEQUENCE: 1

```
caggtgcagc tggtgcagtc tggggggaggc ttggtccagc ctgggggtc cctgagactc      60 tcctgtgcag cctctggatt cacctttaac acctatgcca taagctgggt ccgccaggct     120
ccagggaagg gctggaatg ggtctcaact attactggta gtggttataa cacatactac     180
gcagactccg tgaagggccg gttcaccatc tccagagaca attccaagaa cacactgtat     240
ctacagatga gcagcctgag agccgaggac acggccgtat tttactgtgc gaaagactct     300
cggtataact ggaattacgg aattttgac tactggggcc agggaaccac ggtcaccgtc     360
tcctca                                                                366
```

<210> SEQ ID NO 2
<211> LENGTH: 122
<212> TYPE: PRT
<213> ORGANISM: Artificial Sequence
<220> FEATURE:
<223> OTHER INFORMATION: Synthetic

<400> SEQUENCE: 2

```
Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Ile Ser Trp Val Arg Gln Ala Pro Gly Lys Gly Leu Glu Trp Val
        35                  40                  45

Ser Thr Ile Thr Gly Ser Gly Tyr Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Val Phe Tyr Cys
                85                  90                  95

Ala Lys Asp Ser Arg Tyr Asn Trp Asn Tyr Gly Ile Phe Asp Tyr Trp
            100                 105                 110

Gly Gln Gly Thr Thr Val Thr Val Ser Ser
        115                 120
```

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3

```
ggattcacct ttaacaccta tgcc                                              24
```

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

Gly Phe Thr Phe Asn Thr Tyr Ala
1               5

<210> SEQ ID NO 5
<211> LENGTH: 24
<212> TYPE: DNA
<213> ORGANISM: Artificial Sequence
<220> FEATURE:
<223> OTHER INFORMATION: Synthetic

<400> SEQUENCE: 5
attactggta gtggttataa caca                                          24

<210> SEQ ID NO 6
<211> LENGTH: 8
<212> TYPE: PRT
<213> ORGANISM: Artificial Sequence
<220> FEATURE:
<223> OTHER INFORMATION: Synthetic

<400> SEQUENCE: 6

Ile Thr Gly Ser Gly Tyr Asn Thr
1               5

<210> SEQ ID NO 7
<211> LENGTH: 45
<212> TYPE: DNA
<213> ORGANISM: Artificial Sequence
<220> FEATURE:
<223> OTHER INFORMATION: Synthetic

<400> SEQUENCE: 7
gcgaaagact ctcggtataa ctggaattac ggaattttg actac                    45

<210> SEQ ID NO 8
<211> LENGTH: 15
<212> TYPE: PRT
<213> ORGANISM: Artificial Sequence
<220> FEATURE:
<223> OTHER INFORMATION: Synthetic

<400> SEQUENCE: 8

Ala Lys Asp Ser Arg Tyr Asn Trp Asn Tyr Gly Ile Phe Asp Tyr
1               5                   10                  15

<210> SEQ ID NO 9
<211> LENGTH: 324
<212> TYPE: DNA
<213> ORGANISM: Artificial Sequence
<220> FEATURE:
<223> OTHER INFORMATION: Synthetic

<400> SEQUENCE: 9
gacatccaga tgacccagtc tccagccacc ctgtctgtgt ctccagggga aagagccacc    60
ctctcctgca gggccagtca gagtgttagc agcaacttag cctggtacca tcagaaacct   120
ggccaggctc ccaggctcct catctatggt gtatccacca gggccactgg tatcccagcc   180
aggttcagtg gcaatgggtc tgggacagag ttcactctca ccatcagcag cctgcagtct   240
gaagattttg cagtttatta ctgtcagcag cataataact ggccgctcac tttcggcgga   300
gggaccaagg tggagatcaa acga                                         324

<210> SEQ ID NO 10
<211> LENGTH: 108
<212> TYPE: PRT
<213> ORGANISM: Artificial Sequence
<220> FEATURE:
<223> OTHER INFORMATION: Synthetic

<400> SEQUENCE: 10

```
Asp Ile Gln Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr His Gln Lys Pro Gly Gln Ala Pro Arg Leu Leu Ile
        35                  40                  45

Tyr Gly Val Ser Thr Arg Ala Thr Gly Ile Pro Ala Arg Phe Ser Gly
    50                  55                  60

Asn Gly Ser Gly Thr Glu Phe Thr Leu Thr Ile Ser Ser Leu Gln Ser
65                  70                  75                  80

Glu Asp Phe Ala Val Tyr Tyr Cys Gln Gln His Asn Asn Trp Pro Leu
                85                  90                  95

Thr Phe Gly Gly Gly Thr Lys Val Glu Ile Lys Arg
            100                 105
```

<210> SEQ ID NO 11
<211> LENGTH: 18
<212> TYPE: DNA
<213> ORGANISM: Artificial Sequence
<220> FEATURE:
<223> OTHER INFORMATION: Synthetic

<400> SEQUENCE: 11
cagagtgtta gcagcaac                                                   18

<210> SEQ ID NO 12
<211> LENGTH: 6
<212> TYPE: PRT
<213> ORGANISM: Artificial Sequence
<220> FEATURE:
<223> OTHER INFORMATION: Synthetic

<400> SEQUENCE: 12

```
Gln Ser Val Ser Ser Asn
1               5
```

<210> SEQ ID NO 13
<211> LENGTH: 9
<212> TYPE: DNA
<213> ORGANISM: Artificial Sequence
<220> FEATURE:
<223> OTHER INFORMATION: Synthetic

<400> SEQUENCE: 13 ggtgtatcc                                                              9

<210> SEQ ID NO 14
<211> LENGTH: 3
<212> TYPE: PRT
<213> ORGANISM: Artificial Sequence
<220> FEATURE:
<223> OTHER INFORMATION: Synthetic

<400> SEQUENCE: 14

```
Gly Val Ser
1
```

<210> SEQ ID NO 15
<211> LENGTH: 27
<212> TYPE: DNA
<213> ORGANISM: Artificial Sequence
<220> FEATURE:
<223> OTHER INFORMATION: Synthetic

<400> SEQUENCE: 15
cagcagcata taactggcc gctcact                                           27

<210> SEQ ID NO 16
<211> LENGTH: 9
<212> TYPE: PRT
<213> ORGANISM: Artificial Sequence
<220> FEATURE:
<223> OTHER INFORMATION: Synthetic

<400> SEQUENCE: 16

Gln Gln His Asn Asn Trp Pro Leu Thr
1               5

<210> SEQ ID NO 17
<211> LENGTH: 375
<212> TYPE: DNA
<213> ORGANISM: Artificial Sequence
<220> FEATURE:
<223> OTHER INFORMATION: Synthetic

<400> SEQUENCE: 17
caggtgcagc tggtgcagtc gggcccagga ctggtgaagc cttcggagac cctgtccctc      60
acctgcactg tctctggtgg ctccatcagc aatagtaatt actactgggg ctggatccgc     120
cagcccccag ggaaggggct ggagtggatt gggactacct attatagtgg gaccacctac     180
tacaacccgt ccctcaagag tcgagtcacc atatccgtag acacgtccaa gaaccagttc     240
tccctgaagc tgagctctgt gaccgccgca gacacggctg tgtattactg tgcgagagat     300
tattatgata gtagtggtta ttattacaac tggttcgatc cctggggcca gggaaccacg     360
gtcaccgtct cctca                                                     375

<210> SEQ ID NO 18
<211> LENGTH: 125
<212> TYPE: PRT
<213> ORGANISM: Artificial Sequence
<220> FEATURE:
<223> OTHER INFORMATION: Synthetic

<400> SEQUENCE: 18

Gln Val Gln Leu Val Gln Ser Gly Pro Gly Leu Val Lys Pro Ser Glu
1               5                   10                  15

Thr Leu Ser Leu Thr Cys Thr Val Ser Gly Gly Ser Ile Ser Asn Ser
            20                  25                  30

Asn Tyr Tyr Trp Gly Trp Ile Arg Gln Pro Pro Gly Lys Gly Leu Glu
        35                  40                  45

Trp Ile Gly Thr Thr Tyr Tyr Ser Gly Thr Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Tyr Tyr Asp Ser Ser Gly Tyr Tyr Tyr Asn Trp Phe

```
                100              105              110
Asp Pro Trp Gly Gln Gly Thr Thr Val Thr Val Ser Ser
        115              120              125

<210> SEQ ID NO 19
<211> LENGTH: 30
<212> TYPE: DNA
<213> ORGANISM: Artificial Sequence
<220> FEATURE:
<223> OTHER INFORMATION: Synthetic

<400> SEQUENCE: 19
ggtggctcca tcagcaatag taattactac                                    30

<210> SEQ ID NO 20
<211> LENGTH: 10
<212> TYPE: PRT
<213> ORGANISM: Artificial Sequence
<220> FEATURE:
<223> OTHER INFORMATION: Synthetic

<400> SEQUENCE: 20

Gly Gly Ser Ile Ser Asn Ser Asn Tyr Tyr
1               5                   10

<210> SEQ ID NO 21
<211> LENGTH: 21
<212> TYPE: DNA
<213> ORGANISM: Artificial Sequence
<220> FEATURE:
<223> OTHER INFORMATION: Synthetic

<400> SEQUENCE: 21
acctattata gtgggaccac c                                             21

<210> SEQ ID NO 22
<211> LENGTH: 7
<212> TYPE: PRT
<213> ORGANISM: Artificial Sequence
<220> FEATURE:
<223> OTHER INFORMATION: Synthetic

<400> SEQUENCE: 22

Thr Tyr Tyr Ser Gly Thr Thr
1               5

<210> SEQ ID NO 23
<211> LENGTH: 51
<212> TYPE: DNA
<213> ORGANISM: Artificial Sequence
<220> FEATURE:
<223> OTHER INFORMATION: Synthetic

<400> SEQUENCE: 23
gcgagagatt attatgatag tagtggttat tattacaact ggttcgatcc c            51

<210> SEQ ID NO 24
<211> LENGTH: 17
<212> TYPE: PRT
<213> ORGANISM: Artificial Sequence
<220> FEATURE:
<223> OTHER INFORMATION: Synthetic

<400> SEQUENCE: 24

Ala Arg Asp Tyr Tyr Asp Ser Ser Gly Tyr Tyr Tyr Asn Trp Phe Asp
1               5                   10                  15
```

Pro

<210> SEQ ID NO 25
<211> LENGTH: 324
<212> TYPE: DNA
<213> ORGANISM: Artificial Sequence
<220> FEATURE:
<223> OTHER INFORMATION: Synthetic

<400> SEQUENCE: 25

```
gacatccagt tgacccagtc tccatcctcc ctgtctgcat ctgtaggaga cagagtcacc      60
atcacttgcc gggcaagtca ggacattaga aatgatttag gctggtatca gcagaaacca     120
gggaaagccc ctaagcgcct gatctatgct gcatccagtt tgcaaagtgg ggtcccatca     180
aggttcagcg gcagtggatc tgggacagaa ttcagtctca cactcagcag cctgcagcct     240
gaagattttg caacttattt ctgtctacag catcatattt acccgtggac gttcggccaa     300
gggaccaagc tggagatcaa acga                                            324
```

<210> SEQ ID NO 26
<211> LENGTH: 108
<212> TYPE: PRT
<213> ORGANISM: Artificial Sequence
<220> FEATURE:
<223> OTHER INFORMATION: Synthetic

<400> SEQUENCE: 26

Asp Ile Gln Leu Thr Gln Ser Pro Ser Ser Leu Ser Ala Ser Val Gly
1               5                   10                  15
Asp Arg Val Thr Ile Thr Cys Arg Ala Ser Gln Asp Ile Arg Asn Asp
            20                  25                  30
Leu Gly Trp Tyr Gln Gln Lys Pro Gly Lys Ala Pro Lys Arg Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Glu Phe Ser Leu Thr Leu Ser Ser Leu Gln Pro
65                  70                  75                  80
Glu Asp Phe Ala Thr Tyr Phe Cys Leu Gln His His Ile Tyr Pro Trp
                85                  90                  95
Thr Phe Gly Gln Gly Thr Lys Leu Glu Ile Lys Arg
            100                 105

<210> SEQ ID NO 27
<211> LENGTH: 18
<212> TYPE: DNA
<213> ORGANISM: Artificial Sequence
<220> FEATURE:
<223> OTHER INFORMATION: Synthetic

<400> SEQUENCE: 27

```
caggacatta gaaatgat                                                    18
```

<210> SEQ ID NO 28
<211> LENGTH: 6
<212> TYPE: PRT
<213> ORGANISM: Artificial Sequence
<220> FEATURE:
<223> OTHER INFORMATION: Synthetic

<400> SEQUENCE: 28

Gln Asp Ile Arg Asn Asp

<210> SEQ ID NO 29
<211> LENGTH: 9
<212> TYPE: DNA
<213> ORGANISM: Artificial Sequence
<220> FEATURE:
<223> OTHER INFORMATION: Synthetic

<400> SEQUENCE: 29 gctgcatcc                                                                    9

<210> SEQ ID NO 30
<211> LENGTH: 3
<212> TYPE: PRT
<213> ORGANISM: Artificial Sequence
<220> FEATURE:
<223> OTHER INFORMATION: Synthetic

<400> SEQUENCE: 30

Ala Ala Ser
1

<210> SEQ ID NO 31
<211> LENGTH: 27
<212> TYPE: DNA
<213> ORGANISM: Artificial Sequence
<220> FEATURE:
<223> OTHER INFORMATION: Synthetic

<400> SEQUENCE: 31
ctacagcatc atatttaccc gtggacg                                               27

<210> SEQ ID NO 32
<211> LENGTH: 9
<212> TYPE: PRT
<213> ORGANISM: Artificial Sequence
<220> FEATURE:
<223> OTHER INFORMATION: Synthetic

<400> SEQUENCE: 32

Leu Gln His His Ile Tyr Pro Trp Thr
1               5

<210> SEQ ID NO 33
<211> LENGTH: 375
<212> TYPE: DNA
<213> ORGANISM: Artificial Sequence
<220> FEATURE:
<223> OTHER INFORMATION: Synthetic

<400> SEQUENCE: 33
caagttcagc tggtggagtc gggcccagga ctggtgaagc cttcggagac cctgtccctc           60
acctgcactg tctatggtgg ctccatcagc agtggtaatt actactgggg ctggatccgc          120
cagcccccag ggaagggact ggagtggatt gggactatct attatagtgg aagcgcctac          180 acaacccgt ccctcaagag tcgagtcacc atgtccgtag acacgtccaa gaaccagttc           240
tccctgaaac tgagctctgt gaccgccgca gacacggctg tttattactg tgtgagagat          300
tactatgata gtagtggtca ttattacaac tggttcgacc cctggggcca gggaaccacg          360
gtcaccgtct cctca                                                           375

<210> SEQ ID NO 34
<211> LENGTH: 125

```
<212> TYPE: PRT
<213> ORGANISM: Artificial Sequence
<220> FEATURE:
<223> OTHER INFORMATION: Synthetic

<400> SEQUENCE: 34

Gln Val Gln Leu Val Glu Ser Gly Pro Gly Leu Val Lys Pro Ser Glu
1               5                   10                  15

Thr Leu Ser Leu Thr Cys Thr Val Tyr Gly Gly Ser Ile Ser Ser Gly
            20                  25                  30

Asn Tyr Tyr Trp Gly Trp Ile Arg Gln Pro Pro Gly Lys Gly Leu Glu
        35                  40                  45

Trp Ile Gly Thr Ile Tyr Tyr Ser Gly Ser Ala Tyr Tyr Asn Pro Ser
    50                  55                  60

Leu Lys Ser Arg Val Thr Met Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Val Arg Asp Tyr Tyr Asp Ser Ser Gly His Tyr Tyr Asn Trp Phe
            100                 105                 110

Asp Pro Trp Gly Gln Gly Thr Thr Val Thr Val Ser Ser
        115                 120                 125

<210> SEQ ID NO 35
<211> LENGTH: 30
<212> TYPE: DNA
<213> ORGANISM: Artificial Sequence
<220> FEATURE:
<223> OTHER INFORMATION: Synthetic

<400> SEQUENCE: 35
ggtggctcca tcagcagtgg taattactac                                    30

<210> SEQ ID NO 36
<211> LENGTH: 10
<212> TYPE: PRT
<213> ORGANISM: Artificial Sequence
<220> FEATURE:
<223> OTHER INFORMATION: Synthetic

<400> SEQUENCE: 36

Gly Gly Ser Ile Ser Ser Gly Asn Tyr Tyr
1               5                   10

<210> SEQ ID NO 37
<211> LENGTH: 21
<212> TYPE: DNA
<213> ORGANISM: Artificial Sequence
<220> FEATURE:
<223> OTHER INFORMATION: Synthetic

<400> SEQUENCE: 37
atctattata gtggaagcgc c                                             21

<210> SEQ ID NO 38
<211> LENGTH: 7
<212> TYPE: PRT
<213> ORGANISM: Artificial Sequence
<220> FEATURE:
<223> OTHER INFORMATION: Synthetic

<400> SEQUENCE: 38

Ile Tyr Tyr Ser Gly Ser Ala
```

<210> SEQ ID NO 39
<211> LENGTH: 51
<212> TYPE: DNA
<213> ORGANISM: Artificial Sequence
<220> FEATURE:
<223> OTHER INFORMATION: Synthetic

<400> SEQUENCE: 39
gtgagagatt actatgatag tagtggtcat tattacaact ggttcgaccc c        51

<210> SEQ ID NO 40
<211> LENGTH: 17
<212> TYPE: PRT
<213> ORGANISM: Artificial Sequence
<220> FEATURE:
<223> OTHER INFORMATION: Synthetic

<400> SEQUENCE: 40

Val Arg Asp Tyr Tyr Asp Ser Ser Gly His Tyr Tyr Asn Trp Phe Asp
1               5                   10                  15

Pro

<210> SEQ ID NO 41
<211> LENGTH: 324
<212> TYPE: DNA
<213> ORGANISM: Artificial Sequence
<220> FEATURE:
<223> OTHER INFORMATION: Synthetic

<400> SEQUENCE: 41
gccatccaga tgacccagtc tccatcctcc ctgtctgcat ctgtaggaga cagagtcacc     60
atcacttgcc gggcaagtca ggacattaga catgatttag ctggtatca gcagaaacca    120 gggaaagccc ctaagcgcct gatctatgct gcatccagtt tgcaaagtgg ggtcccatca    180
aggttcagcg gcagtggatc tgggacagaa ttcactctca caatcagcag cctgcagcct    240
gaagattttg caacttatta ctgtctacag cataatactt acccgtggac gttcggccaa    300
gggaccaagg tggagatcaa acga                                          324

<210> SEQ ID NO 42
<211> LENGTH: 108
<212> TYPE: PRT
<213> ORGANISM: Artificial Sequence
<220> FEATURE:
<223> OTHER INFORMATION: Synthetic

<400> SEQUENCE: 42

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg His Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Thr Tyr Pro Trp
                85                  90                  95

Thr Phe Gly Gln Gly Thr Lys Val Glu Ile Lys Arg
            100                 105

<210> SEQ ID NO 43
<211> LENGTH: 18
<212> TYPE: DNA
<213> ORGANISM: Artificial Sequence
<220> FEATURE:
<223> OTHER INFORMATION: Synthetic

<400> SEQUENCE: 43
caggacatta gacatgat                                                   18

<210> SEQ ID NO 44
<211> LENGTH: 6
<212> TYPE: PRT
<213> ORGANISM: Artificial Sequence
<220> FEATURE:
<223> OTHER INFORMATION: Synthetic

<400> SEQUENCE: 44

Gln Asp Ile Arg His Asp
1               5

<210> SEQ ID NO 45
<211> LENGTH: 9
<212> TYPE: DNA
<213> ORGANISM: Artificial Sequence
<220> FEATURE:
<223> OTHER INFORMATION: Synthetic

<400> SEQUENCE: 45 gctgcatcc                                                              9

<210> SEQ ID NO 46
<211> LENGTH: 3
<212> TYPE: PRT
<213> ORGANISM: Artificial Sequence
<220> FEATURE:
<223> OTHER INFORMATION: Synthetic

<400> SEQUENCE: 46

Ala Ala Ser
1

<210> SEQ ID NO 47
<211> LENGTH: 27
<212> TYPE: DNA
<213> ORGANISM: Artificial Sequence
<220> FEATURE:
<223> OTHER INFORMATION: Synthetic

<400> SEQUENCE: 47
ctacagcata atacttaccc gtggacg                                         27

<210> SEQ ID NO 48
<211> LENGTH: 9
<212> TYPE: PRT
<213> ORGANISM: Artificial Sequence
<220> FEATURE:
<223> OTHER INFORMATION: Synthetic

<400> SEQUENCE: 48

Leu Gln His Asn Thr Tyr Pro Trp Thr
1               5

-continued

```
<210> SEQ ID NO 49
<211> LENGTH: 357
<212> TYPE: DNA
<213> ORGANISM: Artificial Sequence
<220> FEATURE:
<223> OTHER INFORMATION: Synthetic

<400> SEQUENCE: 49
caggtgcagc tggtgcagtc tgggggaggc ctggtcaagc ctggggggtc cctgagactc      60
tcctgtgcag cctctggatt caccttcagt agctatagca tgaactgggt ccgccaggct     120
ccagggaagg ggctggagtg ggtctcatcc attagtagta gtagtagtta catatactac     180
gcagactcag tgaagggccg attcaccatc tccagagaca cgccaagaa ctcactgtat      240 ctgcaaatga acagcctgag agccgaggac acggctgtgt attactgtgc gagagatcgt     300
ggatacacct ttggggttga ctactggggc cagggaacca cggtcaccgt ctcctca        357

<210> SEQ ID NO 50
<211> LENGTH: 119
<212> TYPE: PRT
<213> ORGANISM: Artificial Sequence
<220> FEATURE:
<223> OTHER INFORMATION: Synthetic

<400> SEQUENCE: 50

Gln Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Tyr Thr Phe Gly Val Asp Tyr Trp Gly Gln Gly
            100                 105                 110

Thr Thr Val Thr Val Ser Ser
        115

<210> SEQ ID NO 51
<211> LENGTH: 24
<212> TYPE: DNA
<213> ORGANISM: Artificial Sequence
<220> FEATURE:
<223> OTHER INFORMATION: Synthetic

<400> SEQUENCE: 51
ggattcacct tcagtagcta tagc                                             24

<210> SEQ ID NO 52
<211> LENGTH: 8
<212> TYPE: PRT
<213> ORGANISM: Artificial Sequence
<220> FEATURE:
<223> OTHER INFORMATION: Synthetic

<400> SEQUENCE: 52

Gly Phe Thr Phe Ser Ser Tyr Ser
1               5
```

<210> SEQ ID NO 53
<211> LENGTH: 24
<212> TYPE: DNA
<213> ORGANISM: Artificial Sequence
<220> FEATURE:
<223> OTHER INFORMATION: Synthetic

<400> SEQUENCE: 53
attagtagta gtagtagtta cata                                            24

<210> SEQ ID NO 54
<211> LENGTH: 8
<212> TYPE: PRT
<213> ORGANISM: Artificial Sequence
<220> FEATURE:
<223> OTHER INFORMATION: Synthetic

<400> SEQUENCE: 54

Ile Ser Ser Ser Ser Ser Tyr Ile
1               5

<210> SEQ ID NO 55
<211> LENGTH: 36
<212> TYPE: DNA
<213> ORGANISM: Artificial Sequence
<220> FEATURE:
<223> OTHER INFORMATION: Synthetic

<400> SEQUENCE: 55
gcgagagatc gtggatacac ctttggggtt gactac                               36

<210> SEQ ID NO 56
<211> LENGTH: 12
<212> TYPE: PRT
<213> ORGANISM: Artificial Sequence
<220> FEATURE:
<223> OTHER INFORMATION: Synthetic

<400> SEQUENCE: 56

Ala Arg Asp Arg Gly Tyr Thr Phe Gly Val Asp Tyr
1               5                   10

<210> SEQ ID NO 57
<211> LENGTH: 324
<212> TYPE: DNA
<213> ORGANISM: Artificial Sequence
<220> FEATURE:
<223> OTHER INFORMATION: Synthetic

<400> SEQUENCE: 57
gccatccaga tgacccagtc tccatcctcc ctgtctgcat ctgtaggaga cagagtcacc     60
atcacttgcc gggcaagtca gggcattaga aatgatttag ctggtatca gcagaaacca    120 gggaaagccc ctaagcgcct gatctatgct gcatccagtt tgcaaagtgg ggtcccatca    180
aggttcagcg gcagtggatc tgggacagaa ttcactctca caatcagcag cctgcagcct    240
gaagattttg caacttatta ctgtctacag cataatagtt acccgtacac ttttggccag    300
gggaccaagg tggagatcaa acga                                           324

<210> SEQ ID NO 58
<211> LENGTH: 108
<212> TYPE: PRT
<213> ORGANISM: Artificial Sequence
<220> FEATURE:

<223> OTHER INFORMATION: Synthetic

<400> SEQUENCE: 58

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Tyr
                85                  90                  95

Thr Phe Gly Gln Gly Thr Lys Val Glu Ile Lys Arg
            100                 105

<210> SEQ ID NO 59
<211> LENGTH: 18
<212> TYPE: DNA
<213> ORGANISM: Artificial Sequence
<220> FEATURE:
<223> OTHER INFORMATION: Synthetic

<400> SEQUENCE: 59
cagggcatta gaaatgat                                                 18

<210> SEQ ID NO 60
<211> LENGTH: 6
<212> TYPE: PRT
<213> ORGANISM: Artificial Sequence
<220> FEATURE:
<223> OTHER INFORMATION: Synthetic

<400> SEQUENCE: 60

Gln Gly Ile Arg Asn Asp
1               5

<210> SEQ ID NO 61
<211> LENGTH: 9
<212> TYPE: DNA
<213> ORGANISM: Artificial Sequence
<220> FEATURE:
<223> OTHER INFORMATION: Synthetic

<400> SEQUENCE: 61 gctgcatcc                                                            9

<210> SEQ ID NO 62
<211> LENGTH: 3
<212> TYPE: PRT
<213> ORGANISM: Artificial Sequence
<220> FEATURE:
<223> OTHER INFORMATION: Synthetic

<400> SEQUENCE: 62

Ala Ala Ser
1

<210> SEQ ID NO 63
<211> LENGTH: 27
<212> TYPE: DNA

<213> ORGANISM: Artificial Sequence
<220> FEATURE:
<223> OTHER INFORMATION: Synthetic

<400> SEQUENCE: 63
ctacagcata atagttaccc gtacact                                               27

<210> SEQ ID NO 64
<211> LENGTH: 9
<212> TYPE: PRT
<213> ORGANISM: Artificial Sequence
<220> FEATURE:
<223> OTHER INFORMATION: Synthetic

<400> SEQUENCE: 64

Leu Gln His Asn Ser Tyr Pro Tyr Thr
1               5

<210> SEQ ID NO 65
<211> LENGTH: 375
<212> TYPE: DNA
<213> ORGANISM: Artificial Sequence
<220> FEATURE:
<223> OTHER INFORMATION: Synthetic

<400> SEQUENCE: 65
caggtgcagc tggtgcagtc gggcccagga ctggtgaagc cttcggagac cctgtccctc           60
acctgcactg tctctggtgg ctccatcatc acttatagtt actactgggg ctggatccgc          120
cagcccccag ggaaggggct ggagtggatt gggactatcc atcatagtgg gagcacctac          180
tacaacccgt ccctcaagag tcgagtcacc atatccgtag acacgtccaa gaaccagttc          240
tccctgacac tgagttctgt gaccgccgca gacacggctg tgtattactg tgcgagagac          300
tactatgata gtagtggtta ttattataac tggttcgacc cctggggcca gggaaccatg          360
gtcaccgtct cctca                                                          375

<210> SEQ ID NO 66
<211> LENGTH: 125
<212> TYPE: PRT
<213> ORGANISM: Artificial Sequence
<220> FEATURE:
<223> OTHER INFORMATION: Synthetic

<400> SEQUENCE: 66

Gln Val Gln Leu Val Gln Ser Gly Pro Gly Leu Val Lys Pro Ser Glu
1               5                   10                  15

Thr Leu Ser Leu Thr Cys Thr Val Ser Gly Gly Ser Ile Ile Thr Tyr
            20                  25                  30

Ser Tyr Tyr Trp Gly Trp Ile Arg Gln Pro Pro Gly Lys Gly Leu Glu
        35                  40                  45

Trp Ile Gly Thr Ile His His Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Thr Leu Ser Ser Val Thr Ala Ala Asp Thr Ala Val Tyr Tyr
                85                  90                  95

Cys Ala Arg Asp Tyr Tyr Asp Ser Ser Gly Tyr Tyr Tyr Asn Trp Phe
            100                 105                 110

Asp Pro Trp Gly Gln Gly Thr Met Val Thr Val Ser Ser
        115                 120                 125

```
<210> SEQ ID NO 67
<211> LENGTH: 30
<212> TYPE: DNA
<213> ORGANISM: Artificial Sequence
<220> FEATURE:
<223> OTHER INFORMATION: Synthetic

<400> SEQUENCE: 67
ggtggctcca tcatcactta tagttactac                                          30

<210> SEQ ID NO 68
<211> LENGTH: 10
<212> TYPE: PRT
<213> ORGANISM: Artificial Sequence
<220> FEATURE:
<223> OTHER INFORMATION: Synthetic

<400> SEQUENCE: 68

Gly Gly Ser Ile Ile Thr Tyr Ser Tyr Tyr
1               5                   10

<210> SEQ ID NO 69
<211> LENGTH: 21
<212> TYPE: DNA
<213> ORGANISM: Artificial Sequence
<220> FEATURE:
<223> OTHER INFORMATION: Synthetic

<400> SEQUENCE: 69
atccatcata gtgggagcac c                                                   21

<210> SEQ ID NO 70
<211> LENGTH: 7
<212> TYPE: PRT
<213> ORGANISM: Artificial Sequence
<220> FEATURE:
<223> OTHER INFORMATION: Synthetic

<400> SEQUENCE: 70

Ile His His Ser Gly Ser Thr
1               5

<210> SEQ ID NO 71
<211> LENGTH: 51
<212> TYPE: DNA
<213> ORGANISM: Artificial Sequence
<220> FEATURE:
<223> OTHER INFORMATION: Synthetic

<400> SEQUENCE: 71
gcgagagact actatgatag tagtggttat tattataact ggttcgaccc c                  51

<210> SEQ ID NO 72
<211> LENGTH: 17
<212> TYPE: PRT
<213> ORGANISM: Artificial Sequence
<220> FEATURE:
<223> OTHER INFORMATION: Synthetic

<400> SEQUENCE: 72

Ala Arg Asp Tyr Tyr Asp Ser Ser Gly Tyr Tyr Tyr Asn Trp Phe Asp
1               5                   10                  15
Pro

<210> SEQ ID NO 73
```

<211> LENGTH: 324
<212> TYPE: DNA
<213> ORGANISM: Artificial Sequence
<220> FEATURE:
<223> OTHER INFORMATION: Synthetic

<400> SEQUENCE: 73

```
gccatccaga tgacccagtc tccatcctcc ctgtctgcat ctgtaggaga cagagtcacc    60
atcacttgcc gggcaagtca gggcattaga aatgatttag ctggtatca gcagaaacca   120
gggaaagccc ctaagcgcct gatctatgct gcatccagtt tgcaaagtgg ggtcccatca   180
aggttcagcg gcagtggatc tgggacagaa ttcactctca caatcagcag cctgcagcct   240
gaagattttg caacttatta ctgtctacag cataatagtt ccccgtggac gttcggccaa   300
gggaccaagg tggagatcaa acga                                         324
```

<210> SEQ ID NO 74
<211> LENGTH: 108
<212> TYPE: PRT
<213> ORGANISM: Artificial Sequence
<220> FEATURE:
<223> OTHER INFORMATION: Synthetic

<400> SEQUENCE: 74

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Ser Pro Trp
                85                  90                  95

Thr Phe Gly Gln Gly Thr Lys Val Glu Ile Lys Arg
            100                 105

<210> SEQ ID NO 75
<211> LENGTH: 18
<212> TYPE: DNA
<213> ORGANISM: Artificial Sequence
<220> FEATURE:
<223> OTHER INFORMATION: Synthetic

<400> SEQUENCE: 75

```
cagggcatta gaaatgat                                                 18
```

<210> SEQ ID NO 76
<211> LENGTH: 6
<212> TYPE: PRT
<213> ORGANISM: Artificial Sequence
<220> FEATURE:
<223> OTHER INFORMATION: Synthetic

<400> SEQUENCE: 76

Gln Gly Ile Arg Asn Asp
1               5

<210> SEQ ID NO 77
<211> LENGTH: 9

```
<212> TYPE: DNA
<213> ORGANISM: Artificial Sequence
<220> FEATURE:
<223> OTHER INFORMATION: Synthetic

<400> SEQUENCE: 77 gctgcatcc                                                             9

<210> SEQ ID NO 78
<211> LENGTH: 3
<212> TYPE: PRT
<213> ORGANISM: Artificial Sequence
<220> FEATURE:
<223> OTHER INFORMATION: Synthetic

<400> SEQUENCE: 78

Ala Ala Ser
1

<210> SEQ ID NO 79
<211> LENGTH: 27
<212> TYPE: DNA
<213> ORGANISM: Artificial Sequence
<220> FEATURE:
<223> OTHER INFORMATION: Synthetic

<400> SEQUENCE: 79
ctacagcata atagttcccc gtggacg                                        27

<210> SEQ ID NO 80
<211> LENGTH: 9
<212> TYPE: PRT
<213> ORGANISM: Artificial Sequence
<220> FEATURE:
<223> OTHER INFORMATION: Synthetic

<400> SEQUENCE: 80

Leu Gln His Asn Ser Ser Pro Trp Thr
1               5

<210> SEQ ID NO 81
<211> LENGTH: 369
<212> TYPE: DNA
<213> ORGANISM: Artificial Sequence
<220> FEATURE:
<223> OTHER INFORMATION: Synthetic

<400> SEQUENCE: 81
caggtgcact tgaaggagtc tggtcctacg ctggtgaaac ccacacagac cctcacgctg     60
acctgcacct tctctgggtt ctcactcagc actagtggag tgggtgtggg ctggatccgt    120
cagcccccag gaaaggccct ggagtggctt gcactcattt attggaatga tgataagcgc    180
tacagcccat ctctgaagag caggctcacc atcaccaagg acacctccaa aaaccaggtg    240
gtccttacaa tgaccaacat ggaccctgtg gacagcca catattactg tacacacacc      300
tcccgttata actggcacta cggcttcctt gactactggg gccagggaac cacggtcacc    360
gtctcctca                                                           369

<210> SEQ ID NO 82
<211> LENGTH: 123
<212> TYPE: PRT
<213> ORGANISM: Artificial Sequence
<220> FEATURE:
<223> OTHER INFORMATION: Synthetic
```

<400> SEQUENCE: 82

Gln Val His Leu Lys Glu Ser Gly Pro Thr Leu Val Lys Pro Thr Gln
1               5                   10                  15
Thr Leu Thr Leu Thr Cys Thr Phe Ser Gly Phe Ser Leu Ser Thr Ser
            20                  25                  30
Gly Val Gly Val Gly Trp Ile Arg Gln Pro Pro Gly Lys Ala Leu Glu
        35                  40                  45
Trp Leu Ala Leu Ile Tyr Trp Asn Asp Asp Lys Arg Tyr Ser Pro Ser
    50                  55                  60
Leu Lys Ser Arg Leu Thr Ile Thr Lys Asp Thr Ser Lys Asn Gln Val
65                  70                  75                  80
Val Leu Thr Met Thr Asn Met Asp Pro Val Asp Thr Ala Thr Tyr Tyr
                85                  90                  95
Cys Thr His Thr Ser Arg Tyr Asn Trp His Tyr Gly Phe Leu Asp Tyr
            100                 105                 110
Trp Gly Gln Gly Thr Thr Val Thr Val Ser Ser
        115                 120

<210> SEQ ID NO 83
<211> LENGTH: 30
<212> TYPE: DNA
<213> ORGANISM: Artificial Sequence
<220> FEATURE:
<223> OTHER INFORMATION: Synthetic

<400> SEQUENCE: 83
gggttctcac tcagcactag tggagtgggt                                    30

<210> SEQ ID NO 84
<211> LENGTH: 10
<212> TYPE: PRT
<213> ORGANISM: Artificial Sequence
<220> FEATURE:
<223> OTHER INFORMATION: Synthetic

<400> SEQUENCE: 84

Gly Phe Ser Leu Ser Thr Ser Gly Val Gly
1               5                   10

<210> SEQ ID NO 85
<211> LENGTH: 21
<212> TYPE: DNA
<213> ORGANISM: Artificial Sequence
<220> FEATURE:
<223> OTHER INFORMATION: Synthetic

<400> SEQUENCE: 85
atttattgga atgatgataa g                                             21

<210> SEQ ID NO 86
<211> LENGTH: 7
<212> TYPE: PRT
<213> ORGANISM: Artificial Sequence
<220> FEATURE:
<223> OTHER INFORMATION: Synthetic

<400> SEQUENCE: 86

Ile Tyr Trp Asn Asp Asp Lys
1               5

<210> SEQ ID NO 87
<211> LENGTH: 45

```
<212> TYPE: DNA
<213> ORGANISM: Artificial Sequence
<220> FEATURE:
<223> OTHER INFORMATION: Synthetic

<400> SEQUENCE: 87
acacacacct cccgttataa ctggcactac ggcttccttg actac              45

<210> SEQ ID NO 88
<211> LENGTH: 15
<212> TYPE: PRT
<213> ORGANISM: Artificial Sequence
<220> FEATURE:
<223> OTHER INFORMATION: Synthetic

<400> SEQUENCE: 88

Thr His Thr Ser Arg Tyr Asn Trp His Tyr Gly Phe Leu Asp Tyr
1               5                   10                  15

<210> SEQ ID NO 89
<211> LENGTH: 324
<212> TYPE: DNA
<213> ORGANISM: Artificial Sequence
<220> FEATURE:
<223> OTHER INFORMATION: Synthetic

<400> SEQUENCE: 89
gccatccaga tgacccagtc tccatcctca ctgtctgcat ctgtaggaga cagagtcacc    60
atcacttgtc gggcgagtca gggcattagc aattatttag cctggtttca gcagaaacca   120
gggaaagccc ctaagtccct gatctatgct gcatccagtt tgcaaagtgg ggtcccatca   180
aagttcagcg gcagtggatc tgggacagat ttcactctca ccatcagcag cctgcagcct   240
gaagattttg caacttatta ctgccaacaa tataatagtt acccgctcac tttcggcgga   300
gggaccaagg tggaaatcaa acga                                          324

<210> SEQ ID NO 90
<211> LENGTH: 108
<212> TYPE: PRT
<213> ORGANISM: Artificial Sequence
<220> FEATURE:
<223> OTHER INFORMATION: Synthetic

<400> SEQUENCE: 90

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys Arg
            100                 105

<210> SEQ ID NO 91
<211> LENGTH: 18
<212> TYPE: DNA
```

```
<213> ORGANISM: Artificial Sequence
<220> FEATURE:
<223> OTHER INFORMATION: Synthetic

<400> SEQUENCE: 91
cagggcatta gcaattat                                                    18

<210> SEQ ID NO 92
<211> LENGTH: 6
<212> TYPE: PRT
<213> ORGANISM: Artificial Sequence
<220> FEATURE:
<223> OTHER INFORMATION: Synthetic

<400> SEQUENCE: 92

Gln Gly Ile Ser Asn Tyr
1               5

<210> SEQ ID NO 93
<211> LENGTH: 9
<212> TYPE: DNA
<213> ORGANISM: Artificial Sequence
<220> FEATURE:
<223> OTHER INFORMATION: Synthetic

<400> SEQUENCE: 93 gctgcatcc                                                              9

<210> SEQ ID NO 94
<211> LENGTH: 3
<212> TYPE: PRT
<213> ORGANISM: Artificial Sequence
<220> FEATURE:
<223> OTHER INFORMATION: Synthetic

<400> SEQUENCE: 94

Ala Ala Ser
1

<210> SEQ ID NO 95
<211> LENGTH: 27
<212> TYPE: DNA
<213> ORGANISM: Artificial Sequence
<220> FEATURE:
<223> OTHER INFORMATION: Synthetic

<400> SEQUENCE: 95
caacaatata atagttaccc gctcact                                          27

<210> SEQ ID NO 96
<211> LENGTH: 9
<212> TYPE: PRT
<213> ORGANISM: Artificial Sequence
<220> FEATURE:
<223> OTHER INFORMATION: Synthetic

<400> SEQUENCE: 96

Gln Gln Tyr Asn Ser Tyr Pro Leu Thr
1               5

<210> SEQ ID NO 97
<211> LENGTH: 375
<212> TYPE: DNA
<213> ORGANISM: Artificial Sequence
<220> FEATURE:
<223> OTHER INFORMATION: Synthetic
```

-continued

<400> SEQUENCE: 97

```
gaggtgcagc tggtgcagtt gggcccagga ctggtgaagc cttcggagac cctgtccctc      60
acctgcactg tctctggtgg ctccatcagc aatagtaatt actactgggg ctggatccgc     120
cagccccag ggaaggggct ggagtggatt gggactacct attatagtgg gaccacctac      180
tacaacccgt ccctcaagag tcgagtcacc atatccgtag acacgtccaa gaaccagttc     240
tccctgaagc tgagctctgt gaccgccgca gacacggctg tgtattactg tgcgagagat     300
tattatgata gtagtggtta ttattacaac tggttcgatc cctggggcca gggaaccacg     360
gtcaccgtct cctca                                                      375
```

<210> SEQ ID NO 98
<211> LENGTH: 125
<212> TYPE: PRT
<213> ORGANISM: Artificial Sequence
<220> FEATURE:
<223> OTHER INFORMATION: Synthetic

<400> SEQUENCE: 98

Glu Val Gln Leu Val Gln Leu Gly Pro Gly Leu Val Lys Pro Ser Glu
1               5                   10                  15

Thr Leu Ser Leu Thr Cys Thr Val Ser Gly Gly Ser Ile Ser Asn Ser
            20                  25                  30

Asn Tyr Tyr Trp Gly Trp Ile Arg Gln Pro Pro Gly Lys Gly Leu Glu
        35                  40                  45

Trp Ile Gly Thr Thr Tyr Tyr Ser Gly Thr Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Tyr Tyr Asp Ser Ser Gly Tyr Tyr Tyr Asn Trp Phe
            100                 105                 110

Asp Pro Trp Gly Gln Gly Thr Thr Val Thr Val Ser Ser
        115                 120                 125

<210> SEQ ID NO 99
<211> LENGTH: 30
<212> TYPE: DNA
<213> ORGANISM: Artificial Sequence
<220> FEATURE:
<223> OTHER INFORMATION: Synthetic

<400> SEQUENCE: 99

```
ggtggctcca tcagcaatag taattactac                                       30
```

<210> SEQ ID NO 100
<211> LENGTH: 10
<212> TYPE: PRT
<213> ORGANISM: Artificial Sequence
<220> FEATURE:
<223> OTHER INFORMATION: Synthetic

<400> SEQUENCE: 100

Gly Gly Ser Ile Ser Asn Ser Asn Tyr Tyr
1               5                   10

<210> SEQ ID NO 101
<211> LENGTH: 21
<212> TYPE: DNA

```
<213> ORGANISM: Artificial Sequence
<220> FEATURE:
<223> OTHER INFORMATION: Synthetic

<400> SEQUENCE: 101
acctattata gtgggaccac c                                              21

<210> SEQ ID NO 102
<211> LENGTH: 7
<212> TYPE: PRT
<213> ORGANISM: Artificial Sequence
<220> FEATURE:
<223> OTHER INFORMATION: Synthetic

<400> SEQUENCE: 102

Thr Tyr Tyr Ser Gly Thr Thr
1               5

<210> SEQ ID NO 103
<211> LENGTH: 51
<212> TYPE: DNA
<213> ORGANISM: Artificial Sequence
<220> FEATURE:
<223> OTHER INFORMATION: Synthetic

<400> SEQUENCE: 103
gcgagagatt attatgatag tagtggttat tattacaact ggttcgatcc c              51

<210> SEQ ID NO 104
<211> LENGTH: 17
<212> TYPE: PRT
<213> ORGANISM: Artificial Sequence
<220> FEATURE:
<223> OTHER INFORMATION: Synthetic

<400> SEQUENCE: 104

Ala Arg Asp Tyr Tyr Asp Ser Ser Gly Tyr Tyr Tyr Asn Trp Phe Asp
1               5                   10                  15
Pro

<210> SEQ ID NO 105
<211> LENGTH: 324
<212> TYPE: DNA
<213> ORGANISM: Artificial Sequence
<220> FEATURE:
<223> OTHER INFORMATION: Synthetic

<400> SEQUENCE: 105
gccatccaga tgacccagtc tccatcctcc ctgtctgcat ctgtaggaga cagagtcacc     60
atcacttgcc gggcaagtca ggacattaga aatgatttag ctggtatca gcagaaacca    120 gggaaagccc ctaagcgcct gatctatgct gcatccagtt tgcaaagtgg ggtcccatca   180
aggttcagcg gcagtggatc tgggacagaa ttcagtctca cactcagcag cctgcagcct   240
gaagattttg caacttattt ctgtctacag catcatattt acccgtggac gttcggccaa   300
gggaccaagg tggagatcaa acga                                          324

<210> SEQ ID NO 106
<211> LENGTH: 108
<212> TYPE: PRT
<213> ORGANISM: Artificial Sequence
<220> FEATURE:
<223> OTHER INFORMATION: Synthetic

<400> SEQUENCE: 106
```

```
Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Asp
            20                  25                  30

Leu Gly Trp Tyr Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Ser Leu Thr Leu Ser Ser Leu Gln Pro
65                  70                  75                  80

Glu Asp Phe Ala Thr Tyr Phe Cys Leu Gln His His Ile Tyr Pro Trp
                85                  90                  95

Thr Phe Gly Gln Gly Thr Lys Val Glu Ile Lys Arg
            100                 105
```

<210> SEQ ID NO 107
<211> LENGTH: 18
<212> TYPE: DNA
<213> ORGANISM: Artificial Sequence
<220> FEATURE:
<223> OTHER INFORMATION: Synthetic

<400> SEQUENCE: 107
caggacatta gaaatgat                                              18

<210> SEQ ID NO 108
<211> LENGTH: 6
<212> TYPE: PRT
<213> ORGANISM: Artificial Sequence
<220> FEATURE:
<223> OTHER INFORMATION: Synthetic

<400> SEQUENCE: 108

```
Gln Asp Ile Arg Asn Asp
1               5
```

<210> SEQ ID NO 109
<211> LENGTH: 9
<212> TYPE: DNA
<213> ORGANISM: Artificial Sequence
<220> FEATURE:
<223> OTHER INFORMATION: Synthetic

<400> SEQUENCE: 109 gctgcatcc                                                         9

<210> SEQ ID NO 110
<211> LENGTH: 3
<212> TYPE: PRT
<213> ORGANISM: Artificial Sequence
<220> FEATURE:
<223> OTHER INFORMATION: Synthetic

<400> SEQUENCE: 110

```
Ala Ala Ser
1
```

<210> SEQ ID NO 111
<211> LENGTH: 27
<212> TYPE: DNA
<213> ORGANISM: Artificial Sequence
<220> FEATURE:
<223> OTHER INFORMATION: Synthetic

<400> SEQUENCE: 111
ctacagcatc atatttaccc gtggacg                                              27

<210> SEQ ID NO 112
<211> LENGTH: 9
<212> TYPE: PRT
<213> ORGANISM: Artificial Sequence
<220> FEATURE:
<223> OTHER INFORMATION: Synthetic

<400> SEQUENCE: 112

Leu Gln His His Ile Tyr Pro Trp Thr
1               5

<210> SEQ ID NO 113
<211> LENGTH: 355
<212> TYPE: DNA
<213> ORGANISM: Artificial Sequence
<220> FEATURE:
<223> OTHER INFORMATION: Synthetic

<400> SEQUENCE: 113
caggtgcagc tggtggagtc tgggggaggc gtggtccagc ctggggaggtc cctgagactc        60 tcctgtgcag cctctggatt caccttcagt cgctatggca ttcactgggt ccgccaggct       120
ccaggcaagg ggctggagtg ggtggctgtt atatcttatg atggaagtga tgaatactat       180
gtagactccg tgaagggccg attcagcatc tcccgagaca attccaagaa cacgctttat       240
ctacaaatga acagtctgag gcctgcggac tcggctgttt attactgtgt gaaggagat        300 ctggaacttg gttttgacta ctggggccag ggaaccctgg tcaccgtctc ctcaa            355

<210> SEQ ID NO 114
<211> LENGTH: 118
<212> TYPE: PRT
<213> ORGANISM: Artificial Sequence
<220> FEATURE:
<223> OTHER INFORMATION: Synthetic

<400> SEQUENCE: 114

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Arg Tyr
            20                  25                  30

Gly Ile His Trp Val Arg Gln Ala Pro Gly Lys Gly Leu Glu Trp Val
        35                  40                  45

Ala Val Ile Ser Tyr Asp Gly Ser Asp Glu Tyr Tyr Val Asp Ser Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Pro Ala Asp Ser Ala Val Tyr Tyr Cys
                85                  90                  95

Val Lys Gly Asp Leu Glu Leu Gly Phe Asp Tyr Trp Gly Gln Gly Thr
            100                 105                 110

Leu Val Thr Val Ser Ser
        115

<210> SEQ ID NO 115
<211> LENGTH: 24
<212> TYPE: DNA
<213> ORGANISM: Artificial Sequence
<220> FEATURE:
<223> OTHER INFORMATION: Synthetic

<400> SEQUENCE: 115
ggattcacct tcagtcgcta tggc    24

<210> SEQ ID NO 116
<211> LENGTH: 8
<212> TYPE: PRT
<213> ORGANISM: Artificial Sequence
<220> FEATURE:
<223> OTHER INFORMATION: Synthetic

<400> SEQUENCE: 116

Gly Phe Thr Phe Ser Arg Tyr Gly
1               5

<210> SEQ ID NO 117
<211> LENGTH: 24
<212> TYPE: DNA
<213> ORGANISM: Artificial Sequence
<220> FEATURE:
<223> OTHER INFORMATION: Synthetic

<400> SEQUENCE: 117
atatcttatg atggaagtga tgaa    24

<210> SEQ ID NO 118
<211> LENGTH: 8
<212> TYPE: PRT
<213> ORGANISM: Artificial Sequence
<220> FEATURE:
<223> OTHER INFORMATION: Synthetic

<400> SEQUENCE: 118

Ile Ser Tyr Asp Gly Ser Asp Glu
1               5

<210> SEQ ID NO 119
<211> LENGTH: 33
<212> TYPE: DNA
<213> ORGANISM: Artificial Sequence
<220> FEATURE:
<223> OTHER INFORMATION: Synthetic

<400> SEQUENCE: 119
gtgaaaggag atctggaact tggttttgac tac    33

<210> SEQ ID NO 120
<211> LENGTH: 11
<212> TYPE: PRT
<213> ORGANISM: Artificial Sequence
<220> FEATURE:
<223> OTHER INFORMATION: Synthetic

<400> SEQUENCE: 120

Val Lys Gly Asp Leu Glu Leu Gly Phe Asp Tyr
1               5                   10

<210> SEQ ID NO 121
<211> LENGTH: 337
<212> TYPE: DNA
<213> ORGANISM: Artificial Sequence
<220> FEATURE:
<223> OTHER INFORMATION: Synthetic

<400> SEQUENCE: 121

```
gatattgtga tgactcaggc tgcaccctct atacctgtca ttccaggaga gtcagtatcc      60
atgtcctgca ggtctagtaa gagtctcctg tacagtaatg gacatactta cgtgtattgg    120
tttgtgcaga ggccaggcca gtctcctcag ctcctgatat atcggatgtc caaccttgcc    180
tcaggagtcc cagacaggtt cagtggcagt gggtcaggaa ctgctttcac actgagaatc    240
agtagagtgg aggctgagga tgtgggtgtt tattactgta tgcaaaatct agaatttccg    300
ctcacgttcg gtgctgggac caagctggag ctgaaac                             337
```

```
<210> SEQ ID NO 122
<211> LENGTH: 112
<212> TYPE: PRT
<213> ORGANISM: Artificial Sequence
<220> FEATURE:
<223> OTHER INFORMATION: Synthetic

<400> SEQUENCE: 122
```

```
Asp Ile Val Met Thr Gln Ala Ala Pro Ser Ile Pro Val Ile Pro Gly
1               5                   10                  15

Glu Ser Val Ser Met Ser Cys Arg Ser Ser Lys Ser Leu Leu Tyr Ser
            20                  25                  30

Asn Gly His Thr Tyr Val Tyr Trp Phe Val Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln Asn
                85                  90                  95

Leu Glu Phe Pro Leu Thr Phe Gly Ala Gly Thr Lys Leu Glu Leu Lys
            100                 105                 110
```

```
<210> SEQ ID NO 123
<211> LENGTH: 33
<212> TYPE: DNA
<213> ORGANISM: Artificial Sequence
<220> FEATURE:
<223> OTHER INFORMATION: Synthetic

<400> SEQUENCE: 123
aagagtctcc tgtacagtaa tggacatact tac                                  33
```

```
<210> SEQ ID NO 124
<211> LENGTH: 11
<212> TYPE: PRT
<213> ORGANISM: Artificial Sequence
<220> FEATURE:
<223> OTHER INFORMATION: Synthetic

<400> SEQUENCE: 124
```

```
Lys Ser Leu Leu Tyr Ser Asn Gly His Thr Tyr
1               5                   10
```

```
<210> SEQ ID NO 125
<211> LENGTH: 9
<212> TYPE: DNA
<213> ORGANISM: Artificial Sequence
<220> FEATURE:
<223> OTHER INFORMATION: Synthetic

<400> SEQUENCE: 125
``` cggatgtcc                                                                      9

<210> SEQ ID NO 126
<211> LENGTH: 3
<212> TYPE: PRT
<213> ORGANISM: Artificial Sequence
<220> FEATURE:
<223> OTHER INFORMATION: Synthetic

<400> SEQUENCE: 126

Arg Met Ser
1

<210> SEQ ID NO 127
<211> LENGTH: 27
<212> TYPE: DNA
<213> ORGANISM: Artificial Sequence
<220> FEATURE:
<223> OTHER INFORMATION: Synthetic

<400> SEQUENCE: 127
atgcaaaatc tagaatttcc gctcacg                                                 27

<210> SEQ ID NO 128
<211> LENGTH: 9
<212> TYPE: PRT
<213> ORGANISM: Artificial Sequence
<220> FEATURE:
<223> OTHER INFORMATION: Synthetic

<400> SEQUENCE: 128

Met Gln Asn Leu Glu Phe Pro Leu Thr
1               5

<210> SEQ ID NO 129
<211> LENGTH: 355
<212> TYPE: DNA
<213> ORGANISM: Artificial Sequence
<220> FEATURE:
<223> OTHER INFORMATION: Synthetic

<400> SEQUENCE: 129
caggtgcagc tggtggaggc gggggggaggc gtggtccagc ctggggaggtc cctgagactc      60 tcctgtgcag cctctggatt caccttcagt cgctatggca ttcactgggt ccgccaggct     120
ccaggcaagg ggctggagtg ggtggctgtt atatcttatg atggaactga tgaatactat     180
gcagactccg tgaagggccg attcaccatc tcccgagaca attccaagaa cacgctttat     240
ctacaaatga acagtctgag acctgcggac tcggctgtat attactgtgc gaaaggagat     300
ctggaacttg gttttgacta ctggggccag ggaaccctgg tcaccgtctc ctcaa          355

<210> SEQ ID NO 130
<211> LENGTH: 118
<212> TYPE: PRT
<213> ORGANISM: Artificial Sequence
<220> FEATURE:
<223> OTHER INFORMATION: Synthetic

<400> SEQUENCE: 130

Gln Val Gln Leu Val Glu Ala Gly Gly Gly Val Val Gln Pro Gly Arg
1               5                   10                  15

Ser Leu Arg Leu Ser Cys Ala Ala Ser Gly Phe Thr Phe Ser Arg Tyr
            20                  25                  30

Gly Ile His Trp Val Arg Gln Ala Pro Gly Lys Gly Leu Glu Trp Val

```
                35                  40                  45
Ala Val Ile Ser Tyr Asp Gly Thr Asp Glu Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Ala Asp Ser Ala Val Tyr Tyr Cys
                85                  90                  95

Ala Lys Gly Asp Leu Glu Leu Gly Phe Asp Tyr Trp Gly Gln Gly Thr
            100                 105                 110

Leu Val Thr Val Ser Ser
            115
```

<210> SEQ ID NO 131
<211> LENGTH: 24
<212> TYPE: DNA
<213> ORGANISM: Artificial Sequence
<220> FEATURE:
<223> OTHER INFORMATION: Synthetic

<400> SEQUENCE: 131
ggattcacct tcagtcgcta tggc                                        24

<210> SEQ ID NO 132
<211> LENGTH: 8
<212> TYPE: PRT
<213> ORGANISM: Artificial Sequence
<220> FEATURE:
<223> OTHER INFORMATION: Synthetic

<400> SEQUENCE: 132

```
Gly Phe Thr Phe Ser Arg Tyr Gly
 1               5
```

<210> SEQ ID NO 133
<211> LENGTH: 24
<212> TYPE: DNA
<213> ORGANISM: Artificial Sequence
<220> FEATURE:
<223> OTHER INFORMATION: Synthetic

<400> SEQUENCE: 133
atatcttatg atggaactga tgaa                                        24

<210> SEQ ID NO 134
<211> LENGTH: 8
<212> TYPE: PRT
<213> ORGANISM: Artificial Sequence
<220> FEATURE:
<223> OTHER INFORMATION: Synthetic

<400> SEQUENCE: 134

```
Ile Ser Tyr Asp Gly Thr Asp Glu
 1               5
```

<210> SEQ ID NO 135
<211> LENGTH: 33
<212> TYPE: DNA
<213> ORGANISM: Artificial Sequence
<220> FEATURE:
<223> OTHER INFORMATION: Synthetic

<400> SEQUENCE: 135
gcgaaaggag atctggaact tggttttgac tac                              33

<210> SEQ ID NO 136
<211> LENGTH: 11
<212> TYPE: PRT
<213> ORGANISM: Artificial Sequence
<220> FEATURE:
<223> OTHER INFORMATION: Synthetic

<400> SEQUENCE: 136

Ala Lys Gly Asp Leu Glu Leu Gly Phe Asp Tyr
1               5                   10

<210> SEQ ID NO 137
<211> LENGTH: 322
<212> TYPE: DNA
<213> ORGANISM: Artificial Sequence
<220> FEATURE:
<223> OTHER INFORMATION: Synthetic

<400> SEQUENCE: 137
gccatccggt tgacccagtc tccatcttcc gtgtctgcat ctgtgggaga cagagtcacc    60
atcacttgtc gggcgagtca ggatattagt atttggttag cctggtatca gcagagtcca   120
gggaaagccc ctaaactcct gatcaatgtt gcatcccgtt tgcaaagtgg ggtcccatca   180
aggttcagcg gcagtggatc tgggacagat ttcactctca ccatcaacgg tctgcagcct   240
gaagattttg taacttacta ttgtcaacag gctaacagtt tcccgatcac cttcggccaa   300
gggacacgac tggcgaccaa ac                                             322

<210> SEQ ID NO 138
<211> LENGTH: 107
<212> TYPE: PRT
<213> ORGANISM: Artificial Sequence
<220> FEATURE:
<223> OTHER INFORMATION: Synthetic

<400> SEQUENCE: 138

Ala Ile Arg Leu Thr Gln Ser Pro Ser Ser Val Ser Ala Ser Val Gly
1               5                   10                  15

Asp Arg Val Thr Ile Thr Cys Arg Ala Ser Gln Asp Ile Ser Ile Trp
            20                  25                  30

Leu Ala Trp Tyr Gln Gln Ser Pro Gly Lys Ala Pro Lys Leu Leu Ile
        35                  40                  45

Asn Val Ala Ser Arg Leu Gln Ser Gly Val Pro Ser Arg Phe Ser Gly
    50                  55                  60

Ser Gly Ser Gly Thr Asp Phe Thr Leu Thr Ile Asn Gly Leu Gln Pro
65                  70                  75                  80

Glu Asp Phe Val Thr Tyr Tyr Cys Gln Gln Ala Asn Ser Phe Pro Ile
                85                  90                  95

Thr Phe Gly Gln Gly Thr Arg Leu Ala Thr Lys
            100                 105

<210> SEQ ID NO 139
<211> LENGTH: 18
<212> TYPE: DNA
<213> ORGANISM: Artificial Sequence
<220> FEATURE:
<223> OTHER INFORMATION: Synthetic

<400> SEQUENCE: 139
caggatatta gtatttgg                                                   18

```
<210> SEQ ID NO 140
<211> LENGTH: 6
<212> TYPE: PRT
<213> ORGANISM: Artificial Sequence
<220> FEATURE:
<223> OTHER INFORMATION: Synthetic

<400> SEQUENCE: 140

Gln Asp Ile Ser Ile Trp
1               5

<210> SEQ ID NO 141
<211> LENGTH: 9
<212> TYPE: DNA
<213> ORGANISM: Artificial Sequence
<220> FEATURE:
<223> OTHER INFORMATION: Synthetic

<400> SEQUENCE: 141 gttgcatcc                                                                  9

<210> SEQ ID NO 142
<211> LENGTH: 3
<212> TYPE: PRT
<213> ORGANISM: Artificial Sequence
<220> FEATURE:
<223> OTHER INFORMATION: Synthetic

<400> SEQUENCE: 142

Val Ala Ser
1

<210> SEQ ID NO 143
<211> LENGTH: 27
<212> TYPE: DNA
<213> ORGANISM: Artificial Sequence
<220> FEATURE:
<223> OTHER INFORMATION: Synthetic

<400> SEQUENCE: 143
caacaggcta acagtttccc gatcacc                                             27

<210> SEQ ID NO 144
<211> LENGTH: 9
<212> TYPE: PRT
<213> ORGANISM: Artificial Sequence
<220> FEATURE:
<223> OTHER INFORMATION: Synthetic

<400> SEQUENCE: 144

Gln Gln Ala Asn Ser Phe Pro Ile Thr
1               5

<210> SEQ ID NO 145
<211> LENGTH: 358
<212> TYPE: DNA
<213> ORGANISM: Artificial Sequence
<220> FEATURE:
<223> OTHER INFORMATION: Synthetic

<400> SEQUENCE: 145
caggtgcagc tggtgcagtc tgggggaggc ctggtcaagc ctgggggtc cctgagactc        60 tcctgtgcag cctctggatt catcttcaat acctatacca tgaattgggt ccgccaggct       120
ccagggaagg ggctggagtg gtctctcatcc atcactagtc gtggtactta tatattctac      180
tcagactcac ttaagggccg attcaccatt tccagagaca cgccaataa ctcactgttt        240
```

```
ctgcaaatga acagcctgag agtcgaagac acggctgttt attactgttc gagagatcgt    300
ggatacacct ttggtcctga ctactggggc cagggaaccc tggtcaccgt ctcttcag     358
```

<210> SEQ ID NO 146
<211> LENGTH: 119
<212> TYPE: PRT
<213> ORGANISM: Artificial Sequence
<220> FEATURE:
<223> OTHER INFORMATION: Synthetic

<400> SEQUENCE: 146

```
Gln Val Gln Leu Val Gln Ser Gly Gly Gly Leu Val Lys Pro Gly Gly
  1               5                  10                  15

Ser Leu Arg Leu Ser Cys Ala Ala Ser Gly Phe Ile Phe Asn Thr Tyr
             20                  25                  30

Thr Met Asn Trp Val Arg Gln Ala Pro Gly Lys Gly Leu Glu Trp Val
         35                  40                  45

Ser Ser Ile Thr Ser Arg Gly Thr Tyr Ile Phe Tyr Ser Asp Ser Leu
     50                  55                  60

Lys Gly Arg Phe Thr Ile Ser Arg Asp Asn Ala Asn Asn Ser Leu Phe
 65                  70                  75                  80

Leu Gln Met Asn Ser Leu Arg Val Glu Asp Thr Ala Val Tyr Tyr Cys
                 85                  90                  95

Ser Arg Asp Arg Gly Tyr Thr Phe Gly Pro Asp Tyr Trp Gly Gln Gly
            100                 105                 110

Thr Leu Val Thr Val Ser Ser
        115
```

<210> SEQ ID NO 147
<211> LENGTH: 24
<212> TYPE: DNA
<213> ORGANISM: Artificial Sequence
<220> FEATURE:
<223> OTHER INFORMATION: Synthetic

<400> SEQUENCE: 147

```
ggattcatct tcaataccta tacc                                           24
```

<210> SEQ ID NO 148
<211> LENGTH: 8
<212> TYPE: PRT
<213> ORGANISM: Artificial Sequence
<220> FEATURE:
<223> OTHER INFORMATION: Synthetic

<400> SEQUENCE: 148

```
Gly Phe Ile Phe Asn Thr Tyr Thr
  1               5
```

<210> SEQ ID NO 149
<211> LENGTH: 24
<212> TYPE: DNA
<213> ORGANISM: Artificial Sequence
<220> FEATURE:
<223> OTHER INFORMATION: Synthetic

<400> SEQUENCE: 149

```
atcactagtc gtggtactta tata                                           24
```

<210> SEQ ID NO 150
<211> LENGTH: 8

```
<212> TYPE: PRT
<213> ORGANISM: Artificial Sequence
<220> FEATURE:
<223> OTHER INFORMATION: Synthetic

<400> SEQUENCE: 150

Ile Thr Ser Arg Gly Thr Tyr Ile
1               5

<210> SEQ ID NO 151
<211> LENGTH: 36
<212> TYPE: DNA
<213> ORGANISM: Artificial Sequence
<220> FEATURE:
<223> OTHER INFORMATION: Synthetic

<400> SEQUENCE: 151
tcgagagatc gtggatacac ctttggtcct gactac                                 36

<210> SEQ ID NO 152
<211> LENGTH: 12
<212> TYPE: PRT
<213> ORGANISM: Artificial Sequence
<220> FEATURE:
<223> OTHER INFORMATION: Synthetic

<400> SEQUENCE: 152

Ser Arg Asp Arg Gly Tyr Thr Phe Gly Pro Asp Tyr
1               5                   10

<210> SEQ ID NO 153
<211> LENGTH: 322
<212> TYPE: DNA
<213> ORGANISM: Artificial Sequence
<220> FEATURE:
<223> OTHER INFORMATION: Synthetic

<400> SEQUENCE: 153
gacatccaga tgacccagtc tccatcctcc ctgtctgcat ctgtaggaga cagagtcacc         60
atcacttgcc gggcaagtca ggacattaga aatgatttag ctggtatca  gcagaaacca       120 gggaaagccc ctaagggcct gatctatgct gcatccagtt tgcaaagtgg ggtcccatca       180
aggttcagcg gcagtggatc tgggacagaa ttcactctca caatcagcag cctgcagcct       240
gaagattttg caacttatca ctgtctacat tatgattttc atcctcggac gttcggccaa       300
gggaccaagg tggaaatcaa gc                                                322

<210> SEQ ID NO 154
<211> LENGTH: 107
<212> TYPE: PRT
<213> ORGANISM: Artificial Sequence
<220> FEATURE:
<223> OTHER INFORMATION: Synthetic

<400> SEQUENCE: 154

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Asp
            20                  25                  30

Leu Gly Trp Tyr Gln Gln Lys Pro Gly Lys Ala Pro Lys Gly Leu Ile
        35                  40                  45

Tyr Ala Ala Ser Ser Leu Gln Ser Gly Val Pro Ser Arg Phe Ser Gly
    50                  55                  60
```

Ser Gly Ser Gly Thr Glu Phe Thr Leu Thr Ile Ser Ser Leu Gln Pro
65                  70                  75                  80

Glu Asp Phe Ala Thr Tyr His Cys Leu His Tyr Asp Phe His Pro Arg
                85                  90                  95

Thr Phe Gly Gln Gly Thr Lys Val Glu Ile Lys
            100                 105

<210> SEQ ID NO 155
<211> LENGTH: 18
<212> TYPE: DNA
<213> ORGANISM: Artificial Sequence
<220> FEATURE:
<223> OTHER INFORMATION: Synthetic

<400> SEQUENCE: 155
caggacatta gaaatgat                                                   18

<210> SEQ ID NO 156
<211> LENGTH: 6
<212> TYPE: PRT
<213> ORGANISM: Artificial Sequence
<220> FEATURE:
<223> OTHER INFORMATION: Synthetic

<400> SEQUENCE: 156

Gln Asp Ile Arg Asn Asp
1               5

<210> SEQ ID NO 157
<211> LENGTH: 9
<212> TYPE: DNA
<213> ORGANISM: Artificial Sequence
<220> FEATURE:
<223> OTHER INFORMATION: Synthetic

<400> SEQUENCE: 157 gctgcatcc                                                              9

<210> SEQ ID NO 158
<211> LENGTH: 3
<212> TYPE: PRT
<213> ORGANISM: Artificial Sequence
<220> FEATURE:
<223> OTHER INFORMATION: Synthetic

<400> SEQUENCE: 158

Ala Ala Ser
1

<210> SEQ ID NO 159
<211> LENGTH: 27
<212> TYPE: DNA
<213> ORGANISM: Artificial Sequence
<220> FEATURE:
<223> OTHER INFORMATION: Synthetic

<400> SEQUENCE: 159
ctacattatg attttcatcc tcggacg                                         27

<210> SEQ ID NO 160
<211> LENGTH: 9
<212> TYPE: PRT
<213> ORGANISM: Artificial Sequence
<220> FEATURE:
<223> OTHER INFORMATION: Synthetic

<400> SEQUENCE: 160

Leu His Tyr Asp Phe His Pro Arg Thr
1               5

<210> SEQ ID NO 161
<211> LENGTH: 391
<212> TYPE: DNA
<213> ORGANISM: Artificial Sequence
<220> FEATURE:
<223> OTHER INFORMATION: Synthetic

<400> SEQUENCE: 161
caggtgcaac tggtggagtc tgggggaggc gtggtccagc ctgggaggtc cctgagactc      60
tcctgtgcag cgtctggatt caccttcagt agctatgcca tgcactgggt ccgccaggct     120
ccaggcaagg gctggagtg gtggcagtt atatggtatg atggaactaa ttattactat       180
gcagactccg tgaagggccg attcaccatc tccagagaca attccaagaa cacgctgtat    240
ctgcaaatga acagcctgag agccgaggac acggctgtgt attactgtgc gagagatccc    300
ctatattacg atattttgac tggttattcc cccgactact actacggtat ggacgtctgg    360
ggccaaggga ccacggtcac cgtctcctca g                                    391

<210> SEQ ID NO 162
<211> LENGTH: 130
<212> TYPE: PRT
<213> ORGANISM: Artificial Sequence
<220> FEATURE:
<223> OTHER INFORMATION: Synthetic

<400> SEQUENCE: 162

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Trp Tyr Asp Gly Thr Asn Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Leu Tyr Tyr Asp Ile Leu Thr Gly Tyr Ser Pro Asp
            100                 105                 110

Tyr Tyr Tyr Gly Met Asp Val Trp Gly Gln Gly Thr Thr Val Thr Val
        115                 120                 125

Ser Ser
    130

<210> SEQ ID NO 163
<211> LENGTH: 24
<212> TYPE: DNA
<213> ORGANISM: Artificial Sequence
<220> FEATURE:
<223> OTHER INFORMATION: Synthetic

<400> SEQUENCE: 163
ggattcacct tcagtagcta tgcc                                            24

<210> SEQ ID NO 164
<211> LENGTH: 8
<212> TYPE: PRT
<213> ORGANISM: Artificial Sequence
<220> FEATURE:
<223> OTHER INFORMATION: Synthetic

<400> SEQUENCE: 164

Gly Phe Thr Phe Ser Ser Tyr Ala
1               5

<210> SEQ ID NO 165
<211> LENGTH: 24
<212> TYPE: DNA
<213> ORGANISM: Artificial Sequence
<220> FEATURE:
<223> OTHER INFORMATION: Synthetic

<400> SEQUENCE: 165
atatggtatg atggaactaa ttat                                          24

<210> SEQ ID NO 166
<211> LENGTH: 8
<212> TYPE: PRT
<213> ORGANISM: Artificial Sequence
<220> FEATURE:
<223> OTHER INFORMATION: Synthetic

<400> SEQUENCE: 166

Ile Trp Tyr Asp Gly Thr Asn Tyr
1               5

<210> SEQ ID NO 167
<211> LENGTH: 69
<212> TYPE: DNA
<213> ORGANISM: Artificial Sequence
<220> FEATURE:
<223> OTHER INFORMATION: Synthetic

<400> SEQUENCE: 167
gcgagagatc ccctatatta cgatattttg actggttatt cccccgacta ctactacggt    60
atggacgtc                                                           69

<210> SEQ ID NO 168
<211> LENGTH: 23
<212> TYPE: PRT
<213> ORGANISM: Artificial Sequence
<220> FEATURE:
<223> OTHER INFORMATION: Synthetic

<400> SEQUENCE: 168

Ala Arg Asp Pro Leu Tyr Tyr Asp Ile Leu Thr Gly Tyr Ser Pro Asp
1               5                   10                  15

Tyr Tyr Tyr Gly Met Asp Val
            20

<210> SEQ ID NO 169
<211> LENGTH: 322
<212> TYPE: DNA
<213> ORGANISM: Artificial Sequence
<220> FEATURE:
<223> OTHER INFORMATION: Synthetic

<400> SEQUENCE: 169
gaaatagtga tgacgcagtc tccagccacc ctgtctgtgt ctccagggga aagagccacc    60

```
ctctcctgca gggccagtca gactttttagc agcaacttag cctggtacca gcagaaacct      120
ggccaggctc ccaggctcct catctatggt gcatccacca gggccactgg tatcccagcc      180
aggttcagtg gcagtgggtc tgggacagag ttcactctca ccatcagcag cctgcagtct      240
gaagattttg cagtttatta ctgtcagcag tataataagt ggccgctcac tttcggcgga      300
gggaccaagg tggagatcaa ac                                                322
```

<210> SEQ ID NO 170
<211> LENGTH: 107
<212> TYPE: PRT
<213> ORGANISM: Artificial Sequence
<220> FEATURE:
<223> OTHER INFORMATION: Synthetic

<400> SEQUENCE: 170

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Thr Phe Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Lys Trp Pro Leu
                85                  90                  95

Thr Phe Gly Gly Gly Thr Lys Val Glu Ile Lys
            100                 105
```

<210> SEQ ID NO 171
<211> LENGTH: 18
<212> TYPE: DNA
<213> ORGANISM: Artificial Sequence
<220> FEATURE:
<223> OTHER INFORMATION: Synthetic

<400> SEQUENCE: 171

```
cagacttttta gcagcaac                                                    18
```

<210> SEQ ID NO 172
<211> LENGTH: 6
<212> TYPE: PRT
<213> ORGANISM: Artificial Sequence
<220> FEATURE:
<223> OTHER INFORMATION: Synthetic

<400> SEQUENCE: 172

```
Gln Thr Phe Ser Ser Asn
1               5
```

<210> SEQ ID NO 173
<211> LENGTH: 9
<212> TYPE: DNA
<213> ORGANISM: Artificial Sequence
<220> FEATURE:
<223> OTHER INFORMATION: Synthetic

<400> SEQUENCE: 173

```
ggtgcatcc                                                               9
```

<210> SEQ ID NO 174
<211> LENGTH: 3
<212> TYPE: PRT
<213> ORGANISM: Artificial Sequence
<220> FEATURE:
<223> OTHER INFORMATION: Synthetic

<400> SEQUENCE: 174

Gly Ala Ser
1

<210> SEQ ID NO 175
<211> LENGTH: 27
<212> TYPE: DNA
<213> ORGANISM: Artificial Sequence
<220> FEATURE:
<223> OTHER INFORMATION: Synthetic

<400> SEQUENCE: 175
cagcagtata ataagtggcc gctcact                                          27

<210> SEQ ID NO 176
<211> LENGTH: 9
<212> TYPE: PRT
<213> ORGANISM: Artificial Sequence
<220> FEATURE:
<223> OTHER INFORMATION: Synthetic

<400> SEQUENCE: 176

Gln Gln Tyr Asn Lys Trp Pro Leu Thr
1               5

<210> SEQ ID NO 177
<211> LENGTH: 367
<212> TYPE: DNA
<213> ORGANISM: Artificial Sequence
<220> FEATURE:
<223> OTHER INFORMATION: Synthetic

<400> SEQUENCE: 177
gaggtgcagc tgttggagtc tgggggaggc ttggtccagc ctggggagtc cctgagactc      60
tcctgtgcag cctctggatt cacctttagc agctatgcca tgaactgggt ccgccaggct     120
ccagggaagg ggctgagtg gtctcaact atcagtggta gtggtggtta tatatactac      180
gcagactccg tgaagggccg gttcaccatc tccagagaca attccaagaa cacgctgtat     240
ctgcaaatga acagcctgag agccgaagac acggccgtat atttctgtgc gaaagattcc     300
aggtataact ggaactacgg caattttgac tactggggcc agggaaccct ggtcaccgtc     360
tcctcag                                                              367

<210> SEQ ID NO 178
<211> LENGTH: 122
<212> TYPE: PRT
<213> ORGANISM: Artificial Sequence
<220> FEATURE:
<223> OTHER INFORMATION: Synthetic

<400> SEQUENCE: 178

Glu Val Gln Leu Leu Glu Ser Gly Gly Gly Leu Val Gln Pro Gly Glu
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Gly Ser Gly Gly Tyr Ile Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Phe Cys
                 85                  90                  95

Ala Lys Asp Ser Arg Tyr Asn Trp Asn Tyr Gly Asn Phe Asp Tyr Trp
            100                 105                 110

Gly Gln Gly Thr Leu Val Thr Val Ser Ser
            115                 120

<210> SEQ ID NO 179
<211> LENGTH: 24
<212> TYPE: DNA
<213> ORGANISM: Artificial Sequence
<220> FEATURE:
<223> OTHER INFORMATION: Synthetic

<400> SEQUENCE: 179
ggattcacct ttagcagcta tgcc                                            24

<210> SEQ ID NO 180
<211> LENGTH: 8
<212> TYPE: PRT
<213> ORGANISM: Artificial Sequence
<220> FEATURE:
<223> OTHER INFORMATION: Synthetic

<400> SEQUENCE: 180

Gly Phe Thr Phe Ser Ser Tyr Ala
 1               5

<210> SEQ ID NO 181
<211> LENGTH: 24
<212> TYPE: DNA
<213> ORGANISM: Artificial Sequence
<220> FEATURE:
<223> OTHER INFORMATION: Synthetic

<400> SEQUENCE: 181
atcagtggta gtggtggtta tata                                            24

<210> SEQ ID NO 182
<211> LENGTH: 8
<212> TYPE: PRT
<213> ORGANISM: Artificial Sequence
<220> FEATURE:
<223> OTHER INFORMATION: Synthetic

<400> SEQUENCE: 182

Ile Ser Gly Ser Gly Gly Tyr Ile
 1               5

<210> SEQ ID NO 183
<211> LENGTH: 45
<212> TYPE: DNA
<213> ORGANISM: Artificial Sequence
<220> FEATURE:
<223> OTHER INFORMATION: Synthetic

<400> SEQUENCE: 183
gcgaaagatt ccaggtataa ctggaactac ggcaattttg actac                     45

<210> SEQ ID NO 184
<211> LENGTH: 15
<212> TYPE: PRT
<213> ORGANISM: Artificial Sequence
<220> FEATURE:
<223> OTHER INFORMATION: Synthetic

<400> SEQUENCE: 184

Ala Lys Asp Ser Arg Tyr Asn Trp Asn Tyr Gly Asn Phe Asp Tyr
1               5                   10                  15

<210> SEQ ID NO 185
<211> LENGTH: 322
<212> TYPE: DNA
<213> ORGANISM: Artificial Sequence
<220> FEATURE:
<223> OTHER INFORMATION: Synthetic

<400> SEQUENCE: 185

```
gaaatagtga tgacgcagtc tccagccacc ctgtctgtgt ctccagggga aagagccacc      60
ctctcctgca gggccagtca gaatgttagc agcaacttag cctggaacaa gcagaaacct     120
ggccaggctc ccagactcct catctatgct acatccacca gggccactgg tgtcccagcc     180
aggttcagtg ccagtgggtc tgggacagac ttcgctctca ccatcaacag cctgcagtct     240
gaagattttg cagtttatta ctgtcagcag tataataact ggcctctcac tttcggcgga     300
gggaccaagg tggagatcaa ac                                              322
```

<210> SEQ ID NO 186
<211> LENGTH: 107
<212> TYPE: PRT
<213> ORGANISM: Artificial Sequence
<220> FEATURE:
<223> OTHER INFORMATION: Synthetic

<400> SEQUENCE: 186

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Asn Val Ser Ser Asn
            20                  25                  30

Leu Ala Trp Asn Lys Gln Lys Pro Gly Gln Ala Pro Arg Leu Leu Ile
        35                  40                  45

Tyr Ala Thr Ser Thr Arg Ala Thr Gly Val Pro Ala Arg Phe Ser Ala
    50                  55                  60

Ser Gly Ser Gly Thr Asp Phe Ala Leu Thr Ile Asn Ser Leu Gln Ser
65                  70                  75                  80

Glu Asp Phe Ala Val Tyr Tyr Cys Gln Gln Tyr Asn Asn Trp Pro Leu
                85                  90                  95

Thr Phe Gly Gly Gly Thr Lys Val Glu Ile Lys
            100                 105

<210> SEQ ID NO 187
<211> LENGTH: 18
<212> TYPE: DNA
<213> ORGANISM: Artificial Sequence
<220> FEATURE:
<223> OTHER INFORMATION: Synthetic

<400> SEQUENCE: 187
cagaatgtta gcagcaac                                                    18

<210> SEQ ID NO 188

```
<211> LENGTH: 6
<212> TYPE: PRT
<213> ORGANISM: Artificial Sequence
<220> FEATURE:
<223> OTHER INFORMATION: Synthetic

<400> SEQUENCE: 188

Gln Asn Val Ser Ser Asn
1               5

<210> SEQ ID NO 189
<211> LENGTH: 9
<212> TYPE: DNA
<213> ORGANISM: Artificial Sequence
<220> FEATURE:
<223> OTHER INFORMATION: Synthetic

<400> SEQUENCE: 189 gctacatcc                                                                 9

<210> SEQ ID NO 190
<211> LENGTH: 3
<212> TYPE: PRT
<213> ORGANISM: Artificial Sequence
<220> FEATURE:
<223> OTHER INFORMATION: Synthetic

<400> SEQUENCE: 190

Ala Thr Ser
1

<210> SEQ ID NO 191
<211> LENGTH: 27
<212> TYPE: DNA
<213> ORGANISM: Artificial Sequence
<220> FEATURE:
<223> OTHER INFORMATION: Synthetic

<400> SEQUENCE: 191
cagcagtata ataactggcc tctcact                                             27

<210> SEQ ID NO 192
<211> LENGTH: 9
<212> TYPE: PRT
<213> ORGANISM: Artificial Sequence
<220> FEATURE:
<223> OTHER INFORMATION: Synthetic

<400> SEQUENCE: 192

Gln Gln Tyr Asn Asn Trp Pro Leu Thr
1               5

<210> SEQ ID NO 193
<211> LENGTH: 367
<212> TYPE: DNA
<213> ORGANISM: Artificial Sequence
<220> FEATURE:
<223> OTHER INFORMATION: Synthetic

<400> SEQUENCE: 193
gaggtgcaac tgttggaatc tggggggaggc ttggtacagc ctggggggtc cctgagactc        60
tcctgtgtag cctctcgatt caccttcagc agcaatgcca tgagttgggt ccgccaggct       120
ccagggacgg ggctggagtg ggtctcagct attactggta gtggtagtag gacatactac       180
gcagactccg tgaagggccg gttcaccatc tccagagaca attccaagaa cacggtgtat       240
```

```
ctgcaaatga acagcctgag aggcgaggac acggccgtat attactgtgc gaaagatcaa      300
gggggtacct ggaactacgg agattttgac tactggggcc agggaaccct ggtcaccgtc      360
tcctcag                                                                367
```

<210> SEQ ID NO 194
<211> LENGTH: 122
<212> TYPE: PRT
<213> ORGANISM: Artificial Sequence
<220> FEATURE:
<223> OTHER INFORMATION: Synthetic

<400> SEQUENCE: 194

```
Glu Val Gln Leu Leu Glu Ser Gly Gly Gly Leu Val Gln Pro Gly Gly
1               5                   10                  15

Ser Leu Arg Leu Ser Cys Val Ala Ser Arg Phe Thr Phe Ser Ser Asn
            20                  25                  30

Ala Met Ser Trp Val Arg Gln Ala Pro Gly Thr Gly Leu Glu Trp Val
        35                  40                  45

Ser Ala Ile Thr Gly Ser Gly Ser Arg Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Gly Glu Asp Thr Ala Val Tyr Tyr Cys
                85                  90                  95

Ala Lys Asp Gln Gly Gly Thr Trp Asn Tyr Gly Asp Phe Asp Tyr Trp
            100                 105                 110

Gly Gln Gly Thr Leu Val Thr Val Ser Ser
        115                 120
```

<210> SEQ ID NO 195
<211> LENGTH: 24
<212> TYPE: DNA
<213> ORGANISM: Artificial Sequence
<220> FEATURE:
<223> OTHER INFORMATION: Synthetic

<400> SEQUENCE: 195

```
cgattcacct tcagcagcaa tgcc                                             24
```

<210> SEQ ID NO 196
<211> LENGTH: 8
<212> TYPE: PRT
<213> ORGANISM: Artificial Sequence
<220> FEATURE:
<223> OTHER INFORMATION: Synthetic

<400> SEQUENCE: 196

```
Arg Phe Thr Phe Ser Ser Asn Ala
1               5
```

<210> SEQ ID NO 197
<211> LENGTH: 24
<212> TYPE: DNA
<213> ORGANISM: Artificial Sequence
<220> FEATURE:
<223> OTHER INFORMATION: Synthetic

<400> SEQUENCE: 197

```
attactggta gtggtagtag gaca                                             24
```

<210> SEQ ID NO 198

<210> SEQ ID NO 198
<211> LENGTH: 8
<212> TYPE: PRT
<213> ORGANISM: Artificial Sequence
<220> FEATURE:
<223> OTHER INFORMATION: Synthetic

<400> SEQUENCE: 198

Ile Thr Gly Ser Gly Ser Arg Thr
1               5

<210> SEQ ID NO 199
<211> LENGTH: 45
<212> TYPE: DNA
<213> ORGANISM: Artificial Sequence
<220> FEATURE:
<223> OTHER INFORMATION: Synthetic

<400> SEQUENCE: 199
gcgaaagatc aagggggtac ctggaactac ggagattttg actac          45

<210> SEQ ID NO 200
<211> LENGTH: 15
<212> TYPE: PRT
<213> ORGANISM: Artificial Sequence
<220> FEATURE:
<223> OTHER INFORMATION: Synthetic

<400> SEQUENCE: 200

Ala Lys Asp Gln Gly Gly Thr Trp Asn Tyr Gly Asp Phe Asp Tyr
1               5                   10                  15

<210> SEQ ID NO 201
<211> LENGTH: 322
<212> TYPE: DNA
<213> ORGANISM: Artificial Sequence
<220> FEATURE:
<223> OTHER INFORMATION: Synthetic

<400> SEQUENCE: 201
gaaatagtga tgacgcagtc tccagccacc ctgtctgtgt ctccagggga aagagccacc    60
ctctcctgca gggccagtca gagtgttagc agcaacttag cctggtacca gcagaaacct   120
ggccaggctc ccaggctcct catctatggt gcatccacca gggccactgg tctcccagcc   180
aggttcagtg gcagtgggtc tgggacagac ttcactctca ccatcagcag cctgcagtct   240
gaagattttg cagtttatta ctgtcagcag tataataact ggcctctcac tttcggcgga   300
gggaccaagg tggagatcaa gc                                            322

<210> SEQ ID NO 202
<211> LENGTH: 107
<212> TYPE: PRT
<213> ORGANISM: Artificial Sequence
<220> FEATURE:
<223> OTHER INFORMATION: Synthetic

<400> SEQUENCE: 202

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Leu Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Leu
                85                  90                  95

Thr Phe Gly Gly Gly Thr Lys Val Glu Ile Lys
            100                 105

<210> SEQ ID NO 203
<211> LENGTH: 18
<212> TYPE: DNA
<213> ORGANISM: Artificial Sequence
<220> FEATURE:
<223> OTHER INFORMATION: Synthetic

<400> SEQUENCE: 203
cagagtgtta gcagcaac                                                  18

<210> SEQ ID NO 204
<211> LENGTH: 6
<212> TYPE: PRT
<213> ORGANISM: Artificial Sequence
<220> FEATURE:
<223> OTHER INFORMATION: Synthetic

<400> SEQUENCE: 204

Gln Ser Val Ser Ser Asn
1               5

<210> SEQ ID NO 205
<211> LENGTH: 9
<212> TYPE: DNA
<213> ORGANISM: Artificial Sequence
<220> FEATURE:
<223> OTHER INFORMATION: Synthetic

<400> SEQUENCE: 205 ggtgcatcc                                                            9

<210> SEQ ID NO 206
<211> LENGTH: 3
<212> TYPE: PRT
<213> ORGANISM: Artificial Sequence
<220> FEATURE:
<223> OTHER INFORMATION: Synthetic

<400> SEQUENCE: 206

Gly Ala Ser
1

<210> SEQ ID NO 207
<211> LENGTH: 27
<212> TYPE: DNA
<213> ORGANISM: Artificial Sequence
<220> FEATURE:
<223> OTHER INFORMATION: Synthetic

<400> SEQUENCE: 207
cagcagtata taactggcc tctcact                                         27

<210> SEQ ID NO 208
<211> LENGTH: 9
<212> TYPE: PRT
<213> ORGANISM: Artificial Sequence
<220> FEATURE:
<223> OTHER INFORMATION: Synthetic

<400> SEQUENCE: 208

Gln Gln Tyr Asn Asn Trp Pro Leu Thr
1               5

<210> SEQ ID NO 209
<211> LENGTH: 373
<212> TYPE: DNA
<213> ORGANISM: Artificial Sequence
<220> FEATURE:
<223> OTHER INFORMATION: Synthetic

<400> SEQUENCE: 209

```
caggtgcagc tggtggagtc tgggggagac gtggtccagc ctggagggtc cctgagactc    60
tcctgtacag cctctggatt caccttcagt agttatggca tgcactgggt ccgccaggct   120
ccaggcaggg ggctggagtg ggtggcagtt atatcatttg atggaaaaaa taaatactat   180
gcagactccg tgaagggccg attcaccgtc tccagagaca attccaagaa cacgctgttt   240
ctgcaaatga acagcctgag agctgaggac acggctctat attactgtgc gaaaaggata   300
gcagcaactg gttactacta cttctacggt ttggacgtct ggggccaagg gaccacggtc   360
accgtctcct cag                                                      373
```

<210> SEQ ID NO 210
<211> LENGTH: 124
<212> TYPE: PRT
<213> ORGANISM: Artificial Sequence
<220> FEATURE:
<223> OTHER INFORMATION: Synthetic

<400> SEQUENCE: 210

Gln Val Gln Leu Val Glu Ser Gly Gly Asp Val Val Gln Pro Gly Arg
1               5                   10                  15

Ser Leu Arg Leu Ser Cys Thr Ala Ser Gly Phe Thr Phe Ser Ser Tyr
            20                  25                  30

Gly Met His Trp Val Arg Gln Ala Pro Gly Arg Gly Leu Glu Trp Val
        35                  40                  45

Ala Val Ile Ser Phe Asp Gly Lys Asn Lys Tyr Tyr Ala Asp Ser Val
    50                  55                  60

Lys Gly Arg Phe Thr Val Ser Arg Asp Asn Ser Lys Asn Thr Leu Phe
65                  70                  75                  80

Leu Gln Met Asn Ser Leu Arg Ala Glu Asp Thr Ala Leu Tyr Tyr Cys
                85                  90                  95

Ala Lys Arg Ile Ala Ala Thr Gly Tyr Tyr Tyr Phe Tyr Gly Leu Asp
            100                 105                 110

Val Trp Gly Gln Gly Thr Thr Val Thr Val Ser Ser
        115                 120

<210> SEQ ID NO 211
<211> LENGTH: 24
<212> TYPE: DNA
<213> ORGANISM: Artificial Sequence
<220> FEATURE:
<223> OTHER INFORMATION: Synthetic

<400> SEQUENCE: 211

```
ggattcacct tcagtagtta tggc                                           24
```

<210> SEQ ID NO 212
<211> LENGTH: 8

<212> TYPE: PRT
<213> ORGANISM: Artificial Sequence
<220> FEATURE:
<223> OTHER INFORMATION: Synthetic

<400> SEQUENCE: 212

Gly Phe Thr Phe Ser Ser Tyr Gly
1               5

<210> SEQ ID NO 213
<211> LENGTH: 24
<212> TYPE: DNA
<213> ORGANISM: Artificial Sequence
<220> FEATURE:
<223> OTHER INFORMATION: Synthetic

<400> SEQUENCE: 213
atatcatttg atggaaaaaa taaa                                        24

<210> SEQ ID NO 214
<211> LENGTH: 8
<212> TYPE: PRT
<213> ORGANISM: Artificial Sequence
<220> FEATURE:
<223> OTHER INFORMATION: Synthetic

<400> SEQUENCE: 214

Ile Ser Phe Asp Gly Lys Asn Lys
1               5

<210> SEQ ID NO 215
<211> LENGTH: 51
<212> TYPE: DNA
<213> ORGANISM: Artificial Sequence
<220> FEATURE:
<223> OTHER INFORMATION: Synthetic

<400> SEQUENCE: 215
gcgaaaagga tagcagcaac tggttactac tacttctacg gtttggacgt c          51

<210> SEQ ID NO 216
<211> LENGTH: 17
<212> TYPE: PRT
<213> ORGANISM: Artificial Sequence
<220> FEATURE:
<223> OTHER INFORMATION: Synthetic

<400> SEQUENCE: 216

Ala Lys Arg Ile Ala Ala Thr Gly Tyr Tyr Tyr Phe Tyr Gly Leu Asp
1               5                   10                  15
Val

<210> SEQ ID NO 217
<211> LENGTH: 322
<212> TYPE: DNA
<213> ORGANISM: Artificial Sequence
<220> FEATURE:
<223> OTHER INFORMATION: Synthetic

<400> SEQUENCE: 217
gaaataatga tgacgcagtc tccagccacc ctgtctgtgt ctccagggga aagaggcacc    60
ctctcctgca gggccagtca gagtgttagt agcaacttag cctggtacca gcagaaacct   120
ggccaggctc ccaggctcct catctatggt gcatccacca gggccagtgg tatcccagcc   180
aggttcagtg gcagtgggtc tgggacagag ttcactctca ccgtcagcag cctgcagtct   240

```
gaagattttg cagtttatta ctgtcagcag tataataact ggccgctcac tttcggcgga    300
gggaccaagg tggagatcaa ac                                             322
```

<210> SEQ ID NO 218
<211> LENGTH: 107
<212> TYPE: PRT
<213> ORGANISM: Artificial Sequence
<220> FEATURE:
<223> OTHER INFORMATION: Synthetic

<400> SEQUENCE: 218

```
Glu Ile Met Met Thr Gln Ser Pro Ala Thr Leu Ser Val Ser Pro Gly
1               5                   10                  15

Glu Arg Gly Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Ser Gly Ile Pro Ala Arg Phe Ser Gly
    50                  55                  60

Ser Gly Ser Gly Thr Glu Phe Thr Leu Thr Val Ser Ser Leu Gln Ser
65                  70                  75                  80

Glu Asp Phe Ala Val Tyr Tyr Cys Gln Gln Tyr Asn Asn Trp Pro Leu
                85                  90                  95

Thr Phe Gly Gly Gly Thr Lys Val Glu Ile Lys
            100                 105
```

<210> SEQ ID NO 219
<211> LENGTH: 18
<212> TYPE: DNA
<213> ORGANISM: Artificial Sequence
<220> FEATURE:
<223> OTHER INFORMATION: Synthetic

<400> SEQUENCE: 219

```
cagagtgtta gtagcaac                                                  18
```

<210> SEQ ID NO 220
<211> LENGTH: 6
<212> TYPE: PRT
<213> ORGANISM: Artificial Sequence
<220> FEATURE:
<223> OTHER INFORMATION: Synthetic

<400> SEQUENCE: 220

```
Gln Ser Val Ser Ser Asn
1               5
```

<210> SEQ ID NO 221
<211> LENGTH: 9
<212> TYPE: DNA
<213> ORGANISM: Artificial Sequence
<220> FEATURE:
<223> OTHER INFORMATION: Synthetic

<400> SEQUENCE: 221

```
ggtgcatcc                                                             9
```

<210> SEQ ID NO 222
<211> LENGTH: 3
<212> TYPE: PRT
<213> ORGANISM: Artificial Sequence
<220> FEATURE:

<223> OTHER INFORMATION: Synthetic

<400> SEQUENCE: 222

Gly Ala Ser
1

<210> SEQ ID NO 223
<211> LENGTH: 27
<212> TYPE: DNA
<213> ORGANISM: Artificial Sequence
<220> FEATURE:
<223> OTHER INFORMATION: Synthetic

<400> SEQUENCE: 223
cagcagtata ataactggcc gctcact                                         27

<210> SEQ ID NO 224
<211> LENGTH: 9
<212> TYPE: PRT
<213> ORGANISM: Artificial Sequence
<220> FEATURE:
<223> OTHER INFORMATION: Synthetic

<400> SEQUENCE: 224

Gln Gln Tyr Asn Asn Trp Pro Leu Thr
1               5

<210> SEQ ID NO 225
<211> LENGTH: 367
<212> TYPE: DNA
<213> ORGANISM: Artificial Sequence
<220> FEATURE:
<223> OTHER INFORMATION: Synthetic

<400> SEQUENCE: 225
gaggttcagc tgttggagtc tgggggaggc ttggtacagc cggggggtc cctgagactc       60 tcctgtgcag cctctggatt cacctctatc acctatgcca tgagctgggt ccgccaggct      120
ccagggaagg ggctggagtg ggtctcagct attagtgtta gtggtactaa tacatactac      180
gcagactccg tgaagggccg gttcaccatc tccagagaca gtccaagaa catgctgtat       240 ctgcaaatga acagcctgag agccgaggac acggccgtgt attactgtgc gaaagatctc      300
ctacataact ggaaatacgg gacttttgat atctggggcc aagggacaat ggtcaccgtc      360
tcttcag                                                              367

<210> SEQ ID NO 226
<211> LENGTH: 122
<212> TYPE: PRT
<213> ORGANISM: Artificial Sequence
<220> FEATURE:
<223> OTHER INFORMATION: Synthetic

<400> SEQUENCE: 226

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Ser Ile Thr Tyr
            20                  25                  30

Ala Met Ser Trp Val Arg Gln Ala Pro Gly Lys Gly Leu Glu Trp Val
        35                  40                  45

Ser Ala Ile Ser Val Ser Gly Thr Asn Thr Tyr Tyr Ala Asp Ser Val
    50                  55                  60

Lys Gly Arg Phe Thr Ile Ser Arg Asp Lys Ser Lys Asn Met Leu Tyr

```
                65                  70                  75                  80
Leu Gln Met Asn Ser Leu Arg Ala Glu Asp Thr Ala Val Tyr Tyr Cys
                    85                  90                  95

Ala Lys Asp Leu Leu His Asn Trp Lys Tyr Gly Thr Phe Asp Ile Trp
                100                 105                 110

Gly Gln Gly Thr Met Val Thr Val Ser Ser
            115                 120
```

<210> SEQ ID NO 227
<211> LENGTH: 24
<212> TYPE: DNA
<213> ORGANISM: Artificial Sequence
<220> FEATURE:
<223> OTHER INFORMATION: Synthetic

<400> SEQUENCE: 227
ggattcacct ctatcaccta tgcc                                              24

<210> SEQ ID NO 228
<211> LENGTH: 8
<212> TYPE: PRT
<213> ORGANISM: Artificial Sequence
<220> FEATURE:
<223> OTHER INFORMATION: Synthetic

<400> SEQUENCE: 228

```
Gly Phe Thr Ser Ile Thr Tyr Ala
1               5
```

<210> SEQ ID NO 229
<211> LENGTH: 24
<212> TYPE: DNA
<213> ORGANISM: Artificial Sequence
<220> FEATURE:
<223> OTHER INFORMATION: Synthetic

<400> SEQUENCE: 229
attagtgtta gtggtactaa taca                                              24

<210> SEQ ID NO 230
<211> LENGTH: 8
<212> TYPE: PRT
<213> ORGANISM: Artificial Sequence
<220> FEATURE:
<223> OTHER INFORMATION: Synthetic

<400> SEQUENCE: 230

```
Ile Ser Val Ser Gly Thr Asn Thr
1               5
```

<210> SEQ ID NO 231
<211> LENGTH: 45
<212> TYPE: DNA
<213> ORGANISM: Artificial Sequence
<220> FEATURE:
<223> OTHER INFORMATION: Synthetic

<400> SEQUENCE: 231
gcgaaagatc tcctacataa ctggaaatac gggacttttg atatc                       45

<210> SEQ ID NO 232
<211> LENGTH: 15
<212> TYPE: PRT
<213> ORGANISM: Artificial Sequence
<220> FEATURE:

<223> OTHER INFORMATION: Synthetic

<400> SEQUENCE: 232

Ala Lys Asp Leu Leu His Asn Trp Lys Tyr Gly Thr Phe Asp Ile
1               5                   10                  15

<210> SEQ ID NO 233
<211> LENGTH: 322
<212> TYPE: DNA
<213> ORGANISM: Artificial Sequence
<220> FEATURE:
<223> OTHER INFORMATION: Synthetic

<400> SEQUENCE: 233

```
gaaatagtga tgacgcagtc tccagccacc ctgtctgtgt ctccagggga aagagccacc     60
ctctcctgca gggccagtca gagtgttgac agcaacttag tctggtacca acaaaaacct    120
ggccaggttc ccaggctcct catctatggt gcatccacca gggccactgg tatcccagcc    180
aggttcagtg gcagtgggtc tgggacagag ttcactctca ccatcagcag cctgcagtct    240
gaagattttg cagtttatta ctgtcagcag tataataagt ggccgctcac tttcggcgga    300
gggaccaagg tggagatcaa ac                                             322
```

<210> SEQ ID NO 234
<211> LENGTH: 107
<212> TYPE: PRT
<213> ORGANISM: Artificial Sequence
<220> FEATURE:
<223> OTHER INFORMATION: Synthetic

<400> SEQUENCE: 234

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Asp Ser Asn
                20                  25                  30

Leu Val Trp Tyr Gln Gln Lys Pro Gly Gln Val Pro Arg Leu Leu Ile
            35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Lys Trp Pro Leu
                85                  90                  95

Thr Phe Gly Gly Gly Thr Lys Val Glu Ile Lys
            100                 105

<210> SEQ ID NO 235
<211> LENGTH: 18
<212> TYPE: DNA
<213> ORGANISM: Artificial Sequence
<220> FEATURE:
<223> OTHER INFORMATION: Synthetic

<400> SEQUENCE: 235
cagagtgttg acagcaac                                                   18

<210> SEQ ID NO 236
<211> LENGTH: 6
<212> TYPE: PRT
<213> ORGANISM: Artificial Sequence
<220> FEATURE:
<223> OTHER INFORMATION: Synthetic

<400> SEQUENCE: 236

Gln Ser Val Asp Ser Asn
1               5

<210> SEQ ID NO 237
<211> LENGTH: 9
<212> TYPE: DNA
<213> ORGANISM: Artificial Sequence
<220> FEATURE:
<223> OTHER INFORMATION: Synthetic

<400> SEQUENCE: 237 ggtgcatcc                                                              9

<210> SEQ ID NO 238
<211> LENGTH: 3
<212> TYPE: PRT
<213> ORGANISM: Artificial Sequence
<220> FEATURE:
<223> OTHER INFORMATION: Synthetic

<400> SEQUENCE: 238

Gly Ala Ser
1

<210> SEQ ID NO 239
<211> LENGTH: 27
<212> TYPE: DNA
<213> ORGANISM: Artificial Sequence
<220> FEATURE:
<223> OTHER INFORMATION: Synthetic

<400> SEQUENCE: 239
cagcagtata ataagtggcc gctcact                                         27

<210> SEQ ID NO 240
<211> LENGTH: 9
<212> TYPE: PRT
<213> ORGANISM: Artificial Sequence
<220> FEATURE:
<223> OTHER INFORMATION: Synthetic

<400> SEQUENCE: 240

Gln Gln Tyr Asn Lys Trp Pro Leu Thr
1               5

<210> SEQ ID NO 241
<211> LENGTH: 367
<212> TYPE: DNA
<213> ORGANISM: Artificial Sequence
<220> FEATURE:
<223> OTHER INFORMATION: Synthetic

<400> SEQUENCE: 241
gaggttcagc tgttggagtc tgggggaggc ttggtacagc cggggggtc cctgagactc      60 tcctgtgcag cctctggatt cacctctatc acctatgcca tgagctgggt ccgccaggct    120
ccagggaagg ggctggagtg ggtctcagct attagtgtta gtggtactaa tacatactac    180
gcagactccg tgaagggccg gttcaccatc tccagagaca agtccaagaa catgctgtat    240
ctgcaaatga acagcctgag agccgaggac acggccgtgt attactgtgc gaaagatctc    300
ctacataact ggaaatacgg gactttgat atctggggcc aagggacaat ggtcaccgtc    360
tcttcag                                                             367

<210> SEQ ID NO 242
<211> LENGTH: 122
<212> TYPE: PRT
<213> ORGANISM: Artificial Sequence
<220> FEATURE:
<223> OTHER INFORMATION: Synthetic

<400> SEQUENCE: 242

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Ser Ile Thr Tyr
            20                  25                  30

Ala Met Ser Trp Val Arg Gln Ala Pro Gly Lys Gly Leu Glu Trp Val
        35                  40                  45

Ser Ala Ile Ser Val Ser Gly Thr Asn Thr Tyr Tyr Ala Asp Ser Val
    50                  55                  60

Lys Gly Arg Phe Thr Ile Ser Arg Asp Lys Ser Lys Asn Met Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Leu His Asn Trp Lys Tyr Gly Thr Phe Asp Ile Trp
            100                 105                 110

Gly Gln Gly Thr Met Val Thr Val Ser Ser
        115                 120

<210> SEQ ID NO 243
<211> LENGTH: 24
<212> TYPE: DNA
<213> ORGANISM: Artificial Sequence
<220> FEATURE:
<223> OTHER INFORMATION: Synthetic

<400> SEQUENCE: 243
ggattcacct ctatcaccta tgcc                                          24

<210> SEQ ID NO 244
<211> LENGTH: 8
<212> TYPE: PRT
<213> ORGANISM: Artificial Sequence
<220> FEATURE:
<223> OTHER INFORMATION: Synthetic

<400> SEQUENCE: 244

Gly Phe Thr Ser Ile Thr Tyr Ala
1               5

<210> SEQ ID NO 245
<211> LENGTH: 24
<212> TYPE: DNA
<213> ORGANISM: Artificial Sequence
<220> FEATURE:
<223> OTHER INFORMATION: Synthetic

<400> SEQUENCE: 245
attagtgtta gtggtactaa taca                                          24

<210> SEQ ID NO 246
<211> LENGTH: 8
<212> TYPE: PRT
<213> ORGANISM: Artificial Sequence
<220> FEATURE:
<223> OTHER INFORMATION: Synthetic -continued

<400> SEQUENCE: 246

Ile Ser Val Ser Gly Thr Asn Thr
1               5

<210> SEQ ID NO 247
<211> LENGTH: 45
<212> TYPE: DNA
<213> ORGANISM: Artificial Sequence
<220> FEATURE:
<223> OTHER INFORMATION: Synthetic

<400> SEQUENCE: 247
gcgaaagatc tcctacataa ctggaaatac gggacttttg atatc                45

<210> SEQ ID NO 248
<211> LENGTH: 15
<212> TYPE: PRT
<213> ORGANISM: Artificial Sequence
<220> FEATURE:
<223> OTHER INFORMATION: Synthetic

<400> SEQUENCE: 248

Ala Lys Asp Leu Leu His Asn Trp Lys Tyr Gly Thr Phe Asp Ile
1               5                   10                  15

<210> SEQ ID NO 249
<211> LENGTH: 325
<212> TYPE: DNA
<213> ORGANISM: Artificial Sequence
<220> FEATURE:
<223> OTHER INFORMATION: Synthetic

<400> SEQUENCE: 249
gaaatagtga tgacgcagtc tccagccacc ctgtctgtgt ctccagggga aagagccacc      60
ctctcctgca gggccagtca gagtgttagc agcaacttag cctggaacca gcagaaacct     120
ggccaggctc ccaggctcct catctatggt gcatccacca gggccacggg tatcccagcc     180
aggttcagtg gcagtgggtc tgggacagag ttcactctca ccatcagcag cctgcagtct     240
gaagattttg cagtttatta ctgtcagcag tataacaact ggcccatgta cacttttggc     300
caggggacca agctggagat caaac                                          325

<210> SEQ ID NO 250
<211> LENGTH: 108
<212> TYPE: PRT
<213> ORGANISM: Artificial Sequence
<220> FEATURE:
<223> OTHER INFORMATION: Synthetic

<400> SEQUENCE: 250

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Asn Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Met 85                  90                  95

Tyr Thr Phe Gly Gln Gly Thr Lys Leu Glu Ile Lys
            100                 105

<210> SEQ ID NO 251
<211> LENGTH: 18
<212> TYPE: DNA
<213> ORGANISM: Artificial Sequence
<220> FEATURE:
<223> OTHER INFORMATION: Synthetic

<400> SEQUENCE: 251
cagagtgtta gcagcaac                                                 18

<210> SEQ ID NO 252
<211> LENGTH: 6
<212> TYPE: PRT
<213> ORGANISM: Artificial Sequence
<220> FEATURE:
<223> OTHER INFORMATION: Synthetic

<400> SEQUENCE: 252

Gln Ser Val Ser Ser Asn
1               5

<210> SEQ ID NO 253
<211> LENGTH: 9
<212> TYPE: DNA
<213> ORGANISM: Artificial Sequence
<220> FEATURE:
<223> OTHER INFORMATION: Synthetic

<400> SEQUENCE: 253 ggtgcatcc                                                            9

<210> SEQ ID NO 254
<211> LENGTH: 3
<212> TYPE: PRT
<213> ORGANISM: Artificial Sequence
<220> FEATURE:
<223> OTHER INFORMATION: Synthetic

<400> SEQUENCE: 254

Gly Ala Ser
1

<210> SEQ ID NO 255
<211> LENGTH: 30
<212> TYPE: DNA
<213> ORGANISM: Artificial Sequence
<220> FEATURE:
<223> OTHER INFORMATION: Synthetic

<400> SEQUENCE: 255
cagcagtata acaactggcc catgtacact                                     30

<210> SEQ ID NO 256
<211> LENGTH: 10
<212> TYPE: PRT
<213> ORGANISM: Artificial Sequence
<220> FEATURE:
<223> OTHER INFORMATION: Synthetic

<400> SEQUENCE: 256

Gln Gln Tyr Asn Asn Trp Pro Met Tyr Thr
1               5                   10

<210> SEQ ID NO 257
<211> LENGTH: 361
<212> TYPE: DNA
<213> ORGANISM: Artificial Sequence
<220> FEATURE:
<223> OTHER INFORMATION: Synthetic

<400> SEQUENCE: 257

```
caggtgcagc tggtggagtc tgggggaggc gtggtccagc ctggggaggtc cctgagactc    60
tcctgtgaag cctctggatt caccttcagt agttctggca tgcactgggt ccgccaggct   120
ccaggcaagg ggctgcagtg gtggctgtt atatcatatg atggaaataa taaatttat    180
gaagactccg tgaagggccg attgaccatt ccagagaca attccaacaa cactctgtgg   240
ctgcaaatga acagcctgag agttgaagac acggctgttt attactgtgc gaaatcagga   300
ggtagagtgg gagccgcctt tgcctactgg ggccagggaa ccctggtcac cgtctcctca   360
g                                                                   361
```

<210> SEQ ID NO 258
<211> LENGTH: 120
<212> TYPE: PRT
<213> ORGANISM: Artificial Sequence
<220> FEATURE:
<223> OTHER INFORMATION: Synthetic

<400> SEQUENCE: 258

```
Gln Val Gln Leu Val Glu Ser Gly Gly Gly Val Val Gln Pro Gly Arg
1               5                   10                  15

Ser Leu Arg Leu Ser Cys Glu Ala Ser Gly Phe Thr Phe Ser Ser Ser
            20                  25                  30

Gly Met His Trp Val Arg Gln Ala Pro Gly Lys Gly Leu Gln Trp Val
        35                  40                  45

Ala Val Ile Ser Tyr Asp Gly Asn Asn Lys Phe Tyr Glu Asp Ser Val
    50                  55                  60

Lys Gly Arg Leu Thr Ile Ser Arg Asp Asn Ser Asn Asn Thr Leu Trp
65                  70                  75                  80

Leu Gln Met Asn Ser Leu Arg Val Glu Asp Thr Ala Val Tyr Tyr Cys
                85                  90                  95

Ala Lys Ser Gly Gly Arg Val Gly Ala Ala Phe Ala Tyr Trp Gly Gln
            100                 105                 110

Gly Thr Leu Val Thr Val Ser Ser
        115                 120
```

<210> SEQ ID NO 259
<211> LENGTH: 24
<212> TYPE: DNA
<213> ORGANISM: Artificial Sequence
<220> FEATURE:
<223> OTHER INFORMATION: Synthetic

<400> SEQUENCE: 259

```
ggattcacct tcagtagttc tggc                                           24
```

<210> SEQ ID NO 260
<211> LENGTH: 8
<212> TYPE: PRT
<213> ORGANISM: Artificial Sequence
<220> FEATURE:
<223> OTHER INFORMATION: Synthetic

<400> SEQUENCE: 260

Gly Phe Thr Phe Ser Ser Ser Gly
1               5

<210> SEQ ID NO 261
<211> LENGTH: 24
<212> TYPE: DNA
<213> ORGANISM: Artificial Sequence
<220> FEATURE:
<223> OTHER INFORMATION: Synthetic

<400> SEQUENCE: 261
atatcatatg atggaaataa taaa                                          24

<210> SEQ ID NO 262
<211> LENGTH: 8
<212> TYPE: PRT
<213> ORGANISM: Artificial Sequence
<220> FEATURE:
<223> OTHER INFORMATION: Synthetic

<400> SEQUENCE: 262

Ile Ser Tyr Asp Gly Asn Asn Lys
1               5

<210> SEQ ID NO 263
<211> LENGTH: 39
<212> TYPE: DNA
<213> ORGANISM: Artificial Sequence
<220> FEATURE:
<223> OTHER INFORMATION: Synthetic

<400> SEQUENCE: 263
gcgaaatcag gaggtagagt gggagccgcc tttgcctac                          39

<210> SEQ ID NO 264
<211> LENGTH: 13
<212> TYPE: PRT
<213> ORGANISM: Artificial Sequence
<220> FEATURE:
<223> OTHER INFORMATION: Synthetic

<400> SEQUENCE: 264

Ala Lys Ser Gly Gly Arg Val Gly Ala Ala Phe Ala Tyr
1               5                   10

<210> SEQ ID NO 265
<211> LENGTH: 337
<212> TYPE: DNA
<213> ORGANISM: Artificial Sequence
<220> FEATURE:
<223> OTHER INFORMATION: Synthetic

<400> SEQUENCE: 265
gatattgtga acactcagtc tccactctct ctgcccgtca cccctggaga gccggcctcc    60
atctcctgca ggtctagtca gagcctcctg tatggtaatg gatacaacta tttggattgg   120
tacctgcaga agccagggca ctctccacag ctcctgatct atttgggttc taatcggggc   180
tccggggtcc ctgacaggtt cagtggcagt ggatcaggca cagattttac actgaagatc   240
agcagagtgg aggctgaaga tgttggcatt tattactgca tgcaaactct acaaactcca   300
ttcactttcg gccctgggac caaaatgtat atcaaac                            337

<210> SEQ ID NO 266

```
<211> LENGTH: 112
<212> TYPE: PRT
<213> ORGANISM: Artificial Sequence
<220> FEATURE:
<223> OTHER INFORMATION: Synthetic

<400> SEQUENCE: 266

Asp Ile Val Asn Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Gly
            20                  25                  30

Asn Gly Tyr Asn Tyr Leu Asp Trp Tyr Leu Gln Lys Pro Gly His Ser
        35                  40                  45

Pro Gln Leu Leu Ile Tyr Leu Gly Ser Asn Arg Gly Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Thr
                85                  90                  95

Leu Gln Thr Pro Phe Thr Phe Gly Pro Gly Thr Lys Met Tyr Ile Lys
            100                 105                 110

<210> SEQ ID NO 267
<211> LENGTH: 33
<212> TYPE: DNA
<213> ORGANISM: Artificial Sequence
<220> FEATURE:
<223> OTHER INFORMATION: Synthetic

<400> SEQUENCE: 267
cagagcctcc tgtatggtaa tggatacaac tat                            33

<210> SEQ ID NO 268
<211> LENGTH: 11
<212> TYPE: PRT
<213> ORGANISM: Artificial Sequence
<220> FEATURE:
<223> OTHER INFORMATION: Synthetic

<400> SEQUENCE: 268

Gln Ser Leu Leu Tyr Gly Asn Gly Tyr Asn Tyr
1               5                   10

<210> SEQ ID NO 269
<211> LENGTH: 9
<212> TYPE: DNA
<213> ORGANISM: Artificial Sequence
<220> FEATURE:
<223> OTHER INFORMATION: Synthetic

<400> SEQUENCE: 269 ttgggttct                                                       9

<210> SEQ ID NO 270
<211> LENGTH: 3
<212> TYPE: PRT
<213> ORGANISM: Artificial Sequence
<220> FEATURE:
<223> OTHER INFORMATION: Synthetic

<400> SEQUENCE: 270

Leu Gly Ser
1
```

<210> SEQ ID NO 271
<211> LENGTH: 27
<212> TYPE: DNA
<213> ORGANISM: Artificial Sequence
<220> FEATURE:
<223> OTHER INFORMATION: Synthetic

<400> SEQUENCE: 271
atgcaaactc tacaaactcc attcact                                           27

<210> SEQ ID NO 272
<211> LENGTH: 9
<212> TYPE: PRT
<213> ORGANISM: Artificial Sequence
<220> FEATURE:
<223> OTHER INFORMATION: Synthetic

<400> SEQUENCE: 272

Met Gln Thr Leu Gln Thr Pro Phe Thr
1               5

<210> SEQ ID NO 273
<211> LENGTH: 376
<212> TYPE: DNA
<213> ORGANISM: Artificial Sequence
<220> FEATURE:
<223> OTHER INFORMATION: Synthetic

<400> SEQUENCE: 273
gaggtgcagc tgttggagtc tgggggaggc ttggtacagc ctggggggtc cctgagactc        60
tcctgtgcag gctctggaat cacctttagc agctatgcca tgagctgggt ccgccaggct       120
ccagggaagg ggctggagtg ggtctcagct attagtggta atggtggtac cacaaactac       180
gcagactccg tgaagggccg gttcaccatc tccagagaca actccaagaa cacgctgtat       240
ctgcaaatga acagcctgag agccgaggac acggccgtat attactgtgc gaaagaaaga       300
atccttacca gcagctggac gaggtacggt attatggacg tctggggcca agggaccacg       360
gtcaccgtct cctcag                                                      376

<210> SEQ ID NO 274
<211> LENGTH: 125
<212> TYPE: PRT
<213> ORGANISM: Artificial Sequence
<220> FEATURE:
<223> OTHER INFORMATION: Synthetic

<400> SEQUENCE: 274

Glu Val Gln Leu Leu Glu Ser Gly Gly Gly Leu Val Gln Pro Gly Gly
1               5                   10                  15

Ser Leu Arg Leu Ser Cys Ala Gly Ser Gly Ile Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Asn Gly Gly Thr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Arg Ile Leu Thr Ser Ser Trp Thr Arg Tyr Gly Ile Met
            100                 105                 110

Asp Val Trp Gly Gln Gly Thr Thr Val Thr Val Ser Ser
        115                 120                 125

<210> SEQ ID NO 275
<211> LENGTH: 24
<212> TYPE: DNA
<213> ORGANISM: Artificial Sequence
<220> FEATURE:
<223> OTHER INFORMATION: Synthetic

<400> SEQUENCE: 275
ggaatcacct ttagcagcta tgcc                                           24

<210> SEQ ID NO 276
<211> LENGTH: 8
<212> TYPE: PRT
<213> ORGANISM: Artificial Sequence
<220> FEATURE:
<223> OTHER INFORMATION: Synthetic

<400> SEQUENCE: 276

Gly Ile Thr Phe Ser Ser Tyr Ala
1               5

<210> SEQ ID NO 277
<211> LENGTH: 24
<212> TYPE: DNA
<213> ORGANISM: Artificial Sequence
<220> FEATURE:
<223> OTHER INFORMATION: Synthetic

<400> SEQUENCE: 277
attagtggta atggtggtac caca                                           24

<210> SEQ ID NO 278
<211> LENGTH: 8
<212> TYPE: PRT
<213> ORGANISM: Artificial Sequence
<220> FEATURE:
<223> OTHER INFORMATION: Synthetic

<400> SEQUENCE: 278

Ile Ser Gly Asn Gly Gly Thr Thr
1               5

<210> SEQ ID NO 279
<211> LENGTH: 54
<212> TYPE: DNA
<213> ORGANISM: Artificial Sequence
<220> FEATURE:
<223> OTHER INFORMATION: Synthetic

<400> SEQUENCE: 279
gcgaaagaaa gaatccttac cagcagctgg acgaggtacg gtattatgga cgtc          54

<210> SEQ ID NO 280
<211> LENGTH: 18
<212> TYPE: PRT
<213> ORGANISM: Artificial Sequence
<220> FEATURE:
<223> OTHER INFORMATION: Synthetic

<400> SEQUENCE: 280

Ala Lys Glu Arg Ile Leu Thr Ser Ser Trp Thr Arg Tyr Gly Ile Met
1               5                   10                  15

Asp Val

<210> SEQ ID NO 281
<211> LENGTH: 322
<212> TYPE: DNA
<213> ORGANISM: Artificial Sequence
<220> FEATURE:
<223> OTHER INFORMATION: Synthetic

<400> SEQUENCE: 281

```
gaaatagtga tgacgcagtc tccagccacc ctgtctatgt ctccagggga aagagccacc    60
ctctcctgca gggccagtca gagtgttagc agcaacttag cctggtacca gcagaaacct   120
ggccaggctc ccaggctcct catctatggt gcatccacca gggccactgg tatcccagcc   180
aggttcagtg gcagtgggtc tgggacagag ttcactctca ccatcagcag cctgcagtct   240
gaagattttg cagtttatta ctgtcagcag tataataact ggcctctcac tttcggcgga   300
gggaccaagt tagagatcaa ac                                             322
```

<210> SEQ ID NO 282
<211> LENGTH: 107
<212> TYPE: PRT
<213> ORGANISM: Artificial Sequence
<220> FEATURE:
<223> OTHER INFORMATION: Synthetic

<400> SEQUENCE: 282

```
Glu Ile Val Met Thr Gln Ser Pro Ala Thr Leu Ser Met Ser Pro Gly
1               5                   10                  15
Glu Arg Ala Thr Leu Ser Cys Arg Ala Ser Gln Ser Val Ser Ser Asn
            20                  25                  30
Leu Ala Trp Tyr Gln Gln Lys Pro Gly Gln Ala Pro Arg Leu Leu Ile
        35                  40                  45
Tyr Gly Ala Ser Thr Arg Ala Thr Gly Ile Pro Ala Arg Phe Ser Gly
    50                  55                  60
Ser Gly Ser Gly Thr Glu Phe Thr Leu Thr Ile Ser Ser Leu Gln Ser
65                  70                  75                  80
Glu Asp Phe Ala Val Tyr Tyr Cys Gln Gln Tyr Asn Asn Trp Pro Leu
                85                  90                  95
Thr Phe Gly Gly Gly Thr Lys Leu Glu Ile Lys
            100                 105
```

<210> SEQ ID NO 283
<211> LENGTH: 18
<212> TYPE: DNA
<213> ORGANISM: Artificial Sequence
<220> FEATURE:
<223> OTHER INFORMATION: Synthetic

<400> SEQUENCE: 283

```
cagagtgtta gcagcaac                                                   18
```

<210> SEQ ID NO 284
<211> LENGTH: 6
<212> TYPE: PRT
<213> ORGANISM: Artificial Sequence
<220> FEATURE:
<223> OTHER INFORMATION: Synthetic

<400> SEQUENCE: 284

```
Gln Ser Val Ser Ser Asn
1               5
```

<210> SEQ ID NO 285
<211> LENGTH: 9
<212> TYPE: DNA
<213> ORGANISM: Artificial Sequence
<220> FEATURE:
<223> OTHER INFORMATION: Synthetic

<400> SEQUENCE: 285 ggtgcatcc                                                                 9

<210> SEQ ID NO 286
<211> LENGTH: 3
<212> TYPE: PRT
<213> ORGANISM: Artificial Sequence
<220> FEATURE:
<223> OTHER INFORMATION: Synthetic

<400> SEQUENCE: 286

Gly Ala Ser
1

<210> SEQ ID NO 287
<211> LENGTH: 27
<212> TYPE: DNA
<213> ORGANISM: Artificial Sequence
<220> FEATURE:
<223> OTHER INFORMATION: Synthetic

<400> SEQUENCE: 287
cagcagtata ataactggcc tctcact                                            27

<210> SEQ ID NO 288
<211> LENGTH: 9
<212> TYPE: PRT
<213> ORGANISM: Artificial Sequence
<220> FEATURE:
<223> OTHER INFORMATION: Synthetic

<400> SEQUENCE: 288

Gln Gln Tyr Asn Asn Trp Pro Leu Thr
1               5

<210> SEQ ID NO 289
<211> LENGTH: 358
<212> TYPE: DNA
<213> ORGANISM: Artificial Sequence
<220> FEATURE:
<223> OTHER INFORMATION: Synthetic

<400> SEQUENCE: 289
caggtgcaac tacagcagtg gggcgcagga ctgttgaagc cttcggagac cctgtccctc        60
acctgcgctg tctatggtgg gtccttcagt ggttactact ggagctggat ccgccagccc       120
ccagggaagg ggctggagtg gattggggaa atcaatcata gtggaaacac caactacaac       180
ccgtccctca agagtcgagt caccatatca gtagacacgt ccaagaacca gttctccctg       240
aaactgaact ctgtgaccgc cgcggacacg gctgtgtatt actgtgcgag aagagaggct       300
acagtaactc catactttga ctactggggc cagggaaccc tggtcaccgt ctcctcag        358

<210> SEQ ID NO 290
<211> LENGTH: 119
<212> TYPE: PRT
<213> ORGANISM: Artificial Sequence
<220> FEATURE:

<223> OTHER INFORMATION: Synthetic

<400> SEQUENCE: 290

Gln Val Gln Leu Gln Gln Trp Gly Ala Gly Leu Leu Lys Pro Ser Glu
1               5                   10                  15
Thr Leu Ser Leu Thr Cys Ala Val Tyr Gly Gly Ser Phe Ser Gly Tyr
            20                  25                  30
Tyr Trp Ser Trp Ile Arg Gln Pro Pro Gly Lys Gly Leu Glu Trp Ile
        35                  40                  45
Gly Glu Ile Asn His Ser Gly Asn Thr Asn Tyr Asn Pro Ser Leu Lys
    50                  55                  60
Ser Arg Val Thr Ile Ser Val Asp Thr Ser Lys Asn Gln Phe Ser Leu
65                  70                  75                  80
Lys Leu Asn Ser Val Thr Ala Ala Asp Thr Ala Val Tyr Tyr Cys Ala
                85                  90                  95
Arg Arg Glu Ala Thr Val Thr Pro Tyr Phe Asp Tyr Trp Gly Gln Gly
            100                 105                 110
Thr Leu Val Thr Val Ser Ser
        115

<210> SEQ ID NO 291
<211> LENGTH: 24
<212> TYPE: DNA
<213> ORGANISM: Artificial Sequence
<220> FEATURE:
<223> OTHER INFORMATION: Synthetic

<400> SEQUENCE: 291
ggtgggtcct tcagtggtta ctac                                          24

<210> SEQ ID NO 292
<211> LENGTH: 8
<212> TYPE: PRT
<213> ORGANISM: Artificial Sequence
<220> FEATURE:
<223> OTHER INFORMATION: Synthetic

<400> SEQUENCE: 292

Gly Gly Ser Gly Ser Gly Tyr Tyr
1               5

<210> SEQ ID NO 293
<211> LENGTH: 21
<212> TYPE: DNA
<213> ORGANISM: Artificial Sequence
<220> FEATURE:
<223> OTHER INFORMATION: Synthetic

<400> SEQUENCE: 293
atcaatcata gtggaaacac c                                             21

<210> SEQ ID NO 294
<211> LENGTH: 7
<212> TYPE: PRT
<213> ORGANISM: Artificial Sequence
<220> FEATURE:
<223> OTHER INFORMATION: Synthetic

<400> SEQUENCE: 294

Ile Asn His Ser Gly Asn Thr
1               5

<210> SEQ ID NO 295
<211> LENGTH: 39
<212> TYPE: DNA
<213> ORGANISM: Artificial Sequence
<220> FEATURE:
<223> OTHER INFORMATION: Synthetic

<400> SEQUENCE: 295
gcgagaagag aggctacagt aactccatac tttgactac                         39

<210> SEQ ID NO 296
<211> LENGTH: 13
<212> TYPE: PRT
<213> ORGANISM: Artificial Sequence
<220> FEATURE:
<223> OTHER INFORMATION: Synthetic

<400> SEQUENCE: 296

Ala Arg Arg Glu Ala Thr Val Thr Pro Tyr Phe Asp Tyr
1               5                   10

<210> SEQ ID NO 297
<211> LENGTH: 322
<212> TYPE: DNA
<213> ORGANISM: Artificial Sequence
<220> FEATURE:
<223> OTHER INFORMATION: Synthetic

<400> SEQUENCE: 297
gacatccagt tgacccagtc tccatccttc ctgtctgcat ctgtaggaga cagagtcacc      60
atcacttgct gggccagtca gggcattagc agttatttag cctggtatca gcaaaaacca     120
gggaaagccc ctaagctcct gatctatgct gcatccactt tgcaaagtgg ggtcccatca     180
aggttcagcg gcagtggatc tgggacagaa ttcactctca caatcagcag cctgcagcct     240
gaagattttg caacttatta ctgtcaacag cttaatagtt atccgctcac tttcggcgga     300
gggaccaagg tggagatcaa ac                                              322

<210> SEQ ID NO 298
<211> LENGTH: 107
<212> TYPE: PRT
<213> ORGANISM: Artificial Sequence
<220> FEATURE:
<223> OTHER INFORMATION: Synthetic

<400> SEQUENCE: 298

Asp Ile Gln Leu Thr Gln Ser Pro Ser Phe Leu Ser Ala Ser Val Gly
1               5                   10                  15

Asp Arg Val Thr Ile Thr Cys Trp Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Leu
                85                  90                  95

Thr Phe Gly Gly Gly Thr Lys Val Glu Ile Lys
            100                 105

<210> SEQ ID NO 299

```
<211> LENGTH: 18
<212> TYPE: DNA
<213> ORGANISM: Artificial Sequence
<220> FEATURE:
<223> OTHER INFORMATION: Synthetic

<400> SEQUENCE: 299
cagggcatta gcagttat                                                       18

<210> SEQ ID NO 300
<211> LENGTH: 6
<212> TYPE: PRT
<213> ORGANISM: Artificial Sequence
<220> FEATURE:
<223> OTHER INFORMATION: Synthetic

<400> SEQUENCE: 300

Gln Gly Ile Ser Ser Tyr
1               5

<210> SEQ ID NO 301
<211> LENGTH: 9
<212> TYPE: DNA
<213> ORGANISM: Artificial Sequence
<220> FEATURE:
<223> OTHER INFORMATION: Synthetic

<400> SEQUENCE: 301 gctgcatcc                                                                  9

<210> SEQ ID NO 302
<211> LENGTH: 3
<212> TYPE: PRT
<213> ORGANISM: Artificial Sequence
<220> FEATURE:
<223> OTHER INFORMATION: Synthetic

<400> SEQUENCE: 302

Ala Ala Ser
1

<210> SEQ ID NO 303
<211> LENGTH: 27
<212> TYPE: DNA
<213> ORGANISM: Artificial Sequence
<220> FEATURE:
<223> OTHER INFORMATION: Synthetic

<400> SEQUENCE: 303
caacagctta atagttatcc gctcact                                             27

<210> SEQ ID NO 304
<211> LENGTH: 9
<212> TYPE: PRT
<213> ORGANISM: Artificial Sequence
<220> FEATURE:
<223> OTHER INFORMATION: Synthetic

<400> SEQUENCE: 304

Gln Gln Leu Asn Ser Tyr Pro Leu Thr
1               5

<210> SEQ ID NO 305
<211> LENGTH: 355
<212> TYPE: DNA
<213> ORGANISM: Artificial Sequence
<220> FEATURE:
```

<223> OTHER INFORMATION: Synthetic

<400> SEQUENCE: 305

```
caggtgcagc tggtggagtc tgggggaggc gtggtccagc ctggggaggtc cctgagactc      60
tcctgtgtag tctctggatt caacttcagt aggaatggca tacactgggt ccgccaggct     120
ccaggcaagg ggctggaatg ggtggcagtt atatcatatg atggaagaaa taaattttat     180
gtagagtccg tgaagggccg attcaccatc tccagagaca attccaagaa cacgctgtat     240
ctgcaaatga acagtctgag agttgaggac acggctgtat attactgtgc gaaatcctca     300
attggagggt tttttgaata ctggggccag ggaaccctgg tcaccgtctc ctcag          355
```

<210> SEQ ID NO 306
<211> LENGTH: 118
<212> TYPE: PRT
<213> ORGANISM: Artificial Sequence
<220> FEATURE:
<223> OTHER INFORMATION: Synthetic

<400> SEQUENCE: 306

```
Gln Val Gln Leu Val Glu Ser Gly Gly Gly Val Val Gln Pro Gly Arg
1               5                   10                  15

Ser Leu Arg Leu Ser Cys Val Val Ser Gly Phe Asn Phe Ser Arg Asn
            20                  25                  30

Gly Ile His Trp Val Arg Gln Ala Pro Gly Lys Gly Leu Glu Trp Val
        35                  40                  45

Ala Val Ile Ser Tyr Asp Gly Arg Asn Lys Phe Tyr Val Glu Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Lys Ser Ser Ile Gly Gly Phe Phe Glu Tyr Trp Gly Gln Gly Thr
            100                 105                 110

Leu Val Thr Val Ser Ser
        115
```

<210> SEQ ID NO 307
<211> LENGTH: 24
<212> TYPE: DNA
<213> ORGANISM: Artificial Sequence
<220> FEATURE:
<223> OTHER INFORMATION: Synthetic

<400> SEQUENCE: 307

```
ggattcaact tcagtaggaa tggc                                              24
```

<210> SEQ ID NO 308
<211> LENGTH: 8
<212> TYPE: PRT
<213> ORGANISM: Artificial Sequence
<220> FEATURE:
<223> OTHER INFORMATION: Synthetic

<400> SEQUENCE: 308

```
Gly Phe Asn Phe Ser Arg Asn Gly
1               5
```

<210> SEQ ID NO 309
<211> LENGTH: 24
<212> TYPE: DNA

```
<213> ORGANISM: Artificial Sequence
<220> FEATURE:
<223> OTHER INFORMATION: Synthetic

<400> SEQUENCE: 309
atatcatatg atggaagaaa taaa                                            24

<210> SEQ ID NO 310
<211> LENGTH: 8
<212> TYPE: PRT
<213> ORGANISM: Artificial Sequence
<220> FEATURE:
<223> OTHER INFORMATION: Synthetic

<400> SEQUENCE: 310

Ile Ser Tyr Asp Gly Arg Asn Lys
1               5

<210> SEQ ID NO 311
<211> LENGTH: 33
<212> TYPE: DNA
<213> ORGANISM: Artificial Sequence
<220> FEATURE:
<223> OTHER INFORMATION: Synthetic

<400> SEQUENCE: 311
gcgaaatcct caattggagg gttttttgaa tac                                  33

<210> SEQ ID NO 312
<211> LENGTH: 11
<212> TYPE: PRT
<213> ORGANISM: Artificial Sequence
<220> FEATURE:
<223> OTHER INFORMATION: Synthetic

<400> SEQUENCE: 312

Ala Lys Ser Ser Ile Gly Gly Phe Phe Glu Tyr
1               5                   10

<210> SEQ ID NO 313
<211> LENGTH: 337
<212> TYPE: DNA
<213> ORGANISM: Artificial Sequence
<220> FEATURE:
<223> OTHER INFORMATION: Synthetic

<400> SEQUENCE: 313
gatattgtga tgactcagtc tccactctcc ctgcccgtca ctcctggaga gccggcctcc     60
atctcctgca ggtctagtca gagcctcctg catagtaatg gatacaacta tttggattgg    120
tacctgcaga agccaggaca gtctccacaa ctcatgatct atttgggttc tcatcgggcc    180
tccggggtcc ctgacaggtt cagtggcagt ggatcaggca cagattttac actgaaaatc    240
agcagagtgg aggctgagga tgttggagtc tattactgca ttcaagttca caaactccg     300 atcaccttcg gccaagggac acggctggag attaaac                             337

<210> SEQ ID NO 314
<211> LENGTH: 112
<212> TYPE: PRT
<213> ORGANISM: Artificial Sequence
<220> FEATURE:
<223> OTHER INFORMATION: Synthetic

<400> SEQUENCE: 314

Asp Ile Val Met Thr Gln Ser Pro Leu Ser Leu Pro Val Thr Pro Gly
```

```
            1               5                  10                 15
Glu Pro Ala Ser Ile Ser Cys Arg Ser Ser Gln Ser Leu Leu His Ser
            20                 25                 30

Asn Gly Tyr Asn Tyr Leu Asp Trp Tyr Leu Gln Lys Pro Gly Gln Ser
            35                 40                 45

Pro Gln Leu Met Ile Tyr Leu Gly Ser His Arg Ala Ser Gly Val Pro
    50                 55                 60

Asp Arg Phe Ser Gly Ser Gly Ser Gly Thr Asp Phe Thr Leu Lys Ile
65                  70                 75                  80

Ser Arg Val Glu Ala Glu Asp Val Gly Val Tyr Tyr Cys Ile Gln Val
                85                 90                 95

Gln Gln Thr Pro Ile Thr Phe Gly Gln Gly Thr Arg Leu Glu Ile Lys
            100                105                110
```

<210> SEQ ID NO 315
<211> LENGTH: 33
<212> TYPE: DNA
<213> ORGANISM: Artificial Sequence
<220> FEATURE:
<223> OTHER INFORMATION: Synthetic

<400> SEQUENCE: 315
cagagcctcc tgcatagtaa tggatacaac tat                                33

<210> SEQ ID NO 316
<211> LENGTH: 11
<212> TYPE: PRT
<213> ORGANISM: Artificial Sequence
<220> FEATURE:
<223> OTHER INFORMATION: Synthetic

<400> SEQUENCE: 316

```
Gln Ser Leu Leu His Ser Asn Gly Tyr Asn Tyr
1               5                   10
```

<210> SEQ ID NO 317
<211> LENGTH: 9
<212> TYPE: DNA
<213> ORGANISM: Artificial Sequence
<220> FEATURE:
<223> OTHER INFORMATION: Synthetic

<400> SEQUENCE: 317 ttgggttct                                                            9

<210> SEQ ID NO 318
<211> LENGTH: 3
<212> TYPE: PRT
<213> ORGANISM: Artificial Sequence
<220> FEATURE:
<223> OTHER INFORMATION: Synthetic

<400> SEQUENCE: 318

```
Leu Gly Ser
1
```

<210> SEQ ID NO 319
<211> LENGTH: 27
<212> TYPE: DNA
<213> ORGANISM: Artificial Sequence
<220> FEATURE:
<223> OTHER INFORMATION: Synthetic

<400> SEQUENCE: 319
attcaagttc aacaaactcc gatcacc                                              27

<210> SEQ ID NO 320
<211> LENGTH: 9
<212> TYPE: PRT
<213> ORGANISM: Artificial Sequence
<220> FEATURE:
<223> OTHER INFORMATION: Synthetic

<400> SEQUENCE: 320

Ile Gln Val Gln Gln Thr Pro Ile Thr
1               5

<210> SEQ ID NO 321
<211> LENGTH: 337
<212> TYPE: DNA
<213> ORGANISM: Artificial Sequence
<220> FEATURE:
<223> OTHER INFORMATION: Synthetic

<400> SEQUENCE: 321
gatattgtga tgactcagac tccactctcc tcacctgtca cccttggaca gccggcctcc    60
atctcctgca ggtctagtca agcctcgta cacagtgatg aaacaccta cttgagttgg   120
cttcagcaga ggccaggcca gcctccaaga ctcctaattt acaagatttc taaccggttc   180
tctggggtcc cagacagatt cagtggcagt ggggcaggga cagatttcac actgaaaatc   240
agcagggtgg aagctgagga tgtcggggtt tatttctgca tgcaagctac acaatttccg   300
tacacttttg gccaggggac caagctggag atcaaag                            337

<210> SEQ ID NO 322
<211> LENGTH: 112
<212> TYPE: PRT
<213> ORGANISM: Artificial Sequence
<220> FEATURE:
<223> OTHER INFORMATION: Synthetic

<400> SEQUENCE: 322

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Phe Cys Met Gln Ala
                85                  90                  95

Thr Gln Phe Pro Tyr Thr Phe Gly Gln Gly Thr Lys Leu Glu Ile Lys
            100                 105                 110

<210> SEQ ID NO 323
<211> LENGTH: 33
<212> TYPE: DNA
<213> ORGANISM: Artificial Sequence
<220> FEATURE:
<223> OTHER INFORMATION: Synthetic

<400> SEQUENCE: 323

```
caaagcctcg tacacagtga tggaaacacc tac                                    33

<210> SEQ ID NO 324
<211> LENGTH: 11
<212> TYPE: PRT
<213> ORGANISM: Artificial Sequence
<220> FEATURE:
<223> OTHER INFORMATION: Synthetic

<400> SEQUENCE: 324

Gln Ser Leu Val His Ser Asp Gly Asn Thr Tyr
1               5                   10

<210> SEQ ID NO 325
<211> LENGTH: 9
<212> TYPE: DNA
<213> ORGANISM: Artificial Sequence
<220> FEATURE:
<223> OTHER INFORMATION: Synthetic

<400> SEQUENCE: 325 aagatttct                                                               9

<210> SEQ ID NO 326
<211> LENGTH: 3
<212> TYPE: PRT
<213> ORGANISM: Artificial Sequence
<220> FEATURE:
<223> OTHER INFORMATION: Synthetic

<400> SEQUENCE: 326

Lys Ile Ser
1

<210> SEQ ID NO 327
<211> LENGTH: 27
<212> TYPE: DNA
<213> ORGANISM: Artificial Sequence
<220> FEATURE:
<223> OTHER INFORMATION: Synthetic

<400> SEQUENCE: 327
atgcaagcta cacaatttcc gtacact                                           27

<210> SEQ ID NO 328
<211> LENGTH: 9
<212> TYPE: PRT
<213> ORGANISM: Artificial Sequence
<220> FEATURE:
<223> OTHER INFORMATION: Synthetic

<400> SEQUENCE: 328

Met Gln Ala Thr Gln Phe Pro Tyr Thr
1               5

<210> SEQ ID NO 329
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Gly
<220> FEATURE:
<221> NAME/KEY: VARIANT
<222> LOCATION: (2)...(2)
```

```
<223> OTHER INFORMATION: Xaa = Phe
<220> FEATURE:
<221> NAME/KEY: VARIANT
<222> LOCATION: (3)...(3)
<223> OTHER INFORMATION: Xaa = Thr
<220> FEATURE:
<221> NAME/KEY: VARIANT
<222> LOCATION: (4)...(4)
<223> OTHER INFORMATION: Xaa = Phe
<220> FEATURE:
<221> NAME/KEY: VARIANT
<222> LOCATION: (5)...(5)
<223> OTHER INFORMATION: Xaa = Ser
<220> FEATURE:
<221> NAME/KEY: VARIANT
<222> LOCATION: (6)...(6)
<223> OTHER INFORMATION: Xaa = Ala or Ser
<220> FEATURE:
<221> NAME/KEY: VARIANT
<222> LOCATION: (7)...(7)
<223> OTHER INFORMATION: Xaa = Phe or Tyr
<220> FEATURE:
<221> NAME/KEY: VARIANT
<222> LOCATION: (8)...(8)
<223> OTHER INFORMATION: Xaa = Gly or Ala

<400> SEQUENCE: 329

Xaa Xaa Xaa Xaa Xaa Xaa Xaa Xaa
1               5

<210> SEQ ID NO 330
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Ile
<220> FEATURE:
<221> NAME/KEY: VARIANT
<222> LOCATION: (2)...(2)
<223> OTHER INFORMATION: Xaa = Gly or Ser
<220> FEATURE:
<221> NAME/KEY: VARIANT
<222> LOCATION: (3)...(3)
<223> OTHER INFORMATION: Xaa = Tyr or Gly
<220> FEATURE:
<221> NAME/KEY: VARIANT
<222> LOCATION: (4)...(4)
<223> OTHER INFORMATION: Xaa = Ser or Asp
<220> FEATURE:
<221> NAME/KEY: VARIANT
<222> LOCATION: (5)...(5)
<223> OTHER INFORMATION: Xaa = Gly
<220> FEATURE:
<221> NAME/KEY: VARIANT
<222> LOCATION: (6)...(6)
<223> OTHER INFORMATION: Xaa = Gly
<220> FEATURE:
<221> NAME/KEY: VARIANT
<222> LOCATION: (7)...(7)
<223> OTHER INFORMATION: Xaa = Ser or Asn
<220> FEATURE:
<221> NAME/KEY: VARIANT
<222> LOCATION: (8)...(8)
<223> OTHER INFORMATION: Xaa = Ala or Glu

<400> SEQUENCE: 330

Xaa Xaa Xaa Xaa Xaa Xaa Xaa Xaa
1               5

<210> SEQ ID NO 331
<211> LENGTH: 13
```

```
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Ser or Ala
<220> FEATURE:
<221> NAME/KEY: VARIANT
<222> LOCATION: (2)...(2)
<223> OTHER INFORMATION: Xaa = Thr or Lys
<220> FEATURE:
<221> NAME/KEY: VARIANT
<222> LOCATION: (3)...(3)
<223> OTHER INFORMATION: Xaa = Asp or Ile
<220> FEATURE:
<221> NAME/KEY: VARIANT
<222> LOCATION: (4)...(4)
<223> OTHER INFORMATION: Xaa = Gly or Ser
<220> FEATURE:
<221> NAME/KEY: VARIANT
<222> LOCATION: (5)...(5)
<223> OTHER INFORMATION: Xaa = Ala or His
<220> FEATURE:
<221> NAME/KEY: VARIANT
<222> LOCATION: (6)...(6)
<223> OTHER INFORMATION: Xaa = Trp or Tyr
<220> FEATURE:
<221> NAME/KEY: VARIANT
<222> LOCATION: (7)...(7)
<223> OTHER INFORMATION: Xaa = Lys or Asp
<220> FEATURE:
<221> NAME/KEY: VARIANT
<222> LOCATION: (8)...(8)
<223> OTHER INFORMATION: Xaa = Met or Ile
<220> FEATURE:
<221> NAME/KEY: VARIANT
<222> LOCATION: (9)...(9)
<223> OTHER INFORMATION: Xaa = Ser or Leu
<220> FEATURE:
<221> NAME/KEY: VARIANT
<222> LOCATION: (10)...(10)
<223> OTHER INFORMATION: Xaa = Gly or Ser
<220> FEATURE:
<221> NAME/KEY: VARIANT
<222> LOCATION: (11)...(11)
<223> OTHER INFORMATION: Xaa = Leu or Gly
<220> FEATURE:
<221> NAME/KEY: VARIANT
<222> LOCATION: (12)...(12)
<223> OTHER INFORMATION: Xaa = Asp or Met
<220> FEATURE:
<221> NAME/KEY: VARIANT
<222> LOCATION: (13)...(13)
<223> OTHER INFORMATION: Xaa = Val or Asp
<220> FEATURE:
<221> NAME/KEY: VARIANT
<222> LOCATION: (14)...(14)
<223> OTHER INFORMATION: Xaa = Val or absent

<400> SEQUENCE: 331

Xaa Xaa Xaa Xaa Xaa Xaa Xaa Xaa Xaa Xaa Xaa Xaa Xaa
1               5                   10

<210> SEQ ID NO 332
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Gln
<220> FEATURE:
<221> NAME/KEY: VARIANT
```

-continued

```
<222> LOCATION: (2)...(2)
<223> OTHER INFORMATION: Xaa = Asp or Gly
<220> FEATURE:
<221> NAME/KEY: VARIANT
<222> LOCATION: (3)...(3)
<223> OTHER INFORMATION: Xaa = Ile
<220> FEATURE:
<221> NAME/KEY: VARIANT
<222> LOCATION: (4)...(4)
<223> OTHER INFORMATION: Xaa = Ser
<220> FEATURE:
<221> NAME/KEY: VARIANT
<222> LOCATION: (5)...(5)
<223> OTHER INFORMATION: Xaa = Asp or Asn
<220> FEATURE:
<221> NAME/KEY: VARIANT
<222> LOCATION: (6)...(6)
<223> OTHER INFORMATION: Xaa = Tyr or Trp

<400> SEQUENCE: 332

Xaa Xaa Xaa Xaa Xaa Xaa
1               5

<210> SEQ ID NO 333
<211> LENGTH: 3
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Thr or Ala
<220> FEATURE:
<221> NAME/KEY: VARIANT
<222> LOCATION: (2)...(2)
<223> OTHER INFORMATION: Xaa = Thr or Ala
<220> FEATURE:
<221> NAME/KEY: VARIANT
<222> LOCATION: (3)...(3)
<223> OTHER INFORMATION: Xaa = Ser

<400> SEQUENCE: 333

Xaa Xaa Xaa
1

<210> SEQ ID NO 334
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Gln
<220> FEATURE:
<221> NAME/KEY: VARIANT
<222> LOCATION: (2)...(2)
<223> OTHER INFORMATION: Xaa = Lys or Gln
<220> FEATURE:
<221> NAME/KEY: VARIANT
<222> LOCATION: (3)...(3)
<223> OTHER INFORMATION: Xaa = Ala or Tyr
<220> FEATURE:
<221> NAME/KEY: VARIANT
<222> LOCATION: (4)...(4)
<223> OTHER INFORMATION: Xaa = Asp or Asn
<220> FEATURE:
<221> NAME/KEY: VARIANT
<222> LOCATION: (5)...(5)
<223> OTHER INFORMATION: Xaa = Ser
<220> FEATURE:
<221> NAME/KEY: VARIANT
<222> LOCATION: (6)...(6)
```

```
<223> OTHER INFORMATION: Xaa = Ala or Phe
<220> FEATURE:
<221> NAME/KEY: VARIANT
<222> LOCATION: (7)...(7)
<223> OTHER INFORMATION: Xaa = Pro
<220> FEATURE:
<221> NAME/KEY: VARIANT
<222> LOCATION: (8)...(8)
<223> OTHER INFORMATION: Xaa = Leu
<220> FEATURE:
<221> NAME/KEY: VARIANT
<222> LOCATION: (9)...(9)
<223> OTHER INFORMATION: Xaa = Thr

<400> SEQUENCE: 334

Xaa Xaa Xaa Xaa Xaa Xaa Xaa Xaa Xaa
1               5

<210> SEQ ID NO 335
<211> LENGTH: 330
<212> TYPE: PRT
<213> ORGANISM: Artificial Sequence
<220> FEATURE:
<223> OTHER INFORMATION: Synthetic

<400> SEQUENCE: 335

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270
```

```
Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 336
<211> LENGTH: 327
<212> TYPE: PRT
<213> ORGANISM: Artificial Sequence
<220> FEATURE:
<223> OTHER INFORMATION: Synthetic

<400> SEQUENCE: 336

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300
```

```
Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 337
<211> LENGTH: 327
<212> TYPE: PRT
<213> ORGANISM: Artificial Sequence
<220> FEATURE:
<223> OTHER INFORMATION: Synthetic

<400> SEQUENCE: 337

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 338
<211> LENGTH: 1128
<212> TYPE: DNA
<213> ORGANISM: Homo sapiens

<400> SEQUENCE: 338

```
atgcaaaaac tgcaactctg tgtttatatt tacctgttta tgctgattgt tgctggtcca      60
gtggatctaa atgagaacag tgagcaaaaa gaaaatgtgg aaaaagaggg gctgtgtaat     120
gcatgtactt ggagacaaaa cactaaatct tcaagaatag aagccattaa gatacaaatc     180
ctcagtaaac ttcgtctgga acagctcct aacatcagca agatgttat aagacaactt      240
ttacccaaag ctcctccact ccgggaactg attgatcagt atgatgtcca gagggatgac     300
agcagcgatg gctctttgga agatgacgat tatcacgcta acggaaac aatcattacc       360
atgcctacag agtctgattt tctaatgcaa gtggatggaa acccaaatg ttgcttcttt      420
aaatttagct ctaaaataca atacaataaa gtagtaaagg cccaactatg gatatatttg     480
agacccgtcg agactcctac aacagtgttt gtgcaaatcc tgagactcat caacctatg     540
aaagacggta caaggtatac tggaatccga tctctgaaac ttgacatgaa cccaggcact     600
ggtatttggc agagcattga tgtgaagaca gtgttgcaaa attggctcaa caacctgaa     660
tccaacttag gcattgaaat aaaagcttta gatgagaatg gtcatgatct tgctgtaacc     720
ttcccaggac caggagaaga tgggctgaat ccgtttttag aggtcaaggt aacagacaca     780
ccaaaaagat ccagaaggga ttttggtctt gactgtgatg agcactcaac agaatcacga     840
tgctgtcgtt accctctaac tgtggatttt gaagcttttg gatgggattg gattatcgct     900
cctaaaagat ataaggccaa ttactgctct ggagagtgtg aatttgtatt tttacaaaaa     960
tatcctcata ctcatctggt acaccaagca aaccccagag gttcagcagg cccttgctgt    1020
actcccacaa agatgtctcc aattaatatg ctatatttta atggcaaaga acaaataata    1080
tatgggaaaa ttccagcgat ggtagtagac cgctgtgggt gctcatga                 1128
```

<210> SEQ ID NO 339
<211> LENGTH: 375
<212> TYPE: PRT
<213> ORGANISM: Homo sapiens

<400> SEQUENCE: 339

```
Met Gln Lys Leu Gln Leu Cys Val Tyr Ile Tyr Leu Phe Met Leu Ile
1               5                  10                  15

Val Ala Gly Pro Val Asp Leu Asn Glu Asn Ser Glu Gln Lys Glu Asn
            20                  25                  30

Val Glu Lys Glu Gly Leu Cys Asn Ala Cys Thr Trp Arg Gln Asn Thr
        35                  40                  45

Lys Ser Ser Arg Ile Glu Ala Ile Lys Ile Gln Ile Leu Ser Lys Leu
    50                  55                  60

Arg Leu Glu Thr Ala Pro Asn Ile Ser Lys Asp Val Ile Arg Gln Leu
65                  70                  75                  80

Leu Pro Lys Ala Pro Pro Leu Arg Glu Leu Ile Asp Gln Tyr Asp Val
                85                  90                  95

Gln Arg Asp Asp Ser Ser Asp Gly Ser Leu Glu Asp Asp Tyr His
                100                 105                 110

Ala Thr Thr Glu Thr Ile Ile Thr Met Pro Thr Glu Ser Asp Phe Leu
        115                 120                 125
```

Met Gln Val Asp Gly Lys Pro Lys Cys Cys Phe Phe Lys Phe Ser Ser
130                 135                 140

Lys Ile Gln Tyr Asn Lys Val Lys Ala Gln Leu Trp Ile Tyr Leu
145                 150                 155                 160

Arg Pro Val Glu Thr Pro Thr Thr Val Phe Val Gln Ile Leu Arg Leu
                165                 170                 175

Ile Lys Pro Met Lys Asp Gly Thr Arg Tyr Thr Gly Ile Arg Ser Leu
                180                 185                 190

Lys Leu Asp Met Asn Pro Gly Thr Gly Ile Trp Gln Ser Ile Asp Val
                195                 200                 205

Lys Thr Val Leu Gln Asn Trp Leu Lys Gln Pro Glu Ser Asn Leu Gly
210                 215                 220

Ile Glu Ile Lys Ala Leu Asp Glu Asn Gly His Asp Leu Ala Val Thr
225                 230                 235                 240

Phe Pro Gly Pro Gly Glu Asp Gly Leu Asn Pro Phe Leu Glu Val Lys
                245                 250                 255

Val Thr Asp Thr Pro Lys Arg Ser Arg Arg Asp Phe Gly Leu Asp Cys
                260                 265                 270

Asp Glu His Ser Thr Glu Ser Arg Cys Cys Arg Tyr Pro Leu Thr Val
                275                 280                 285

Asp Phe Glu Ala Phe Gly Trp Asp Trp Ile Ile Ala Pro Lys Arg Tyr
                290                 295                 300

Lys Ala Asn Tyr Cys Ser Gly Glu Cys Glu Phe Val Phe Leu Gln Lys
305                 310                 315                 320

Tyr Pro His Thr His Leu Val His Gln Ala Asn Pro Arg Gly Ser Ala
                325                 330                 335

Gly Pro Cys Cys Thr Pro Thr Lys Met Ser Pro Ile Asn Met Leu Tyr
                340                 345                 350

Phe Asn Gly Lys Glu Gln Ile Ile Tyr Gly Lys Ile Pro Ala Met Val
                355                 360                 365

Val Asp Arg Cys Gly Cys Ser
                370                 375

<210> SEQ ID NO 340
<211> LENGTH: 109
<212> TYPE: PRT
<213> ORGANISM: Homo sapiens

<400> SEQUENCE: 340

Asp Phe Gly Leu Asp Cys Asp Glu His Ser Thr Glu Ser Arg Cys Cys
1               5                   10                  15

Arg Tyr Pro Leu Thr Val Asp Phe Glu Ala Phe Gly Trp Asp Trp Ile
                20                  25                  30

Ile Ala Pro Lys Arg Tyr Lys Ala Asn Tyr Cys Ser Gly Glu Cys Glu
                35                  40                  45

Phe Val Phe Leu Gln Lys Tyr Pro His Thr His Leu Val His Gln Ala
                50                  55                  60

Asn Pro Arg Gly Ser Ala Gly Pro Cys Cys Thr Pro Thr Lys Met Ser
65                  70                  75                  80

Pro Ile Asn Met Leu Tyr Phe Asn Gly Lys Glu Gln Ile Ile Tyr Gly
                85                  90                  95

Lys Ile Pro Ala Met Val Val Asp Arg Cys Gly Cys Ser
                100                 105

<210> SEQ ID NO 341

<211> LENGTH: 1224
<212> TYPE: DNA
<213> ORGANISM: Homo sapiens

<400> SEQUENCE: 341

```
atggtgctcg cggccccgct gctgctgggc ttcctgctcc tcgccctgga gctgcggccc      60
cgggggagg cggccgaggg ccccgcggcg gcggcggcgg cggcggcggc ggcggcagcg     120
gcggggtcg ggggggagcg ctccagccgg ccagccccgt ccgtggcgcc cgagccggac     180
ggctgccccg tgtgcgtttg gcggcagcac agccgcgagc tgcgcctaga gagcatcaag     240
tcgcagatct tgagcaaact gcggctcaag gaggcgccca acatcagccg cgaggtggtg     300
aagcagctgc tgcccaaggc gccgccgctg cagcagatcc tggacctaca cgacttccag     360
ggcgacgcgc tgcagcccga ggacttcctg gaggaggacg agtaccacgc caccaccgag     420
accgtcatta gcatggccca ggagacggac ccagcagtac agacagatgg cagccctctc     480
tgctgccatt ttcacttcag ccccaaggtg atgttcacaa aggtactgaa ggcccagctg     540
tgggtgtacc tacggcctgt accccgccca gccacagtct acctgcagat cttgcgacta     600
aaaccctaa ctggggaagg gaccgcaggg ggaggggcg gaggccggcg tcacatccgt     660
atccgctcac tgaagattga gctgcactca cgctcaggcc attggcagag catcgacttc     720
aagcaagtgc tacacagctg gttccgccag ccacagagca actggggcat cgagatcaac     780
gcctttgatc ccagtggcac agacctggct gtcacctccc tggggccggg agccgagggg     840
ctgcatccat tcatggagct tcgagtccta gagaacacaa aacgttcccg cggaacctg     900
ggtctggact gcgacgagca ctcaagcgag tcccgctgct gccgatatcc cctcacagtg     960
gactttgagg ctttcggctg ggactggatc atcgcaccta gcgctacaa ggccaactac    1020
tgctccggcc agtgcgagta catgttcatg caaaaatatc cgcataccca tttggtgcag    1080
caggccaatc caagaggctc tgctgggccc tgttgtaccc ccaccaagat gtccccaatc    1140
aacatgctct acttcaatga caagcagcag attatctacg gcaagatccc tggcatggtg    1200
gtggatcgct gtggctgctc ttaa                                          1224
```

<210> SEQ ID NO 342
<211> LENGTH: 407
<212> TYPE: PRT
<213> ORGANISM: Homo sapiens

<400> SEQUENCE: 342

```
Met Val Leu Ala Ala Pro Leu Leu Leu Gly Phe Leu Leu Leu Ala Leu
1               5                   10                  15

Glu Leu Arg Pro Arg Gly Glu Ala Ala Glu Gly Pro Ala Ala Ala Ala
            20                  25                  30

Ala Ala Ala Ala Ala Ala Ala Gly Val Gly Gly Glu Arg Ser
        35                  40                  45

Ser Arg Pro Ala Pro Ser Val Ala Pro Glu Pro Asp Gly Cys Pro Val
    50                  55                  60

Cys Val Trp Arg Gln His Ser Arg Glu Leu Arg Leu Glu Ser Ile Lys
65                  70                  75                  80

Ser Gln Ile Leu Ser Lys Leu Arg Leu Lys Glu Ala Pro Asn Ile Ser
                85                  90                  95

Arg Glu Val Val Lys Gln Leu Leu Pro Lys Ala Pro Leu Gln Gln
            100                 105                 110

Ile Leu Asp Leu His Asp Phe Gln Gly Asp Ala Leu Gln Pro Glu Asp
        115                 120                 125
```

-continued

Phe Leu Glu Glu Asp Glu Tyr His Ala Thr Thr Glu Thr Val Ile Ser
130                 135                 140

Met Ala Gln Glu Thr Asp Pro Ala Val Gln Thr Asp Gly Ser Pro Leu
145                 150                 155                 160

Cys Cys His Phe His Phe Ser Pro Lys Val Met Phe Thr Lys Val Leu
                165                 170                 175

Lys Ala Gln Leu Trp Val Tyr Leu Arg Pro Val Pro Arg Pro Ala Thr
                180                 185                 190

Val Tyr Leu Gln Ile Leu Arg Leu Lys Pro Leu Thr Gly Glu Gly Thr
                195                 200                 205

Ala Gly Gly Gly Gly Gly Arg Arg His Ile Arg Ile Arg Ser Leu
210                 215                 220

Lys Ile Glu Leu His Ser Arg Ser Gly His Trp Gln Ser Ile Asp Phe
225                 230                 235                 240

Lys Gln Val Leu His Ser Trp Phe Arg Gln Pro Gln Ser Asn Trp Gly
                245                 250                 255

Ile Glu Ile Asn Ala Phe Asp Pro Ser Gly Thr Asp Leu Ala Val Thr
                260                 265                 270

Ser Leu Gly Pro Gly Ala Glu Gly Leu His Pro Phe Met Glu Leu Arg
                275                 280                 285

Val Leu Glu Asn Thr Lys Arg Ser Arg Arg Asn Leu Gly Leu Asp Cys
290                 295                 300

Asp Glu His Ser Ser Glu Ser Arg Cys Cys Arg Tyr Pro Leu Thr Val
305                 310                 315                 320

Asp Phe Glu Ala Phe Gly Trp Asp Trp Ile Ile Ala Pro Lys Arg Tyr
                325                 330                 335

Lys Ala Asn Tyr Cys Ser Gly Gln Cys Glu Tyr Met Phe Met Gln Lys
                340                 345                 350

Tyr Pro His Thr His Leu Val Gln Gln Ala Asn Pro Arg Gly Ser Ala
                355                 360                 365

Gly Pro Cys Cys Thr Pro Thr Lys Met Ser Pro Ile Asn Met Leu Tyr
370                 375                 380

Phe Asn Asp Lys Gln Gln Ile Ile Tyr Gly Lys Ile Pro Gly Met Val
385                 390                 395                 400

Val Asp Arg Cys Gly Cys Ser
                405

<210> SEQ ID NO 343
<211> LENGTH: 109
<212> TYPE: PRT
<213> ORGANISM: Homo sapiens

<400> SEQUENCE: 343

Asn Leu Gly Leu Asp Cys Asp Glu His Ser Ser Glu Ser Arg Cys Cys
1               5                   10                  15

Arg Tyr Pro Leu Thr Val Asp Phe Glu Ala Phe Gly Trp Asp Trp Ile
                20                  25                  30

Ile Ala Pro Lys Arg Tyr Lys Ala Asn Tyr Cys Ser Gly Gln Cys Glu
            35                  40                  45

Tyr Met Phe Met Gln Lys Tyr Pro His Thr His Leu Val Gln Gln Ala
        50                  55                  60

Asn Pro Arg Gly Ser Ala Gly Pro Cys Cys Thr Pro Thr Lys Met Ser
65                  70                  75                  80

Pro Ile Asn Met Leu Tyr Phe Asn Asp Lys Gln Gln Ile Ile Tyr Gly

```
              85                  90                  95
Lys Ile Pro Gly Met Val Val Asp Arg Cys Gly Cys Ser
            100                 105
```

<210> SEQ ID NO 344
<211> LENGTH: 1503
<212> TYPE: DNA
<213> ORGANISM: Homo spiens

<400> SEQUENCE: 344

| | | | | | |
|---|---|---|---|---|---|
| atgagactcc | ccaaactcct | cactttcttg | ctttggtacc | tggcttggct | ggacctggaa | 60 |
| ttcatctgca | ctgtgttggg | tgccctgac | ttgggccaga | acccagggg | accaggcca | 120 |
| ggattggcca | aagcagaggc | caaggagagg | ccccccctgg | cccggaacgt | cttcaggcca | 180 |
| gggggtcaca | gctatggtgg | gggggccacc | aatgccaatg | ccagggcaaa | gggaggcacc | 240 |
| gggcagacag | gaggcctgac | acagcccaag | aaggatgaac | caaaaagct | gccccccaga | 300 |
| ccgggcggcc | ctgaacccaa | gcaggacac | cctccccaaa | caaggcaggc | tacagcccgg | 360 |
| actgtgaccc | caaaaggaca | gcttcccgga | ggcaaggcac | cccaaaaagc | aggatctgtc | 420 |
| cccagctcct | tcctgctgaa | gaaggccagg | gagcccgggc | cccacgaga | gcccaaggag | 480 |
| ccgtttcgcc | cacccccat | cacaccccac | gagtacatgc | tctcgctgta | caggacgctg | 540 |
| tccgatgctg | acagaaaggg | aggcaacagc | agcgtgaagt | tggaggctgg | cctgccaac | 600 |
| accatcacca | gctttattga | caaagggcaa | gatgaccgag | gtcccgtggt | caggaagcag | 660 |
| aggtacgtgt | ttgacattag | tgccctggag | aaggatgggc | tgctggggc | cgagctgcgg | 720 |
| atcttgcgga | agaagccctc | ggacacggcc | aagccagcgg | ccccggagg | cgggcgggct | 780 |
| gcccagctga | gctgtccag | ctgccccagc | ggccggcagc | cggcctcctt | gctggatgtg | 840 |
| cgctccgtgc | aggcctgga | cggatctggc | tgggaggtgt | tcgacatctg | gaagctcttc | 900 |
| cgaaacttta | agaactcggc | ccagctgtgc | ctggagctgg | aggcctggga | acggggcagg | 960 |
| gccgtggacc | tccgtggcct | gggcttcgac | cgcgccgccc | ggcaggtcca | cgagaaggcc | 1020 |
| ctgttcctgg | tgtttggccg | caccaagaaa | cgggacctgt | tctttaatga | gattaaggcc | 1080 |
| cgctctggcc | aggacgataa | gaccgtgtat | gagtacctgt | tcagccagcg | cgcgaaaacgg | 1140 |
| cgggccccac | tggccactcg | ccagggcaag | cgacccagca | agaaccttaa | ggctcgctgc | 1200 |
| agtcggaagg | cactgcatgt | caacttcaag | gacatgggct | gggacgactg | gatcatcgca | 1260 |
| cccttgagt | acgaggcttt | ccactgcgag | gggctgtgcg | agttcccatt | gcgctcccac | 1320 |
| ctggagccca | cgaatcatgc | agtcatccag | accctgatga | actccatgga | ccccgagtcc | 1380 |
| acaccacca | cctgctgtgt | gcccacgcgg | ctgagtccca | tcagcatcct | cttcattgac | 1440 |
| tctgccaaca | acgtggtgta | taagcagtat | gaggacatgg | tcgtggagtc | gtgtggctgc | 1500 |
| agg | | | | | | 1503 |

<210> SEQ ID NO 345
<211> LENGTH: 501
<212> TYPE: PRT
<213> ORGANISM: Homo sapiens

<400> SEQUENCE: 345

```
Met Arg Leu Pro Lys Leu Leu Thr Phe Leu Leu Trp Tyr Leu Ala Trp
1               5                   10                  15
Leu Asp Leu Glu Phe Ile Cys Thr Val Leu Gly Ala Pro Asp Leu Gly
            20                  25                  30
```

-continued

```
Gln Arg Pro Gln Gly Thr Arg Pro Gly Leu Ala Lys Ala Glu Ala Lys
            35                  40                  45

Glu Arg Pro Pro Leu Ala Arg Asn Val Phe Arg Pro Gly Gly His Ser
 50                  55                  60

Tyr Gly Gly Gly Ala Thr Asn Ala Asn Ala Arg Ala Lys Gly Gly Thr
 65                  70                  75                  80

Gly Gln Thr Gly Gly Leu Thr Gln Pro Lys Lys Asp Glu Pro Lys Lys
                    85                  90                  95

Leu Pro Pro Arg Pro Gly Gly Pro Glu Pro Lys Pro Gly His Pro Pro
            100                 105                 110

Gln Thr Arg Gln Ala Thr Ala Arg Thr Val Thr Pro Lys Gly Gln Leu
            115                 120                 125

Pro Gly Gly Lys Ala Pro Pro Lys Ala Gly Ser Val Pro Ser Ser Phe
 130                 135                 140

Leu Leu Lys Lys Ala Arg Glu Pro Gly Pro Pro Arg Glu Pro Lys Glu
 145                 150                 155                 160

Pro Phe Arg Pro Pro Ile Thr Pro His Glu Tyr Met Leu Ser Leu
                    165                 170                 175

Tyr Arg Thr Leu Ser Asp Ala Asp Arg Lys Gly Gly Asn Ser Ser Val
            180                 185                 190

Lys Leu Glu Ala Gly Leu Ala Asn Thr Ile Thr Ser Phe Ile Asp Lys
            195                 200                 205

Gly Gln Asp Asp Arg Gly Pro Val Val Arg Lys Gln Arg Tyr Val Phe
            210                 215                 220

Asp Ile Ser Ala Leu Glu Lys Asp Gly Leu Leu Gly Ala Glu Leu Arg
225                 230                 235                 240

Ile Leu Arg Lys Lys Pro Ser Asp Thr Ala Lys Pro Ala Ala Pro Gly
                    245                 250                 255

Gly Gly Arg Ala Ala Gln Leu Lys Leu Ser Ser Cys Pro Ser Gly Arg
            260                 265                 270

Gln Pro Ala Ser Leu Leu Asp Val Arg Ser Val Pro Gly Leu Asp Gly
            275                 280                 285

Ser Gly Trp Glu Val Phe Asp Ile Trp Lys Leu Phe Arg Asn Phe Lys
290                 295                 300

Asn Ser Ala Gln Leu Cys Leu Glu Leu Glu Ala Trp Glu Arg Gly Arg
305                 310                 315                 320

Ala Val Asp Leu Arg Gly Leu Gly Phe Asp Arg Ala Arg Gln Val
                    325                 330                 335

His Glu Lys Ala Leu Phe Leu Val Phe Gly Arg Thr Lys Lys Arg Asp
            340                 345                 350

Leu Phe Phe Asn Glu Ile Lys Ala Arg Ser Gly Gln Asp Asp Lys Thr
            355                 360                 365

Val Tyr Glu Tyr Leu Phe Ser Gln Arg Arg Lys Arg Arg Ala Pro Leu
            370                 375                 380

Ala Thr Arg Gln Gly Lys Arg Pro Ser Lys Asn Leu Lys Ala Arg Cys
385                 390                 395                 400

Ser Arg Lys Ala Leu His Val Asn Phe Lys Asp Met Gly Trp Asp Asp
                    405                 410                 415

Trp Ile Ile Ala Pro Leu Glu Tyr Glu Ala Phe His Cys Glu Gly Leu
            420                 425                 430

Cys Glu Phe Pro Leu Arg Ser His Leu Glu Pro Thr Asn His Ala Val
            435                 440                 445

Ile Gln Thr Leu Met Asn Ser Met Asp Pro Glu Ser Thr Pro Pro Thr
```

```
                450                 455                 460
Cys Cys Val Pro Thr Arg Leu Ser Pro Ile Ser Ile Leu Phe Ile Asp
465                 470                 475                 480

Ser Ala Asn Asn Val Val Tyr Lys Gln Tyr Glu Asp Met Val Val Glu
                485                 490                 495

Ser Cys Gly Cys Arg
            500

<210> SEQ ID NO 346
<211> LENGTH: 120
<212> TYPE: PRT
<213> ORGANISM: Homo sapiens

<400> SEQUENCE: 346

Ala Pro Leu Ala Thr Arg Gln Gly Lys Arg Pro Ser Lys Asn Leu Lys
1               5                   10                  15

Ala Arg Cys Ser Arg Lys Ala Leu His Val Asn Phe Lys Asp Met Gly
            20                  25                  30

Trp Asp Asp Trp Ile Ile Ala Pro Leu Glu Tyr Glu Ala Phe His Cys
        35                  40                  45

Glu Gly Leu Cys Glu Phe Pro Leu Arg Ser His Leu Glu Pro Thr Asn
    50                  55                  60

His Ala Val Ile Gln Thr Leu Met Asn Ser Met Asp Pro Glu Ser Thr
65                  70                  75                  80

Pro Pro Thr Cys Cys Val Pro Thr Arg Leu Ser Pro Ile Ser Ile Leu
                85                  90                  95

Phe Ile Asp Ser Ala Asn Asn Val Val Tyr Lys Gln Tyr Glu Asp Met
            100                 105                 110

Val Val Glu Ser Cys Gly Cys Arg
        115                 120

<210> SEQ ID NO 347
<211> LENGTH: 107
<212> TYPE: PRT
<213> ORGANISM: Artificial Sequence
<220> FEATURE:
<223> OTHER INFORMATION: Synthetic

<400> SEQUENCE: 347

Gln Ala Lys His Lys Gln Arg Lys Arg Leu Lys Ser Ser Cys Arg Tyr
1               5                   10                  15

Pro Leu Thr Val Asp Phe Glu Ala Phe Gly Trp Asp Trp Ile Ile Ala
            20                  25                  30

Pro Lys Arg Tyr Lys Ala Asn Tyr Cys Ser Gly Glu Cys Glu Phe Val
        35                  40                  45

Phe Leu Gln Lys Tyr Pro His Thr His Leu Val His Gln Ala Asn Pro
    50                  55                  60

Arg Gly Ser Ala Gly Pro Cys Cys Thr Pro Thr Lys Met Ser Pro Ile
65                  70                  75                  80

Asn Met Leu Tyr Phe Asn Gly Lys Glu Gln Ile Ile Tyr Gly Lys Ile
                85                  90                  95

Pro Ala Met Val Val Asp Arg Cys Gly Cys Ser
            100                 105

<210> SEQ ID NO 348
<211> LENGTH: 109
<212> TYPE: PRT
<213> ORGANISM: Artificial Sequence
```

```
<220> FEATURE:
<223> OTHER INFORMATION: Synthetic

<400> SEQUENCE: 348

Ala Leu Asp Thr Asn Tyr Cys Phe Ser Ser Thr Glu Lys Asn Cys Cys
1               5                   10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Glu Cys Glu
        35                  40                  45

Phe Val Phe Leu Gln Lys Tyr Pro His Thr His Leu Val His Gln Ala
    50                  55                  60

Asn Pro Arg Gly Ser Ala Gly Pro Cys Cys Thr Pro Thr Lys Met Ser
65                  70                  75                  80

Pro Ile Asn Met Leu Tyr Phe Asn Gly Lys Glu Gln Ile Ile Tyr Gly
                85                  90                  95

Lys Ile Pro Ala Met Val Val Asp Arg Cys Gly Cys Ser
            100                 105

<210> SEQ ID NO 349
<211> LENGTH: 111
<212> TYPE: PRT
<213> ORGANISM: Artificial Sequence
<220> FEATURE:
<223> OTHER INFORMATION: Synthetic

<400> SEQUENCE: 349

Asp Phe Gly Leu Asp Cys Asp Glu His Ser Thr Glu Ser Arg Cys Cys
1               5                   10                  15

Lys Arg His Pro Leu Tyr Val Asp Phe Ser Asp Val Gly Trp Asn Asp
            20                  25                  30

Trp Ile Val Ala Pro Pro Gly Tyr His Ala Phe Tyr Cys Ser Gly Glu
        35                  40                  45

Cys Glu Phe Val Phe Leu Gln Lys Tyr Pro His Thr His Leu Val His
    50                  55                  60

Gln Ala Asn Pro Arg Gly Ser Ala Gly Pro Cys Cys Thr Pro Thr Lys
65                  70                  75                  80

Met Ser Pro Ile Asn Met Leu Tyr Phe Asn Gly Lys Glu Gln Ile Ile
                85                  90                  95

Tyr Gly Lys Ile Pro Ala Met Val Val Asp Arg Cys Gly Cys Ser
            100                 105                 110

<210> SEQ ID NO 350
<211> LENGTH: 110
<212> TYPE: PRT
<213> ORGANISM: Artificial Sequence
<220> FEATURE:
<223> OTHER INFORMATION: Synthetic

<400> SEQUENCE: 350

Asp Phe Gly Leu Asp Cys Asp Glu His Ser Thr Glu Ser Arg Cys Cys
1               5                   10                  15

Val Arg Gln Leu Tyr Ile Asp Phe Arg Lys Asp Leu Gly Trp Lys Trp
            20                  25                  30

Ile His Glu Pro Lys Gly Tyr His Ala Asn Phe Cys Ser Gly Glu Cys
        35                  40                  45

Glu Phe Val Phe Leu Gln Lys Tyr Pro His Thr His Leu Val His Gln
    50                  55                  60
```

Ala Asn Pro Arg Gly Ser Ala Gly Pro Cys Cys Thr Pro Thr Lys Met
 65                  70                  75                  80

Ser Pro Ile Asn Met Leu Tyr Phe Asn Gly Lys Glu Gln Ile Ile Tyr
             85                   90                  95

Gly Lys Ile Pro Ala Met Val Val Asp Arg Cys Gly Cys Ser
            100                 105                 110

<210> SEQ ID NO 351
<211> LENGTH: 114
<212> TYPE: PRT
<213> ORGANISM: Artificial Sequence
<220> FEATURE:
<223> OTHER INFORMATION: Synthetic

<400> SEQUENCE: 351

Asp Phe Gly Leu Asp Cys Asp Glu His Ser Thr Glu Ser Arg Cys Cys
 1               5                   10                  15

Arg Tyr Pro Leu Thr Val Asp Phe Glu Ala Phe Gly Trp Asp Trp Ile
             20                  25                  30

Ile Ala Pro Lys Arg Tyr Lys Ala Asn Tyr Cys Ser Gly Glu Cys Pro
         35                  40                  45

Phe Pro Leu Ala Asp His Leu Asn Ser Thr Asn His Ala Ile Val Gln
 50                  55                  60

Thr Leu Val Asn Ser Val Asn Ser Lys Ile Pro Lys Ala Cys Cys Thr
 65                  70                  75                  80

Pro Thr Lys Met Ser Pro Ile Asn Met Leu Tyr Phe Asn Gly Lys Glu
             85                  90                  95

Gln Ile Ile Tyr Gly Lys Ile Pro Ala Met Val Val Asp Arg Cys Gly
            100                 105                 110

Cys Ser

<210> SEQ ID NO 352
<211> LENGTH: 112
<212> TYPE: PRT
<213> ORGANISM: Artificial Sequence
<220> FEATURE:
<223> OTHER INFORMATION: Synthetic

<400> SEQUENCE: 352

Asp Phe Gly Leu Asp Cys Asp Glu His Ser Thr Glu Ser Arg Cys Cys
 1               5                   10                  15

Arg Tyr Pro Leu Thr Val Asp Phe Glu Ala Phe Gly Trp Asp Trp Ile
             20                  25                  30

Ile Ala Pro Lys Arg Tyr Lys Ala Asn Tyr Cys Ser Gly Glu Cys Pro
         35                  40                  45

Tyr Ile Trp Ser Leu Asp Thr Gln Tyr Ser Lys Val Leu Ala Leu Tyr
 50                  55                  60

Asn Gln His Asn Pro Gly Ala Ser Ala Ala Pro Cys Cys Thr Pro Thr
 65                  70                  75                  80

Lys Met Ser Pro Ile Asn Met Leu Tyr Phe Asn Gly Lys Glu Gln Ile
             85                  90                  95

Ile Tyr Gly Lys Ile Pro Ala Met Val Val Asp Arg Cys Gly Cys Ser
            100                 105                 110

<210> SEQ ID NO 353
<211> LENGTH: 109
<212> TYPE: PRT
<213> ORGANISM: Artificial Sequence
<220> FEATURE:

<223> OTHER INFORMATION: Synthetic

<400> SEQUENCE: 353

Asp Phe Gly Leu Asp Cys Asp Glu His Ser Thr Glu Ser Arg Cys Cys
1               5                   10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Glu Cys Glu
        35                  40                  45

Phe Val Phe Leu Gln Lys Tyr Pro His Thr His Leu Val His Gln Ala
    50                  55                  60

Asn Ser Val Asn Ser Lys Ile Pro Cys Cys Thr Pro Thr Lys Met Ser
65                  70                  75                  80

Pro Ile Asn Met Leu Tyr Phe Asn Gly Lys Glu Gln Ile Ile Tyr Gly
                85                  90                  95

Lys Ile Pro Ala Met Val Val Asp Arg Cys Gly Cys Ser
            100                 105

<210> SEQ ID NO 354
<211> LENGTH: 109
<212> TYPE: PRT
<213> ORGANISM: Artificial Sequence
<220> FEATURE:
<223> OTHER INFORMATION: Synthetic

<400> SEQUENCE: 354

Asp Phe Gly Leu Asp Cys Asp Glu His Ser Thr Glu Ser Arg Cys Cys
1               5                   10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Glu Cys Glu
        35                  40                  45

Phe Val Phe Leu Gln Lys Tyr Pro His Thr His Leu Val His Gln Ala
    50                  55                  60

Asn Pro Gly Ala Ser Ala Ala Pro Cys Cys Thr Pro Thr Lys Met Ser
65                  70                  75                  80

Pro Ile Asn Met Leu Tyr Phe Asn Gly Lys Glu Gln Ile Ile Tyr Gly
                85                  90                  95

Lys Ile Pro Ala Met Val Val Asp Arg Cys Gly Cys Ser
            100                 105

<210> SEQ ID NO 355
<211> LENGTH: 109
<212> TYPE: PRT
<213> ORGANISM: Artificial Sequence
<220> FEATURE:
<223> OTHER INFORMATION: Synthetic

<400> SEQUENCE: 355

Asp Phe Gly Leu Asp Cys Asp Glu His Ser Thr Glu Ser Arg Cys Cys
1               5                   10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Glu Cys Glu
        35                  40                  45

Phe Val Phe Leu Gln Lys Tyr Pro His Thr His Leu Val His Gln Ala
    50                  55                  60

Asn Pro Arg Gly Ser Ala Gly Pro Cys Cys Val Pro Thr Glu Leu Ser

```
                65                  70                  75                  80
Ala Ile Ser Met Leu Tyr Leu Asp Glu Asn Glu Lys Val Val Leu Lys
                    85                  90                  95

Asn Tyr Gln Asp Met Val Val Glu Gly Cys Gly Cys Ser
            100                 105

<210> SEQ ID NO 356
<211> LENGTH: 108
<212> TYPE: PRT
<213> ORGANISM: Artificial Sequence
<220> FEATURE:
<223> OTHER INFORMATION: Synthetic

<400> SEQUENCE: 356

Asp Phe Gly Leu Asp Cys Asp Glu His Ser Thr Glu Ser Arg Cys Cys
1               5                   10                  15

Arg Tyr Pro Leu Thr Val Asp Phe Glu Ala Phe Gly Trp Asp Trp Ile
                20                  25                  30

Ile Ala Pro Lys Arg Tyr Lys Ala Asn Tyr Cys Ser Gly Glu Cys Glu
            35                  40                  45

Phe Val Phe Leu Gln Lys Tyr Pro His Thr His Leu Val His Gln Ala
        50                  55                  60

Asn Pro Arg Gly Ser Ala Gly Pro Cys Cys Val Pro Gln Ala Leu Glu
65                  70                  75                  80

Pro Leu Pro Ile Val Tyr Tyr Val Gly Arg Lys Pro Lys Val Glu Gln
                85                  90                  95

Leu Ser Asn Met Ile Val Arg Ser Cys Gly Cys Ser
            100                 105

<210> SEQ ID NO 357
<211> LENGTH: 109
<212> TYPE: PRT
<213> ORGANISM: Artificial Sequence
<220> FEATURE:
<223> OTHER INFORMATION: Synthetic

<400> SEQUENCE: 357

Asp Phe Gly Leu Asp Cys Asp Glu His Ser Thr Glu Ser Arg Cys Cys
1               5                   10                  15

Arg Tyr Pro Leu Thr Val Asp Phe Glu Ala Phe Gly Trp Asp Trp Ile
                20                  25                  30

Ile Ala Pro Lys Arg Tyr Lys Ala Asn Tyr Cys Ser Gly Glu Cys Glu
            35                  40                  45

Phe Val Phe Leu Gln Lys Tyr Pro His Thr His Leu Val His Gln Ala
        50                  55                  60

Asn Pro Arg Gly Ser Ala Gly Pro Cys Cys Thr Pro Thr Lys Met Ser
65                  70                  75                  80

Pro Ile Asn Met Leu Tyr Phe Asn Gly Lys Glu Lys Val Val Leu Lys
                85                  90                  95

Asn Tyr Gln Asp Met Val Val Glu Gly Cys Gly Cys Ser
            100                 105

<210> SEQ ID NO 358
<211> LENGTH: 108
<212> TYPE: PRT
<213> ORGANISM: Artificial Sequence
<220> FEATURE:
<223> OTHER INFORMATION: Synthetic

<400> SEQUENCE: 358
```

```
Asp Phe Gly Leu Asp Cys Asp Glu His Ser Thr Glu Ser Arg Cys Cys
1               5                   10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Glu Cys Glu
            35                  40                  45

Phe Val Phe Leu Gln Lys Tyr Pro His Thr His Leu Val His Gln Ala
    50                  55                  60

Asn Pro Arg Gly Ser Ala Gly Pro Cys Cys Thr Pro Thr Lys Met Ser
65              70                  75                  80

Pro Ile Asn Met Leu Tyr Phe Asn Gly Lys Lys Pro Lys Val Glu Gln
            85                  90                  95

Leu Ser Asn Met Ile Val Arg Ser Cys Gly Cys Ser
            100                 105
```

<210> SEQ ID NO 359
<211> LENGTH: 360
<212> TYPE: DNA
<213> ORGANISM: Artificial Sequence
<220> FEATURE:
<223> OTHER INFORMATION: Synthetic

<400> SEQUENCE: 359

```
gaggtgcagg tgttggagtc tgggggagac ttggtacagc ctgggggtc cctgagactc     60 tcctgtgcag cctctggatt cacctttagt gcctatgcca tgacctgggt ccgccaggct   120
ccagggaagg gctggagtg gtctcagct attagtggta gtggtggtag cgcatactac    180
gcagactccg tgaagggccg gttcaccatc tccagagaca attccaagaa cacggtatat   240
ctgcagatga acagcctgag agccgaggac acggccgtat attactgtgc gaaagatggg   300
gcctggaaaa tgtccggttt ggacgtctgg ggccaaggga ccacggtcat cgtctcctca   360
```

<210> SEQ ID NO 360
<211> LENGTH: 120
<212> TYPE: PRT
<213> ORGANISM: Artificial Sequence
<220> FEATURE:
<223> OTHER INFORMATION: Synthetic

<400> SEQUENCE: 360

```
Glu Val Gln Val Leu Glu Ser Gly Gly Asp Leu Val Gln Pro Gly Gly
1               5                   10                  15

Ser Leu Arg Leu Ser Cys Ala Ala Ser Gly Phe Thr Phe Ser Ala Tyr
            20                  25                  30

Ala Met Thr Trp Val Arg Gln Ala Pro Gly Lys Gly Leu Glu Trp Val
            35                  40                  45

Ser Ala Ile Ser Gly Ser Gly Gly Ser Ala Tyr Tyr Ala Asp Ser Val
    50                  55                  60

Lys Gly Arg Phe Thr Ile Ser Arg Asp Asn Ser Lys Asn Thr Val Tyr
65              70                  75                  80

Leu Gln Met Asn Ser Leu Arg Ala Glu Asp Thr Ala Val Tyr Tyr Cys
            85                  90                  95

Ala Lys Asp Gly Ala Trp Lys Met Ser Gly Leu Asp Val Trp Gly Gln
            100                 105                 110

Gly Thr Thr Val Ile Val Ser Ser
            115                 120
```

```
<210> SEQ ID NO 361
<211> LENGTH: 24
<212> TYPE: DNA
<213> ORGANISM: Artificial Sequence
<220> FEATURE:
<223> OTHER INFORMATION: Synthetic

<400> SEQUENCE: 361
ggattcacct ttagtgccta tgcc                                          24

<210> SEQ ID NO 362
<211> LENGTH: 8
<212> TYPE: PRT
<213> ORGANISM: Artificial Sequence
<220> FEATURE:
<223> OTHER INFORMATION: Synthetic

<400> SEQUENCE: 362

Gly Phe Thr Phe Ser Ala Tyr Ala
1               5

<210> SEQ ID NO 363
<211> LENGTH: 24
<212> TYPE: DNA
<213> ORGANISM: Artificial Sequence
<220> FEATURE:
<223> OTHER INFORMATION: Synthetic

<400> SEQUENCE: 363
attagtggta gtggtggtag cgca                                          24

<210> SEQ ID NO 364
<211> LENGTH: 8
<212> TYPE: PRT
<213> ORGANISM: Artificial Sequence
<220> FEATURE:
<223> OTHER INFORMATION: Synthetic

<400> SEQUENCE: 364

Ile Ser Gly Ser Gly Gly Ser Ala
1               5

<210> SEQ ID NO 365
<211> LENGTH: 39
<212> TYPE: DNA
<213> ORGANISM: Artificial Sequence
<220> FEATURE:
<223> OTHER INFORMATION: Synthetic

<400> SEQUENCE: 365
gcgaaagatg gggcctggaa aatgtccggt ttggacgtc                          39

<210> SEQ ID NO 366
<211> LENGTH: 13
<212> TYPE: PRT
<213> ORGANISM: Artificial Sequence
<220> FEATURE:
<223> OTHER INFORMATION: Synthetic

<400> SEQUENCE: 366

Ala Lys Asp Gly Ala Trp Lys Met Ser Gly Leu Asp Val
1               5                   10

<210> SEQ ID NO 367
<211> LENGTH: 321
<212> TYPE: DNA
<213> ORGANISM: Artificial Sequence
```

<220> FEATURE:
<223> OTHER INFORMATION: Synthetic

<400> SEQUENCE: 367

```
gacatccaga tgacccagtc tccagcctcc ctgtctgcat ctgttggaga cagagtcacc    60
atcacttgtc gggcgagtca ggacattagc gattatttag cctggtatca gcagaaacca   120
gggaaaattc ctaggctcct gatctatact acatccactt tgcaatcagg ggtcccatct   180
cggttccgtg gcagtgggtc tgggacagat ttcactctca ccatcagcag cctgcagcct   240
gaagatgttg caacttatta ctgtcagaag tatgacagtg ccccgctcac tttcggcgga   300
gggaccaagg tggagatcaa a                                              321
```

<210> SEQ ID NO 368
<211> LENGTH: 107
<212> TYPE: PRT
<213> ORGANISM: Artificial Sequence
<220> FEATURE:
<223> OTHER INFORMATION: Synthetic

<400> SEQUENCE: 368

Asp Ile Gln Met Thr Gln Ser Pro Ala Ser Leu Ser Ala Ser Val Gly
1               5                   10                  15

Asp Arg Val Thr Ile Thr Cys Arg Ala Ser Gln Asp Ile Ser Asp Tyr
            20                  25                  30

Leu Ala Trp Tyr Gln Gln Lys Pro Gly Lys Ile Pro Arg Leu Leu Ile
        35                  40                  45

Tyr Thr Thr Ser Thr Leu Gln Ser Gly Val Pro Ser Arg Phe Arg Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asp Ser Ala Pro Leu
                85                  90                  95

Thr Phe Gly Gly Gly Thr Lys Val Glu Ile Lys
            100                 105

<210> SEQ ID NO 369
<211> LENGTH: 18
<212> TYPE: DNA
<213> ORGANISM: Artificial Sequence
<220> FEATURE:
<223> OTHER INFORMATION: Synthetic

<400> SEQUENCE: 369

```
caggacatta gcgattat                                                   18
```

<210> SEQ ID NO 370
<211> LENGTH: 6
<212> TYPE: PRT
<213> ORGANISM: Artificial Sequence
<220> FEATURE:
<223> OTHER INFORMATION: Synthetic

<400> SEQUENCE: 370

Gln Asp Ile Ser Asp Tyr
1               5

<210> SEQ ID NO 371
<211> LENGTH: 9
<212> TYPE: DNA
<213> ORGANISM: Artificial Sequence
<220> FEATURE:

```
<223> OTHER INFORMATION: Synthetic

<400> SEQUENCE: 371 actacatcc                                                                9

<210> SEQ ID NO 372
<211> LENGTH: 3
<212> TYPE: PRT
<213> ORGANISM: Artificial Sequence
<220> FEATURE:
<223> OTHER INFORMATION: Synthetic

<400> SEQUENCE: 372

Thr Thr Ser
1

<210> SEQ ID NO 373
<211> LENGTH: 27
<212> TYPE: DNA
<213> ORGANISM: Artificial Sequence
<220> FEATURE:
<223> OTHER INFORMATION: Synthetic

<400> SEQUENCE: 373
cagaagtatg acagtgcccc gctcact                                           27

<210> SEQ ID NO 374
<211> LENGTH: 9
<212> TYPE: PRT
<213> ORGANISM: Artificial Sequence
<220> FEATURE:
<223> OTHER INFORMATION: Synthetic

<400> SEQUENCE: 374

Gln Lys Tyr Asp Ser Ala Pro Leu Thr
1               5

<210> SEQ ID NO 375
<211> LENGTH: 363
<212> TYPE: DNA
<213> ORGANISM: Artificial Sequence
<220> FEATURE:
<223> OTHER INFORMATION: Synthetic

<400> SEQUENCE: 375
caggtgcagc tggtggagtc tgggggaggc gtggtccagc ctgggaagtc cctgcgactc        60
tcctgtgcag cgtctggatt caccttcagt agttttggca tgcattgggt ccgccaggct       120
ccaggcaagg ggctggagtg ggtggcagtt attgggtatg atggaggtaa tgaatactat       180
gccgactccg tgaagggccg attcaccatc tccagagaca attccaagaa cacgctgaat       240
ctgcaaatga gcagcctgag agccgaagac acggctgtgt attattgttc gactataagt       300
cattacgata ttttgagcgg tatggacgtc tggggccgag gaccacggt caccgtctcc       360 tca                                                                    363

<210> SEQ ID NO 376
<211> LENGTH: 121
<212> TYPE: PRT
<213> ORGANISM: Artificial Sequence
<220> FEATURE:
<223> OTHER INFORMATION: Synthetic

<400> SEQUENCE: 376

Gln Val Gln Leu Val Glu Ser Gly Gly Gly Val Val Gln Pro Gly Lys
```

```
              1               5                  10                  15
            Ser Leu Arg Leu Ser Cys Ala Ala Ser Gly Phe Thr Phe Ser Ser Phe
                            20                  25                  30

Gly Met His Trp Val Arg Gln Ala Pro Gly Lys Gly Leu Glu Trp Val
                        35                  40                  45

Ala Val Ile Gly Tyr Asp Gly Asn Glu Tyr Tyr Ala Asp Ser Val
                    50                  55                  60

Lys Gly Arg Phe Thr Ile Ser Arg Asp Asn Ser Lys Asn Thr Leu Asn
            65                  70                  75                  80

Leu Gln Met Ser Ser Leu Arg Ala Glu Asp Thr Ala Val Tyr Tyr Cys
                            85                  90                  95

Ser Thr Ile Ser His Tyr Asp Ile Leu Ser Gly Met Asp Val Trp Gly
                            100                 105                 110

Arg Gly Thr Thr Val Thr Val Ser Ser
                        115                 120
```

<210> SEQ ID NO 377
<211> LENGTH: 24
<212> TYPE: DNA
<213> ORGANISM: Artificial Sequence
<220> FEATURE:
<223> OTHER INFORMATION: Synthetic

<400> SEQUENCE: 377
ggattcacct tcagtagttt tggc                                           24

<210> SEQ ID NO 378
<211> LENGTH: 8
<212> TYPE: PRT
<213> ORGANISM: Artificial Sequence
<220> FEATURE:
<223> OTHER INFORMATION: Synthetic

<400> SEQUENCE: 378

```
Gly Phe Thr Phe Ser Ser Phe Gly
1               5
```

<210> SEQ ID NO 379
<211> LENGTH: 24
<212> TYPE: DNA
<213> ORGANISM: Artificial Sequence
<220> FEATURE:
<223> OTHER INFORMATION: Synthetic

<400> SEQUENCE: 379
attgggtatg atggaggtaa tgaa                                           24

<210> SEQ ID NO 380
<211> LENGTH: 8
<212> TYPE: PRT
<213> ORGANISM: Artificial Sequence
<220> FEATURE:
<223> OTHER INFORMATION: Synthetic

<400> SEQUENCE: 380

```
Ile Gly Tyr Asp Gly Gly Asn Glu
1               5
```

<210> SEQ ID NO 381
<211> LENGTH: 42
<212> TYPE: DNA
<213> ORGANISM: Artificial Sequence
<220> FEATURE:

<223> OTHER INFORMATION: Synthetic

<400> SEQUENCE: 381
tcgactataa gtcattacga tattttgagc ggtatggacg tc                            42

<210> SEQ ID NO 382
<211> LENGTH: 14
<212> TYPE: PRT
<213> ORGANISM: Artificial Sequence
<220> FEATURE:
<223> OTHER INFORMATION: Synthetic

<400> SEQUENCE: 382

Ser Thr Ile Ser His Tyr Asp Ile Leu Ser Gly Met Asp Val
1               5                   10

<210> SEQ ID NO 383
<211> LENGTH: 324
<212> TYPE: DNA
<213> ORGANISM: Artificial Sequence
<220> FEATURE:
<223> OTHER INFORMATION: Synthetic

<400> SEQUENCE: 383
gacatccaga tgacccagtc tccatcttcc gtgtctgcat ctgtaggaga cagagtcacc         60
atcacttgtc gggcgagtca gggtattagc aactggttag cctggtatca gcagaaacca        120
gggaaagccc ctaagctcct gatctttgct gcatccagtt tgcaaagtgg ggtcccatca        180
cggttcagcg gcagtgcatc tgggacagat ttcactctca ccatcaacag cctgcagcct        240
gaagattttg caacttacta ttgtcaacag gctaacagtt tcccgctcac tttcggcgga        300
gggaccaagg tggagatcaa acga                                              324

<210> SEQ ID NO 384
<211> LENGTH: 108
<212> TYPE: PRT
<213> ORGANISM: Artificial Sequence
<220> FEATURE:
<223> OTHER INFORMATION: Synthetic

<400> SEQUENCE: 384

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Phe Ala Ala Ser Ser Leu Gln Ser Gly Val Pro Ser Arg Phe Ser Gly
    50                  55                  60

Ser Ala Ser Gly Thr Asp Phe Thr Leu Thr Ile Asn Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys Arg
            100                 105

<210> SEQ ID NO 385
<211> LENGTH: 18
<212> TYPE: DNA
<213> ORGANISM: Artificial Sequence
<220> FEATURE:
<223> OTHER INFORMATION: Synthetic

```
<400> SEQUENCE: 385
cagggtatta gcaactgg                                                    18

<210> SEQ ID NO 386
<211> LENGTH: 6
<212> TYPE: PRT
<213> ORGANISM: Artificial Sequence
<220> FEATURE:
<223> OTHER INFORMATION: Synthetic

<400> SEQUENCE: 386

Gln Gly Ile Ser Asn Trp
1               5

<210> SEQ ID NO 387
<211> LENGTH: 9
<212> TYPE: DNA
<213> ORGANISM: Artificial Sequence
<220> FEATURE:
<223> OTHER INFORMATION: Synthetic

<400> SEQUENCE: 387 gctgcatcc                                                               9

<210> SEQ ID NO 388
<211> LENGTH: 3
<212> TYPE: PRT
<213> ORGANISM: Artificial Sequence
<220> FEATURE:
<223> OTHER INFORMATION: Synthetic

<400> SEQUENCE: 388

Ala Ala Ser
1

<210> SEQ ID NO 389
<211> LENGTH: 27
<212> TYPE: DNA
<213> ORGANISM: Artificial Sequence
<220> FEATURE:
<223> OTHER INFORMATION: Synthetic

<400> SEQUENCE: 389
caacaggcta acagtttccc gctcact                                           27

<210> SEQ ID NO 390
<211> LENGTH: 9
<212> TYPE: PRT
<213> ORGANISM: Artificial Sequence
<220> FEATURE:
<223> OTHER INFORMATION: Synthetic

<400> SEQUENCE: 390

Gln Gln Ala Asn Ser Phe Pro Leu Thr
1               5

<210> SEQ ID NO 391
<211> LENGTH: 340
<212> TYPE: PRT
<213> ORGANISM: Artificial Sequence
<220> FEATURE:
<223> OTHER INFORMATION: Synthetic

<400> SEQUENCE: 391

Glu Ala Glu Thr Arg Glu Cys Ile Tyr Tyr Asn Ala Asn Trp Glu Leu
```

```
1               5                    10                   15
Glu Arg Thr Asn Gln Ser Gly Leu Glu Arg Cys Glu Gly Glu Gln Asp
            20                  25                  30

Lys Arg Leu His Cys Tyr Ala Ser Trp Ala Asn Ser Ser Gly Thr Ile
            35              40                  45

Glu Leu Val Lys Lys Gly Cys Trp Leu Asp Asp Phe Asn Cys Tyr Asp
            50              55                  60

Arg Gln Glu Cys Val Ala Thr Glu Glu Asn Pro Gln Val Tyr Phe Cys
65                      70                  75                  80

Cys Cys Glu Gly Asn Phe Cys Asn Glu Arg Phe Thr His Leu Pro Glu
                85                  90                  95

Ala Gly Gly Pro Glu Val Thr Tyr Glu Pro Pro Thr Ala Pro Ser
                    100                 105                 110

Gly Asp Lys Thr His Thr Cys Pro Pro Cys Pro Ala Pro Glu Leu Leu
            115                 120                 125

Gly Gly Pro Ser Val Phe Leu Phe Pro Pro Lys Pro Lys Asp Thr Leu
            130                 135                 140

Met Ile Ser Arg Thr Pro Glu Val Thr Cys Val Val Val Asp Val Ser
145                 150                 155                 160

His Glu Asp Pro Glu Val Lys Phe Asn Trp Tyr Val Asp Gly Val Glu
                    165                 170                 175

Val His Asn Ala Lys Thr Lys Pro Arg Glu Glu Gln Tyr Asn Ser Thr
                180                 185                 190

Tyr Arg Val Val Ser Val Leu Thr Val Leu His Gln Asp Trp Leu Asn
                195                 200                 205

Gly Lys Glu Tyr Lys Cys Lys Val Ser Asn Lys Ala Leu Pro Ala Pro
        210                 215                 220

Ile Glu Lys Thr Ile Ser Lys Ala Lys Gly Gln Pro Arg Glu Pro Gln
225                 230                 235                 240

Val Tyr Thr Leu Pro Pro Ser Arg Asp Glu Leu Thr Lys Asn Gln Val
                245                 250                 255

Ser Leu Thr Cys Leu Val Lys Gly Phe Tyr Pro Ser Asp Ile Ala Val
                260                 265                 270

Glu Trp Glu Ser Asn Gly Gln Pro Glu Asn Asn Tyr Lys Thr Thr Pro
        275                 280                 285

Pro Val Leu Asp Ser Asp Gly Ser Phe Phe Leu Tyr Ser Lys Leu Thr
        290                 295                 300

Val Asp Lys Ser Arg Trp Gln Gln Gly Asn Val Phe Ser Cys Ser Val
305                 310                 315                 320

Met His Glu Ala Leu His Asn His Tyr Thr Gln Lys Ser Leu Ser Leu
                    325                 330                 335

Ser Pro Gly Lys
            340
```

METHODS FOR INCREASING LEAN BODY MASS WITH RESISTANCE TRAINING AND A GDF8 INHIBITOR THAT IS AN ANTI-GDF8 ANTIBODY

CROSS-REFERENCE TO RELATED APPLICATIONS

This application claims the benefit of U.S. Provisional Application No. 62/147,853, filed Apr. 15, 2015, and U.S. Provisional Application No. 62/234,899, filed Sep. 30, 2015, and U.S. Provisional Application No. 62/261,528, filed Dec. 1, 2015. The disclosures of which are incorporated herein in their entirety.

INTRODUCTION

A decrease in skeletal muscle mass appears to play a significant pathological role in the progression of a wide variety of disorders associated with aging, frailty, and certain metabolic conditions. In the elderly, conditions such as sarcopenia and specific events such as a hip fracture may be directly tied to a significant loss of global muscle mass. In both older and younger populations, the recovery from immobilization and orthopedic surgeries may be linked to the degree of acute muscle loss associated with both muscle disuse and atrophy driven by the procedure. In addition, the gain or maintenance of skeletal muscle mass can result in the prevention of obesity as well as metabolic improvements.

Myostatin or growth differentiation factor 8 (GDF8) is a soluble TGF-β superfamily ligand. It is a negative regulator of muscle growth expressed principally in skeletal muscle but low expression has been reported in other tissues such as heart and adipose, at levels approximately 100-fold lower than that seen in skeletal muscle (McPherron Nature 387:83, 1997, Sharma J. Cell. Phys. 180:1, 1999, Lee Annrev. Cell Dev. Biol. 20:61, 2004, Allen Pysiol. Rev. 88:257, 2008, Heineke Cir. 121:419, 2010). Mature myostatin is highly conserved among species, and inactivating mutations of the myostatin gene leads to a hypermuscular phenotype in multiple species including mice, cattle, dogs, and humans. Conversely, overexpression of myostatin in mice (by injection of transfected CHO cells into thighs of athymic mice or generation of striated muscle transgenic mice) caused a significant decrease in body mass due to decrease in muscle fiber size (McPherron 1997 cited supra, Grobet Nat. Genet. 17:71, 1997, Mosher PLOS Genet. 3:e79, 2007, Schuelke NEJM 350:2682, 2004). While the myostatin null mouse phenotype demonstrates the importance of myostatin in the control of muscle size during development, hypertrophy can also be elicited in adult muscle through inhibition of myostatin by neutralizing antibodies, decoy receptors, or other antagonists. However, the effects on myostatin inhibitors on cardiac tissue in function may provide an undesirable side effect profile for use of these inhibitors to treat conditions like sarcopenia, and metabolic conditions.

Methods of Increasing Strength and Functionality with GDF8 Inhibitors

This disclosure provides methods and formulations for use in the methods as described herein. GDF8 inhibitors are useful to enhance lean muscle mass in a subject, for example, in combination with exercise. In some embodiments, the subject is a subject that that does not have a disease or disorder that significantly limits the subject's ability to participate in resistance training. In embodiments, the disease or disorder is one in which a physician has recommended limited physical activity for the subject or in which exercise is contraindicated such as uncontrolled diabetes, recent myocardial infarction, unstable cardiac conditions, acute heart failure, severe myocarditis, uncontrolled hypertension, cardiac valve disease requiring surgery, and severe aortic stenosis.

In embodiments, a method for increasing lean body mass in a subject comprises providing an exercise regimen for the subject, and administering a composition comprising an effective amount of a GDF-8 inhibitor wherein, the effective amount is at least 400 mg. In embodiments, the exercise regimen includes, without limitation, resistance training, weight training, yoga, aerobic exercise, and pilates. In embodiments, a GDF8 inhibitor is an antibody or antigen binding fragment that specifically binds GDF8. In embodiments, the antibody or antigen binding fragment comprises heavy chain CDRs contained within a heavy chain variable region selected from the group consisting of SEQ ID NO: 2, SEQ ID NO: 18, SEQ ID NO: 34, SEQ ID NO: 50, SEQ ID NO: 66, SEQ ID NO: 82, SEQ ID NO: 98, SEQ ID NO: 114, SEQ ID NO: 130, SEQ ID NO: 146, SEQ ID NO: 162, SEQ ID NO: 178, SEQ ID NO: 194, SEQ ID NO: 210, SEQ ID NO: 226, SEQ ID NO: 242, SEQ ID NO: 258, SEQ ID NO: 274, SEQ ID NO: 290, SEQ ID NO: 306, SEQ ID NO: 360, and SEQ ID NO: 376. In embodiments, the method further comprises an antibody or antigen binding fragment that comprises light chain CDRS contained within a light chain variable regions selected from the group consisting of SEQ ID NOs: SEQ ID NO: 10, SEQ ID NO: 26, SEQ ID NO: 42, SEQ ID NO: 58, SEQ ID NO: 74, SEQ ID NO: 90, SEQ ID NO: 106, SEQ ID NO: 122, SEQ ID NO: 138, SEQ ID NO: 154, SEQ ID NO: 170, SEQ ID NO: 186, SEQ ID NO: 202, SEQ ID NO: 218, SEQ ID NO: 234, SEQ ID NO: 250, SEQ ID NO: 266, SEQ ID NO: 282, SEQ ID NO: 298, SEQ ID NO: 314, SEQ ID NO: 322, SEQ ID NO: 368, and SEQ ID NO: 384.

In embodiments, compositions are formulated to contain an effective amount of a GDF8 inhibitor to increase lean muscle mass. In embodiments, an effective amount is at least 0.1 mg/kg to about 10 gm/kg, 1 mg/kg to about 1 gm/kg, or 10 mg/kg to 100 mg/kg. In embodiments, the composition is administered at least once a week, twice a week, three times a week, four times a week, or five times a week. In embodiments, the exercise regimen is followed for at least 12 weeks. In embodiments, the compositions are formulated for intravenous, subcutaneous, or oral administration.

BRIEF DESCRIPTION OF THE FIGURES

FIG. 1 (B) shows the percent change in lean muscle mass per study visit per group in subjects receiving Placebo alone (third line from top), Placebo plus resistance training (RT)(bottom line), 400 mg SC of REGN1033 alone, for a total of 6 doses over the study period (second line from top), and 400 mg SC of REGN1033 plus RT (top line), for a total of 6 doses over the study period.

FIG. 3 (A) shows percent change in thigh muscle mass including intramuscular fat per study visit per group in subjects receiving Placebo alone (third line from top), Placebo plus resistance training (RT)(bottom line), 400 mg SC of REGN1033 alone, for a total of 6 doses over the study period (second line from top), and 400 mg SC of REGN1033 plus RT (top line), for a total of 6 doses over the study period. FIG. 3 (B) shows percent change in thigh muscle mass excluding intramuscular fat per study visit per group in subjects receiving Placebo alone (third line from top), Placebo plus resistance training (RT) (bottom line), 400 mg SC of REGN1033 alone, for a total of 6 doses over the study period (second line from top), and 400 mg SC of REGN1033 plus RT (top line), for a total of 6 doses over the study period. Placebo alone and Placebo plus RT lines overlap one another.

FIG. 5 shows percent change in chest press per study visit per group in subjects receiving Placebo alone (bottom line), Placebo plus resistance training (RT)(third line from top), 400 mg SC of REGN1033 alone, for a total of 6 doses over the study period (second line from top), and 400 mg SC of REGN1033 plus RT (top line), for a total of 6 doses over the study period.

DETAILED DESCRIPTION

Figure 1A:
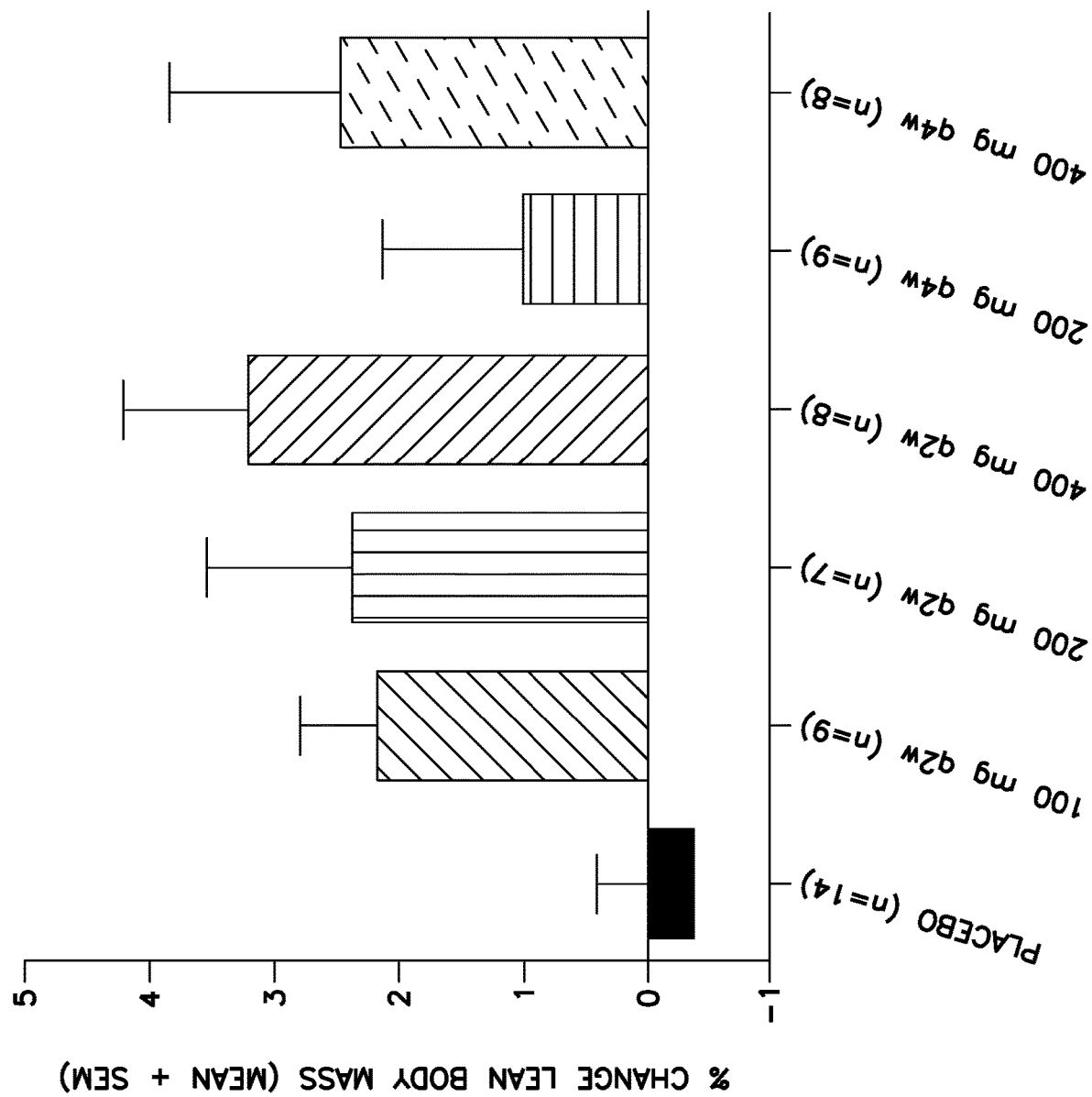
FIG. 1 (A) shows the results of the MAD study designed to assesses the safety, tolerability, pharmacokinetics (PK), immunogenicity, and pharmacodynamic (PD) effects of REGN1033 (anti-GDF8 antibody) administered subcutaneously (SC) in healthy volunteers 60 years of age and older. A total of 5 cohorts with 12 subjects enrolled in each cohort were studied. Subjects received SC doses of REGN1033 (n=9) or placebo (n=14). The planned REGN1033 dose regimens were 100, 200, or 400 mg Q2W for a total of 6 doses per subject and 200 mg or 400 mg Q4W for a total of 3 doses per subject. The % lean body mass was determined using dual energy x-ray absorptiometry (DEXA).

Before the present methods are described, it is to be understood that this disclosure is not limited to particular methods, and experimental conditions described, as such methods and conditions may vary. It is also to be understood that the terminology used herein is for the purpose of describing particular embodiments only, and is not intended to be limiting, since the scope of the invention will be limited only by the appended claims.

As used in this specification and the appended claims, the singular forms "a", "an", and "the" include plural references unless the context clearly dictates otherwise. Thus for example, a reference to "a method" includes one or more methods, and/or steps of the type described herein and/or which will become apparent to those persons skilled in the art upon reading this disclosure.

Unless defined otherwise, all technical and scientific terms used herein have the same meaning as commonly understood by one of ordinary skill in the art to which this invention belongs.

As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the invention, the preferred methods and materials are now described. All patents, applications and non-patent publications mentioned in this specification are incorporated herein by reference in their entireties.

Definitions

"Human Growth Differentiation Factor-8", "GDF8" and "myostatin" are used interchangeably to refer to the protein encoded by the nucleic acid sequence of SEQ ID NO: 338 and the protein having the amino acid sequence of SEQ ID NO: 339 (propeptide) and SEQ ID NO: 340 (mature protein).

The term "antibody", as used herein, is intended to refer to immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-GDF8 antibody (or antigen-binding portion thereof) may be identical to the human germline sequences, or may be naturally or artificially modified. An amino acid consensus sequence may be defined based on a side-by-side analysis of two or more CDRs.

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')$_2$ fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR)). Other engineered molecules, such as diabodies, triabodies, tetrabodies and minibodies, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a VH domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the invention include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the invention may comprise a homo-dimer or hetero-dimer (or other multimer) of any of the variable and constant domain configurations listed above in non-covalent association with one another and/or with one or more monomeric VH or VL domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the invention using routine techniques available in the art.

The antibodies of the invention may function through complement-dependent cytotoxicity (CDC) or antibody-dependent cell-mediated cytotoxicity (ADCC). "Complement-dependent cytotoxicity" (CDC) refers to lysis of antigen-expressing cells by an antibody of the invention in the presence of complement. "Antibody-dependent cell-mediated cytotoxicity" (ADCC) refers to a cell-mediated reaction in which nonspecific cytotoxic cells that express Fc receptors (FcRs) (e.g., Natural Killer (NK) cells, neutrophils, and macrophages) recognize bound antibody on a target cell and thereby lead to lysis of the target cell. CDC and ADCC can be measured using assays that are well known and available in the art. (See, e.g., U.S. Pat. Nos. 5,500,362 and 5,821,337, and Clynes et al., Proc. Natl. Acad. Sci. (USA) 95:652-656 (1998)).

The term "specifically binds," or the like, means that an antibody or antigen-binding fragment thereof forms a complex with an antigen that is relatively stable under physiologic conditions. Specific binding can be characterized by a dissociation constant of $1 \times 10^{-6}$ M or less. Methods for determining whether two molecules specifically bind are well known in the art and include, for example, equilibrium dialysis, surface plasmon resonance, and the like. For example, an antibody that "specifically binds" human GDF8, as used in the context of the invention, includes antibodies that bind human GDF8 or portion thereof (e.g., a peptide comprising at least 6 contiguous amino acids of SEQ ID NO:340) with a $K_D$ of less than about 1000 nM, less than about 500 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 4 nM, less than about 3 nM, less than about 2 nM, less than about 1 nM or less than about 0.5 nM, as measured in a surface plasmon resonance assay. (See, e.g., Example 3, herein). An isolated antibody that specifically binds human GDF8 may, however, have cross-reactivity to other antigens, such as GDF8 molecules from other species.

The term "high affinity" antibody refers to those antibodies capable of binding to GDF8 with a dissociation constant ($K_D$) of about $10^{-8}$ M or less, about $10^{-9}$ M or less, about $10^{-10}$ M or less, about $10^{-11}$ M or less, or about $10^{-12}$ M or less, as measured by surface plasmon resonance, e.g., BIACORE™ or solution-affinity ELISA.

By the term "slow off rate" or "Koff" is meant an antibody that dissociates from GDF8 with a rate constant of $1 \times 10^{-3}$ s$^{-1}$ or less, preferably $1 \times 10^{-4}$ s$^{-1}$ or less, as determined by surface plasmon resonance, e.g., BIACORE™.

A "neutralizing" or "blocking" antibody, is intended to refer to an antibody whose binding to GDF8 results in inhibition of the biological activity of GDF8. This inhibition of the biological activity of GDF8 can be assessed by measuring one or more indicators of GDF8 biological activity. These indicators of GDF8 biological activity can be assessed by one or more of several standard in vitro or in vivo assays known in the art.

As used herein, the expression "anti-GDF8 antibody" also includes multispecific antigen-binding molecules (e.g., bispecific antibodies) wherein at least one binding domain (e.g., "binding arm") of the multispecific antigen-binding molecule specifically binds GDF8.

Exemplary anti-GDF8 antibodies that can be used in the context of the invention include, e.g., the fully-human anti-GDF8 antibody H4H1657N2 (Regeneron/Sanofi) (e.g., an anti-GDF8 antibody comprising the heavy and light chain variable regions having amino acid sequences SEQ ID NO: 360 and SEQ ID NO: 368, respectively, as set forth in U.S. Pat. No. 8,840,894). Other GDF8 antagonists that can be used in the context of the methods of the invention include anti-GDF8 antibodies (e.g., the antibody designated 2_112_1 (ATCC deposit designation PTA-6574)) as set forth in U.S. Pat. No. 7,807,159, anti-GDF8 antibodies (e.g. 12A5-5) as set forth in U.S. Pat. No. 8,999,343 and US Publication No. 2013/0209489, anti-GDF8 antibodies (e.g., 10B3H8L5 and 10B3H8L5-Fc-disabled) as set forth in US Publication No. 2013/0142788, the anti-GDF8 antibody stamulumab/MYO-29 as set forth in, e.g., U.S. Pat. No. 8,940,874, anti-GDF8 antibodies (e.g., RK22/PF-0625616) as set forth in U.S. Pat. No. 8,415,459, anti-GDF8 antibodies (e.g., JA-16) as set forth in U.S. Pat. No. 7,731,961, anti- GDF8 antibodies (e.g., RK35) as set forth in U.S. Pat. No. 8,496,934, anti-GDF8 antibodies (e.g., OGD1.0.0) as set forth in U.S. Pat. No. 8,992,913, anti-GDF8 Fab molecules as set forth in European Patent No. 1 773 041 B1, anti-GDF8 antibodies (e.g., 41C1E4) as set forth in U.S. Pat. No. 7,632,499, and anti-GDF8 antibodies (e.g., C12, C12-N93H and/or 510C2) as set forth in, e.g., U.S. Pat. Nos. 7,635,760 and 8,063,188. The disclosures of all of the aforementioned patents and patent application publications are incorporated by reference herein in their entireties The fully-human anti-GDF8 antibodies disclosed herein may comprise one or more amino acid substitutions, insertions and/or deletions in the framework and/or CDR regions of the heavy and light chain variable domains as compared to the corresponding germline sequences. Such mutations can be readily ascertained by comparing the amino acid sequences disclosed herein to germline sequences available from, for example, public antibody sequence databases. The invention includes antibodies, and antigen-binding fragments thereof, which are derived from any of the amino acid sequences disclosed herein, wherein one or more amino acids within one or more framework and/or CDR regions are back-mutated to the corresponding germline residue(s) or to a conservative amino acid substitution (natural or non-natural) of the corresponding germline residue(s) (such sequence changes are referred to herein as "germline back-mutations"). A person of ordinary skill in the art, starting with the heavy and light chain variable region sequences disclosed herein, can easily produce numerous antibodies and antigen-binding fragments which comprise one or more individual germline back-mutations or combinations thereof. In certain embodiments, all of the framework and/or CDR residues within the $V_H$ and/or $V_L$ domains are mutated back to the germline sequence. In other embodiments, only certain residues are mutated back to the germline sequence, e.g., only the mutated residues found within the first 8 amino acids of FR1 or within the last 8 amino acids of FR4, or only the mutated residues found within CDR1, CDR2 or CDR3. Furthermore, the antibodies of the invention may contain any combination of two or more germline back-mutations within the framework and/or CDR regions, i.e., wherein certain individual residues are mutated back to the germline sequence while certain other residues that differ from the germline sequence are maintained. Once obtained, antibodies and antigen-binding fragments that contain one or more germline back-mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the invention.

The invention also includes anti-GDF8 antibodies comprising variants of any of the HCVR, LCVR, and/or CDR amino acid sequences disclosed herein having one or more conservative substitutions. For example, the invention includes anti-GDF8 antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein. In one embodiment, the antibody comprises an HCVR having an amino acid sequence selected from SEQ ID NO:360 and 376 with 8 or fewer conservative amino acid substitutions. In another embodiment, the antibody comprises an HCVR having an amino acid sequence selected from SEQ ID NO:360 and 376 with 6 or fewer conservative amino acid substitutions. In another embodiment, the antibody comprises an HCVR having an amino acid sequence selected from SEQ ID NO:360 and 376 with 4 or fewer conservative amino acid substitutions. In another embodiment, the antibody comprises an HCVR having an amino acid sequence selected from SEQ ID NO:360 and 376 with 2 or fewer conservative amino acid substitutions. In one embodiment, the antibody comprises an LCVR having an amino acid sequence selected from SEQ ID NO:368 and 384 with 8 or fewer conservative amino acid substitutions. In another embodiment, the antibody comprises an LCVR having an amino acid sequence selected from SEQ ID NO:368 and 384 with 6 or fewer conservative amino acid substitutions. In another embodiment, the antibody comprises an LCVR having an amino acid sequence selected from SEQ ID NO:368 and 384 with 4 or fewer conservative amino acid substitutions. In another embodiment, the antibody comprises an LCVR having an amino acid sequence selected from SEQ ID NO:368 and 384 with 2 or fewer conservative amino acid substitutions.

In certain embodiments, antibody or antibody fragment of the invention may be conjugated to a therapeutic moiety ("immunoconjugate"), such as a cytotoxin, a chemotherapeutic drug, and immunosuppressant or a radioisotope.

An "isolated antibody," as used herein, means an antibody that has been identified and separated and/or recovered from at least one component of its natural environment. For example, an antibody that has been separated or removed from at least one component of an organism, tissue or cell in which the antibody naturally exists or is naturally produced is an "isolated antibody" for purposes of the invention. An isolated antibody also includes an antibody in situ within a recombinant cell, as well as an antibody that has been subjected to at least one purification or isolation step. According to certain embodiments, an isolated antibody may be substantially free of other cellular material and/or chemicals.

The term "surface plasmon resonance", as used herein, refers to an optical phenomenon that allows for the analysis of real-time biospecific interactions by detection of alterations in protein concentrations within a biosensor matrix, for example using the BIACORE™ system (Pharmacia Biosensor AB, Uppsala, Sweden and Piscataway, N.J.).

The term "$K_D$", as used herein, is intended to refer to the equilibrium dissociation constant of a particular antibody-antigen interaction.

The term "epitope" includes any determinant, preferably a polypeptide determinant, capable of specific binding to an immunoglobulin or T-cell receptor. In certain embodiments, epitope determinants include chemically active surface groupings of molecules such as amino acids, sugar side chains, phosphoryl groups, or sulfonyl groups, and, in certain embodiments, may have specific three-dimensional structural characteristics, and/or specific charge characteristics. An epitope is a region of an antigen that is bound by an antibody. In certain embodiments, an antibody is said to specifically bind an antigen when it preferentially recognizes its target antigen in a complex mixture of proteins and/or macromolecules. For example, an antibody is said to specifically bind an antigen when the $K_D$ is less than or equal to $10^{-8}$ M, less than or equal to $10^{-9}$ M, or less than or equal to $10^{-10}$ M.

A protein or polypeptide is "substantially pure," "substantially homogeneous" or "substantially purified" when at least about 60 to 75% of a sample exhibits a single species of polypeptide. The polypeptide or protein may be monomeric or multimeric. A substantially pure polypeptide or protein will typically comprise about 50%, 60, 70%, 80% or 90% w/w of a protein sample, usually about 95%, and preferably over 99% pure. Protein purity or homogeneity may be indicated by a number of means well known in the art, such as polyacrylamide gel electrophoresis of a protein sample, followed by visualizing a single polypeptide band upon staining the gel with a stain well known in the art. For certain purposes, higher resolution may be provided by using HPLC or other means well known in the art for purification.

The term "polypeptide analog or variant" as used herein refers to a polypeptide that is comprised of a segment of at least 25 amino acids that has substantial identity to a portion of an amino acid sequence and that has at least one of the following properties: (1) specific binding to GDF8 under suitable binding conditions, or (2) ability to block the biological activity of GDF8. Typically, polypeptide analogs or variants comprise a conservative amino acid substitution (or insertion or deletion) with respect to the naturally-occurring sequence. Analogs typically are at least 20 amino acids long, at least 50, 60, 70, 80, 90, 100, 150 or 200 amino acids long or longer, and can often be as long as a full-length naturally-occurring polypeptide.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various mutations of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton 1984 W. H. Freeman and Company, New York; Introduction to Protein Structure (Branden & Tooze, eds., 1991, Garland Publishing, NY); and Thornton et at. 1991 Nature 354:105, which are each incorporated herein by reference.

Non-peptide analogs are commonly used in the pharmaceutical industry as drugs with properties analogous to those of the template peptide. These types of non-peptide compound are termed "peptide mimetics" or "peptidomimetics" (see, for example, Fauchere (1986) J. Adv. Drug Res. 15:29; and Evans et al. (1987) J. Med. Chem. 30:1229, which are incorporated herein by reference. Systematic substitution of one or more amino acids of a consensus sequence with a D-amino acid of the same type (e.g., D-lysine in place of L-lysine) may also be used to generate more stable peptides. In addition, constrained peptides comprising a consensus sequence or a substantially identical consensus sequence variation may be generated by methods known in the art (Rizo et al. (1992) Ann. Rev. Biochem. 61:387, incorporated herein by reference), for example, by adding internal cysteine residues capable of forming intramolecular disulfide bridges which cyclize the peptide.

As applied to polypeptides, the term "substantial identity" or "substantially identical" means that two peptide sequences, when optimally aligned, such as by the programs GAP or BESTFIT using default gap weights, share at least about 80% sequence identity, at least about 90%, at least about 95%, at least about 98% or at least about 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24:307-331, herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; and 6) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256:1443-45, herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000), supra). Another preferred algorithm when comparing a sequence of the invention to a database containing a large number of sequences from different organisms is the computer program BLAST, especially blastp or tblastn, using default parameters. See, e.g., Altschul et al. (1990) J. Mol. Biol. 215:403-410 and Altschul et al. (1997) Nucleic Acids Res. 25:3389 402, each of which is herein incorporated by reference.

The length of polypeptide sequences compared for homology will generally be at least about 16 amino acid residues, at least about 20 residues, at least about 24 residues, at least about 28 residues, or at least about 35 residues. When searching a database containing sequences from a large number of different organisms, it is preferable to compare amino acid sequences.

The term "effective amount" is a concentration or amount of an antibody or antigen-binding fragment of an antibody which results in achieving a particular stated purpose. An "effective amount" of an anti-GDF8 antibody or antigen-binding fragment of an antibody thereof may be determined empirically. Furthermore, a "therapeutically effective amount" is a concentration or amount of an anti-GDF8 antibody or antigen-binding fragment thereof which is effective for achieving a stated therapeutic effect. This amount may also be determined empirically.

As used herein, a "healthy subject" refers to a subject that does not have a disease or disorder that significantly limits the subject's ability to participate in resistance training. In embodiments, the disease or disorder is one in which a physician has recommended limited physical activity for the subject or in which exercise is contraindicated such as uncontrolled diabetes, recent myocardial infarction, unstable cardiac conditions, acute heart failure, severe myocarditis, uncontrolled hypertension, cardiac valve disease requiring surgery, and severe aortic stenosis.

As used herein, "resistance training" refers to a set of exercises that causes a muscle to contract against an external resistance. The external resistance includes for example, a weight, a band, a kettleball, or the subject's body weight.

As used herein, "exercise regimen" refers to a plan of exercises. In embodiments, an exercise regimen includes exercises, such as, resistance training, weigh training, aerobic training, walking, interval training, yoga, and combinations thereof.

ASPECTS OF THE DISCLOSURE

The disclosure provides compositions, kits, and methods of using GDF-8 inhibitors to increase lean body mass. In embodiments, the GDF-8 inhibitor is an antibody or antigen binding fragment thereof that specifically binds GDF-8.

Preparation of Human Antibodies

Methods for generating monoclonal antibodies, including fully human monoclonal antibodies are known in the art. Any such known methods can be used in the context of the invention to make human antibodies that specifically bind to GDF8.

Using VELOCIMMUNE™ technology or any other known method for generating monoclonal antibodies, high affinity chimeric antibodies to GDF8 are initially isolated having a human variable region and a mouse constant region. As in the experimental section below, the antibodies are characterized and selected for desirable characteristics, including affinity, selectivity, epitope, etc. The mouse constant regions are replaced with a desired human constant region to generate the fully human antibody of the invention, for example wild-type or modified IgG1 or IgG4. While the constant region selected may vary according to specific use, high affinity antigen-binding and target specificity characteristics reside in the variable region.

In general, the antibodies of the instant invention possess very high affinities, typically possessing $K_D$ of from about $10^{-12}$ through about $10^{-9}$ M, when measured by binding to antigen either immobilized on solid phase or in solution phase. The mouse constant regions are replaced with desired human constant regions to generate the fully human antibodies of the invention, for example wild-type IgG1 (SEQ ID NO: 335) or IgG4 (SEQ ID NO: 336), or modified IgG1 or IgG4 (for example, SEQ ID NO: 337). While the constant region selected may vary according to specific use, high affinity antigen-binding and target specificity characteristics reside in the variable region.

Antibodies or Antigen Binding Fragments Specific for GDF-8

The invention includes anti-GDF8 antibodies and antigen-binding fragments of antibodies which bind specific epitopes of human GDF8 (SEQ ID NO:340) and are capable of blocking the biological activity of GDF8. In one embodiment, the antibody or antigen-binding fragment thereof binds within an epitope comprising amino acids residues 1 to 109; 1 to 54; 1 to 44; 1 to 34; 1 to 24; and 1 to 14. In another embodiment, the antibody or antigen-binding fragment thereof binds within an epitope comprising of amino acid residues 65 to 72; 35 to 109; 45 to 109; 55 to 109; 65 to 109; 75 to 109; 85 to 109; 92 to 109; or 95 to 109. In another embodiment, the antibody or antigen-binding fragment thereof binds within an epitope comprising amino acid residue 48 to 72; 48 to 69; 48 to 65; 52 to 72; 52 to 65; or 56 to 65. In specific embodiments, the antibody or antigen-binding fragment thereof may bind within 2 or more epitopes.

The invention also includes antibodies and antigen-binding fragments thereof that bind wild-type mature GDF8 (SEQ ID NO: 340) but do not bind isolated peptides having less than the full amino acid sequence of SEQ ID NO: 340. For example, the invention includes anti-GDF8 antibodies that bind wild-type mature GDF8 (SEQ ID NO: 340) but do not bind isolated peptides consisting of 10 to 40 contiguous amino acids of SEQ ID NO: 340. The invention also includes anti-GDF8 antibodies that do not bind any linear epitopes within wild-type mature GDF8. In certain embodiments of the invention, the anti-GDF8 antibodies bind wild-type mature human GDF8 comprising SEQ ID NO: 340 but do not bind one or more isolated GDF8 peptides having an amino acid sequence selected from the group consisting of amino acids 1-14, 1-18, 17-42, 48-65, 48-69, 48-72, 52-65, 52-72, 56-65, 56-72, 65-72, 73-90, 75-105 and 91-105, of SEQ ID NO:340. In certain embodiments, the anti-GDF8 antibodies do not bind any of the aforementioned GDF8 peptides. Methods for determining whether a given antibody is able to bind a particular GDF8 peptide are known to persons of ordinary skill in the art.

The invention also includes isolated human antibodies, or antigen-binding fragments thereof, that specifically bind to wild-type mature human GDF8 (e.g., a protein or polypeptide comprising SEQ ID NO: 340), but do not bind to a chimeric GDF8 construct in which certain amino acids of GDF8 are replaced with the corresponding amino acid sequence(s) from a non-identical but related protein such as TGFβ-1. In one example, the chimeric construct is a GDF8/TGFβ-1 chimera in which amino acids 48-72 of mature GDF8 are replaced with the corresponding amino acid sequence of TGFβ-1 (e.g., amino acids 49-76 of TGFβ-1). An example of one such chimera is represented by SEQ ID NO: 352. Thus, in certain embodiments, the antibodies of the invention specifically bind to wild-type mature human GDF8 (SEQ ID NO: 340) but do not bind to the chimeric GDF8/TGFβ-1 construct of SEQ ID NO: 352, indicating that the epitope to which such antibodies bind includes or encompasses amino acids located within residues 48 to 72 of SEQ ID NO: 340. Blocking bioassays can also be used to indirectly ascertain if an antibody binds wild-type mature human GDF8 (SEQ ID NO: 340) and does not bind a chimeric GDF8/TGFβ-1 construct, e.g., the construct of SEQ ID NO: 352. For example, an antibody which blocks the bioactivity of wild-type mature human GDF8 but does not block the bioactivity of a chimeric GDF8/TGFβ-1 is deemed to bind to the portion of GDF8 that is replaced by the corresponding TGFβ-1 sequence in the chimeric construct.

Similarly, the invention also includes isolated human antibodies, or antigen-binding fragments thereof, that block wild-type mature GDF8-mediated activity in a bioassay but do not block activity of a chimeric GDF8 construct (e.g., a GDF8/TGFβ-1 chimera in which amino acids 48-72 of mature GDF8 are replaced with the corresponding amino acid sequence of TGFβ-1 (e.g., amino acids 49-76 of TGFβ-1).

The invention includes anti-GDF8 antibodies that bind to the same epitope as any of the specific exemplary antibodies described herein. Likewise, the invention also includes anti-GDF8 antibodies that cross-compete for binding to GDF8 or a GDF8 fragment with any of the specific exemplary antibodies described herein.

One can easily determine whether an antibody binds to the same epitope as, or competes for binding with, a reference anti-GDF8 antibody by using routine methods known in the art. For example, to determine if a test antibody binds to the same epitope as a reference anti-GDF8 antibody of the invention, the reference antibody is allowed to bind to a GDF8 protein or peptide under saturating conditions. Next, the ability of a test antibody to bind to the GDF8 molecule is assessed. If the test antibody is able to bind to GDF8 following saturation binding with the reference anti-GDF8 antibody, it can be concluded that the test antibody binds to a different epitope than the reference anti-GDF8 antibody. On the other hand, if the test antibody is not able to bind to the GDF8 molecule following saturation binding with the reference anti-GDF8 antibody, then the test antibody may bind to the same epitope as the epitope bound by the reference anti-GDF8 antibody of the invention. Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, MA, Biacore, flow cytometry or any other quantitative or qualitative antibody-binding assay available in the art. In accordance with certain embodiments of the invention, two antibodies bind to the same (or overlapping) epitope if, e.g., a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990:50:1495-1502). Alternatively, two antibodies are deemed to bind to the same epitope if essentially all amino acid mutations in the antigen that reduce or eliminate binding of one antibody reduce or eliminate binding of the other. Two antibodies are deemed to have "overlapping epitopes" if only a subset of the amino acid mutations that reduce or eliminate binding of one antibody reduce or eliminate binding of the other.

To determine if an antibody competes for binding with a reference anti-GDF8 antibody, the above-described binding methodology is performed in two orientations: In a first orientation, the reference antibody is allowed to bind to a GDF8 molecule under saturating conditions followed by assessment of binding of the test antibody to the GDF8 molecule. In a second orientation, the test antibody is allowed to bind to a GDF8 molecule under saturating conditions followed by assessment of binding of the reference antibody to the GDF8 molecule. If, in both orientations, only the first (saturating) antibody is capable of binding to the GDF8 molecule, then it is concluded that the test antibody and the reference antibody compete for binding to GDF8. As will be appreciated by a person of ordinary skill in the art, an antibody that competes for binding with a reference antibody may not necessarily bind to the same epitope as the reference antibody, but may sterically block binding of the reference antibody by binding an overlapping or adjacent epitope.

The invention provides human or humanized antibodies and antigen-binding fragments of human or humanized antibodies that specifically bind human growth and differentiation factor 8 (GDF8). These antibodies are characterized by binding to GDF8 with high affinity and by the ability to neutralize GDF8 activity. The antibodies can be full-length (for example, an IgG1 or IgG4 antibody) or may comprise only an antigen-binding portion (for example, a Fab, $F(ab')_2$ or scFv fragment), and may be modified to affect functionality, e.g., to eliminate residual effector functions (Reddy et al. (2000) J. Immunol. 164:1925-1933).

In one embodiment, the antibody of the invention comprises a heavy chain variable region (HCVR) amino acid sequence selected from the group consisting of SEQ ID NO: 2, SEQ ID NO: 18, SEQ ID NO: 34, SEQ ID NO: 50, SEQ ID NO: 66, SEQ ID NO: 82, SEQ ID NO: 98, SEQ ID NO: 114, SEQ ID NO: 130, SEQ ID NO: 146, SEQ ID NO: 162, SEQ ID NO: 178, SEQ ID NO: 194, SEQ ID NO: 210, SEQ ID NO: 226, SEQ ID NO: 242, SEQ ID NO: 258, SEQ ID NO: 274, SEQ ID NO: 290, SEQ ID NO: 306, SEQ ID NO: 360, and SEQ ID NO: 376, or a substantially identical sequence thereof.

In one embodiment, the antibody of the invention comprises a light chain variable region (LCVR) amino acid sequence selected from the group consisting of SEQ ID NO: 10, SEQ ID NO: 26, SEQ ID NO: 42, SEQ ID NO: 58, SEQ ID NO: 74, SEQ ID NO: 90, SEQ ID NO: 106, SEQ ID NO: 122, SEQ ID NO: 138, SEQ ID NO: 154, SEQ ID NO: 170, SEQ ID NO: 186, SEQ ID NO: 202, SEQ ID NO: 218, SEQ ID NO: 234, SEQ ID NO: 250, SEQ ID NO: 266, SEQ ID NO: 282, SEQ ID NO: 298, SEQ ID NO: 314, SEQ ID NO: 322, SEQ ID NO: 368, and SEQ ID NO: 384 or a substantially identical sequence thereof.

In one embodiment, the antibody of the invention comprises a HCVR amino acid sequence and a LCVR amino acid sequence, wherein the HCVR/LCVR pair sequences are selected from the group consisting of SEQ ID NO: 2/10, SEQ ID NO: 18/26, SEQ ID NO: 34/42, SEQ ID NO: 50/58, SEQ ID NO: 66/74, SEQ ID NO: 82/90, SEQ ID NO: 98/106, SEQ ID NO: 114/122, SEQ ID NO: 130/138, SEQ ID NO: 146/154, SEQ ID NO: 162/170, SEQ ID NO: 178/186, SEQ ID NO: 194/202, SEQ ID NO: 210/218, SEQ ID NO: 226/234, SEQ ID NO: 242/250, SEQ ID NO: 258/266, SEQ ID NO: 274/282, SEQ ID NO: 290/298, SEQ ID NO: 306/314, SEQ ID NO: 114/322, SEQ ID NO: 360/368, and SEQ ID NO: 376/384.

The invention also features a human or humanized antibody or antigen-binding fragment of an antibody comprising a heavy chain complementarity determining region 3 (HCDR3) amino acid sequence and a light chain CDR3 amino acid sequence (LCDR3), wherein the HCDR3 amino acid sequence is selected from the group consisting of SEQ ID NO: 8, SEQ ID NO: 24, SEQ ID NO: 40, SEQ ID NO: 56, SEQ ID NO: 72, SEQ ID NO: 88, SEQ ID NO: 104, SEQ ID NO: 120, SEQ ID NO: 136, SEQ ID NO: 152, SEQ ID NO: 168, SEQ ID NO: 184, SEQ ID NO: 200, SEQ ID NO: 216, SEQ ID NO: 232, SEQ ID NO: 248, SEQ ID NO: 264, SEQ ID NO: 280, SEQ ID NO: 296, SEQ ID NO: 312, SEQ ID NO: 366, and SEQ ID NO: 382, or a substantially identical sequence thereof, and the LCDR3 amino acid sequence is selected from the group consisting of SEQ ID NO:16, SEQ ID NO: 32, SEQ ID NO: 48, SEQ ID NO: 64, SEQ ID NO: 80, SEQ ID NO: 96, SEQ ID NO: 112, SEQ ID NO: 128, SEQ ID NO: 144, SEQ ID NO: 160, SEQ ID NO: 176, SEQ ID NO: 192, SEQ ID NO: 208, SEQ ID NO: 224, SEQ ID NO: 240, SEQ ID NO: 256, SEQ ID NO: 272, SEQ ID NO: 288, SEQ ID NO: 304, SEQ ID NO: 320, SEQ ID NO: 328, SEQ ID NO: 374, and SEQ ID NO: 390, or a substantially identical sequence thereof. In another embodiment, the antibody or fragment thereof comprises an HCDR3/LCDR3 amino acid sequence pair selected from the group consisting of SEQ ID NO: 8/16, SEQ ID NO: 24/32, SEQ ID NO: 40/48, SEQ ID NO: 56/64, SEQ ID NO: 72/80, SEQ ID NO: 88/96, SEQ ID NO: 104/112, SEQ ID NO: 120/128, SEQ ID NO: 136/144, SEQ ID NO: 152/160, SEQ ID NO: 168/176, SEQ ID NO: 184/192, SEQ ID NO: 200/208, SEQ ID NO: 216/224, SEQ ID NO: 232/240, SEQ ID NO: 248/256, SEQ ID NO: 264/272, SEQ ID NO: 280/288, SEQ ID NO: 296/304, SEQ ID NO: 312/320, SEQ ID NO: 120/328, SEQ ID NO: 366/374, and SEQ ID NO: 382/390.

In a related embodiment, the antibody or fragment thereof further comprises heavy chain CDR1 (HCDR1) and CDR2 (HCDR2) amino acid sequences and light chain CDR1 (LCDR1) and CDR2 (LCDR2) amino acid sequences, wherein the HCDR1 amino acid sequence is selected from the group consisting of SEQ ID NO: 4, SEQ ID NO: 20, SEQ ID NO: 36, SEQ ID NO: 52, SEQ ID NO: 68, SEQ ID NO: 84, SEQ ID NO: 100, SEQ ID NO: 116, SEQ ID NO: 132, SEQ ID NO: 148, SEQ ID NO: 164, SEQ ID NO: 180, SEQ ID NO: 196, SEQ ID NO: 212, SEQ ID NO: 228, SEQ ID NO: 244, SEQ ID NO: 260, SEQ ID NO: 276, SEQ ID NO: 292, SEQ ID NO: 308, SEQ ID NO: 362, and SEQ ID NO: 378, or a substantially identical sequence thereof; the HCDR2 amino acid sequence is selected from the group consisting of SEQ ID NO: 6, SEQ ID NO: 22, SEQ ID NO: 38, SEQ ID NO: 54, SEQ ID NO: 70, SEQ ID NO: 86, SEQ ID NO: 102, SEQ ID NO: 118, SEQ ID NO: 134, SEQ ID NO: 150, SEQ ID NO: 166, SEQ ID NO: 182, SEQ ID NO: 198, SEQ ID NO: 214, SEQ ID NO: 230, SEQ ID NO: 246, SEQ ID NO: 262, SEQ ID NO: 278, SEQ ID NO: 294, SEQ ID NO: 310, SEQ ID NO: 364, and SEQ ID NO: 380, or a substantially identical sequence thereof; the LCDR1 amino acid sequence is selected from the group consisting of SEQ ID NO: 12, SEQ ID NO: 28, SEQ ID NO: 44, SEQ ID NO: 60, SEQ ID NO: 76, SEQ ID NO: 92, SEQ ID NO: 108, SEQ ID NO: 124, SEQ ID NO: 140, SEQ ID NO: 156, SEQ ID NO: 172, SEQ ID NO: 188, SEQ ID NO: 204, SEQ ID NO: 220, SEQ ID NO: 236, SEQ ID NO: 252, SEQ ID NO: 268, SEQ ID NO: 284, SEQ ID NO: 300, SEQ ID NO: 316, SEQ ID NO: 324, SEQ ID NO: 370, and SEQ ID NO: 386 or a substantially identical sequence thereof; and the LCDR2 amino acid sequence is selected from the group consisting of SEQ ID NO: 14, SEQ ID NO: 30, SEQ ID NO: 46, SEQ ID NO: 62, SEQ ID NO: 78, SEQ ID NO: 94, SEQ ID NO: 110, SEQ ID NO: 126, SEQ ID NO: 142, SEQ ID NO: 158, SEQ ID NO: 174, SEQ ID NO: 190, SEQ ID NO: 206, SEQ ID NO: 222, SEQ ID NO: 238, SEQ ID NO: 254, SEQ ID NO: 270, SEQ ID NO: 286, SEQ ID NO: 302, SEQ ID NO: 318, SEQ ID NO: 326, SEQ ID NO: 372, and SEQ ID NO: 388 or a substantially identical sequence thereof. In another embodiment, the HCDR1, HCDR2 and HCDR3 are selected from the group consisting of SEQ ID NO: 36/38/40, SEQ ID NO: 116/118/120, SEQ ID NO: 228/230/232, SEQ ID NO: 362/364/366, and SEQ ID NO: 378/380/382; and LCDR1, LCDR2 and LCDR3 are selected from the group consisting of SEQ ID NO: 44/46/48, SEQ ID NO: 124/126/128, SEQ ID NO: 236/238/240, SEQ ID NO: 370/372/374, and SEQ ID NO: 386/388/390. In yet another embodiment, the heavy and light chain CDRs are selected from the group consisting of SEQ ID NO: 36/38/40/44/46/48 (e.g. 21-E5), SEQ ID NO: 116/118/120/124/126/128 (e.g. 8D12), SEQ ID NO: 228/230/232/236/238/240 (e.g. 1A2), SEQ ID NO: 362/364/366/370/372/374 (e.g. H4H1657N2), and SEQ ID NO: 378/380/382/386/388/390 (e.g. H4H1669P).

In a related embodiment, the invention includes an antibody or antigen-binding fragment of an antibody which specifically binds GDF8, wherein the antibody or fragment comprises the heavy and light chain CDR domains contained within heavy and light chain variable domain sequences selected from the group consisting of SEQ ID NO: 2/10, SEQ ID NO: 18/26, SEQ ID NO: 34/42, SEQ ID NO: 50/58, SEQ ID NO: 66/74, SEQ ID NO: 82/90, SEQ ID NO: 98/106, SEQ ID NO: 114/122, SEQ ID NO: 130/138, SEQ ID NO: 146/154, SEQ ID NO: 162/170, SEQ ID NO: 178/186, SEQ ID NO: 194/202, SEQ ID NO: 210/218, SEQ ID NO: 226/234, SEQ ID NO: 242/250, SEQ ID NO: 258/266, SEQ ID NO: 274/282, SEQ ID NO: 290/298, SEQ ID NO: 306/314, SEQ ID NO: 114/322, SEQ ID NO: 360/368, and SEQ ID NO: 376/384.

Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

The invention also provides nucleic acid molecules encoding the antibodies or antigen-binding fragments of the invention. Recombinant expression vectors carrying the antibody-encoding nucleic acids of the invention, and host cells into which such vectors have been introduced, are also encompassed by the invention, as are methods of making the antibodies of the invention by culturing the host cells of the invention.

In one embodiment, the antibody of the invention comprises CDRS contained within or a HCVR encoded by a nucleotide sequence selected from the group consisting of SEQ ID NO: 1, SEQ ID NO: 17, SEQ ID NO: 33, SEQ ID NO: 49, SEQ ID NO: 65, SEQ ID NO: 81, SEQ ID NO: 97, SEQ ID NO: 113, SEQ ID NO: 129, SEQ ID NO: 145, SEQ ID NO: 161, SEQ ID NO: 177, SEQ ID NO: 193, SEQ ID NO: 209, SEQ ID NO: 225, SEQ ID NO: 241, SEQ ID NO: 257, SEQ ID NO: 273, SEQ ID NO: 289, SEQ ID NO: 305, SEQ ID NO: 359, and SEQ ID NO: 375, or a substantially similar sequence having at least 95% homology thereof.

In one embodiment, the antibody of the invention comprises CDRS contained within or a LCVR encoded by a nucleotide sequence selected from the group consisting of SEQ ID NO: 9, SEQ ID NO: 25, SEQ ID NO: 41, SEQ ID NO: 57, SEQ ID NO: 73, SEQ ID NO: 89, SEQ ID NO: 105, SEQ ID NO: 121, SEQ ID NO: 137, SEQ ID NO: 153, SEQ ID NO: 169, SEQ ID NO: 185, SEQ ID NO: 201, SEQ ID NO: 217, SEQ ID NO: 233, SEQ ID NO: 249, SEQ ID NO: 265, SEQ ID NO: 281, SEQ ID NO: 297, SEQ ID NO: 313, SEQ ID NO: 321, SEQ ID NO: 367, and SEQ ID NO: 383 or a substantially similar sequence having at least 95% homology thereof.

The invention also features a fully human or humanized antibody or antibody fragment which binds GDF8 with an affinity (expressed as a dissociation constant, "$K_D$") of about 1 nM or less, as measured by surface plasmon resonance assay (for example, BIACORE™). In certain embodiments, the antibody of the invention exhibits a $K_D$ of about 700 pM or less; about 500 pM or less; about 320 pM or less; about 160 pM or less; about 100 pM or less; about 50 pM or less; about 10 pM or less; or about 5 pM or less.

In one embodiment, the invention provides a fully human or humanized monoclonal antibody (mAb) which specifically binds and inhibits human GDF8 and exhibits an $IC_{50}$ of less than or equal to about 10 nM; about 5 nM or less; about 3 nM or less; about 2 nM or less; about 1 nM or less; about 500 pM or less; or about 200 pM or less, as measured by GDF8 inducible luciferase assay. As shown in the experimental section below, some of the anti-GDF8 antibodies of the invention block the activity of closely related proteins, such as GDF11, with a much higher $IC_{50}$ than GDF8 in a luciferase bioassay. In one embodiment, the invention provides an antibody or antigen-binding fragment of an antibody that exhibits at least about 10-fold, at least about 50-fold, at least about 100-fold, at least about 200-fold, at least about 500-fold, at least about 1000-fold, or at least about 1500-fold higher $IC_{50}$ for blocking GDF11 activity relative to GDF8.

The invention encompasses anti-GDF8 antibodies having a modified glycosylation pattern. In some applications, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) JBC 277:26733). In other applications, modification of a galactosylation can be made in order to modify complement dependent cytotoxicity (CDC).

The invention includes anti-GDF8 antibodies which bind specific epitopes of GDF8 and are capable of blocking the biological activity of GDF8. In a first embodiment, the antibody of the invention binds an epitope of the mature GDF8 protein (SEQ ID NO:340) within amino acids from about 1 to about 109; from about 1 to about 54; from about 1 to about 44; from about 1 to about 34; from about 1 to about 24; and from about 1 to about 14. In a second embodiment, the antibody of the invention binds one or more of an epitope of the mature GDF8 protein (SEQ ID NO:340) within amino acids from about 35 to about 109; from about 45 to about 109; from about 55 to about 109; from about 65 to about 109; from about 75 to about 109; from about 85 to about 109; from about 92 to about 109; or from about 95 to about 109. In a third embodiment, the antibody or antigen-binding fragment of the antibody binds within an epitope of the mature human GDF8 protein from about amino acid residue 48 to about 72; from about 48 to about 69; from about 48 to about 65; from about 52 to about 72; from about 52 to about 65; or from about 56 to about 65.

According to certain embodiments of the invention, the anti-GDF8 antibodies bind to human GDF8 but not to GDF8 from other species. Alternatively, the anti-GDF8 antibodies of the invention, in certain embodiments, bind to human GDF8 and to GDF8 from one or more non-human species. For example, the anti-GDF8 antibodies of the invention may bind to human GDF8 and may bind or not bind, as the case may be, to one or more of mouse, rat, guinea pig, hamster, gerbil, pig, cat, dog, rabbit, goat, sheep, cow, horse, camel, cynomologous, marmoset, rhesus or chimpanzee GDF8.

The invention encompasses a human or humanized anti-GDF8 monoclonal antibody conjugated to a therapeutic moiety ("immunoconjugate"), such as a cytotoxin, a chemotherapeutic drug, an immunosuppressant or a radioisotope. Cytotoxin agents include any agent that is detrimental to cells. Examples of suitable cytotoxin agents and chemotherapeutic agents for forming immunoconjugates are known in the art, see for example, WO 05/103081, which is herein specifically incorporated by reference).

The antibodies of the invention may be monospecific, bi-specific, or multispecific. Multispecific antibodies may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244. The anti-GDF8 antibodies of the invention can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multispecific antibody with a second binding specificity. For example, the invention includes bi-specific antibodies wherein one arm of an immunoglobulin is specific for human GDF8 or a fragment thereof, and the other arm of the immunoglobulin is specific for a second therapeutic target or is conjugated to a therapeutic moiety.

An exemplary bi-specific antibody format that can be used in the context of the invention involves the use of a first immunoglobulin (Ig) CH3 domain and a second Ig CH3 domain, wherein the first and second Ig CH3 domains differ from one another by at least one amino acid, and wherein at least one amino acid difference reduces binding of the bispecific antibody to Protein A as compared to a bi-specific antibody lacking the amino acid difference. In one embodiment, the first Ig CH3 domain binds Protein A and the second Ig CH3 domain contains a mutation that reduces or abolishes Protein A binding such as an H95R modification (by IMGT exon numbering; H435R by EU numbering). The second CH3 may further comprise a Y96F modification (by IMGT; Y436F by EU). Further modifications that may be found within the second CH3 include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of the invention.

The anti-GDF8 antibodies and antibody fragments of the invention encompass proteins having amino acid sequences that vary from those of the described antibodies, but that retain the ability to bind human GDF8. Such variant antibodies and antibody fragments comprise one or more additions, deletions, or substitutions of amino acids when compared to parent sequence, but exhibit biological activity that is essentially equivalent to that of the described antibodies. Likewise, the anti-GDF8 antibody-encoding DNA sequences of the invention encompass sequences that comprise one or more additions, deletions, or substitutions of nucleotides when compared to the disclosed sequence, but that encode an anti-GDF8 antibody or antibody fragment that is essentially bioequivalent to an anti-GDF8 antibody or antibody fragment of the invention. Examples of such variant amino acid and DNA sequences are discussed above.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of anti-GDF8 antibodies of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include anti-GDF8 antibody variants comprising amino acid changes which modify the glycosylation characteristics of the antibodies, e.g., mutations which eliminate or remove glycosylation.

Therapeutic Administration and Formulations

The invention provides therapeutic compositions comprising the antibodies or antigen-binding fragments thereof of the invention. The administration of therapeutic compositions in accordance with the invention will be administered with suitable carriers, excipients, and other agents that are incorporated into formulations to provide improved transfer, delivery, tolerance, and the like.

A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the invention, provided that the active ingredient in the formulation is not inactivated by the formulation and the formulation is physiologically compatible and tolerable with the route of administration. See also Powell et al. "Compendium of excipients for parenteral formulations" PDA (1998) J Pharm Sci Technol 52:238-311.

The dose may vary depending upon the age and the size of a subject to be administered, target disease, conditions, route of administration, and the like. When the antibody of the invention is used for treating various conditions and diseases associated with GDF8, in an adult, it is advantageous to administer the antibody of the invention normally at a single dose of about 0.01 to about 20 mg/kg body weight, about 0.1 to about 10 mg/kg body weight, or about 0.1 to about 5 mg/kg body weight. Alternatively, the antibody or antigen binding fragment thereof can be administered to a healthy subject in combination with an exercise regimen. In embodiments, the healthy subject is experiencing age related loss of lean muscle mass and/or post-surgical muscle wasting. In embodiments, an effective amount for a subject is at least 400 mg, or about 36 mg/kg (assuming an average of 70 kg for an adult human).

Depending on the severity of the condition, the frequency and the duration of the treatment can be adjusted. In other parenteral administration and oral administration, the antibody can be administered in a dose corresponding to the dose given above. When the condition is especially severe, the dose may be increased according to the condition up to the amount that causes significant side effects, if any. In embodiments, the subject receives at least two doses or more subcutaneously. In embodiments, the subjects receive multiple doses intermittently, for example, once every week, once every two weeks, once every three weeks, once every four weeks, once every five weeks, and once every six weeks Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al. (1987) J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

The pharmaceutical composition can be also delivered in a vesicle, in particular a liposome (see Langer (1990) Science 249:1527-1533).

A pharmaceutical composition of the invention can be delivered subcutaneously or intravenously with a standard needle and syringe. In addition, with respect to subcutaneous delivery, a pen delivery device readily has applications in delivering a pharmaceutical composition of the invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUIIVIALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the invention include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L.P.), and the HUMIRA™ Pen (Abbott Labs, Abbott Park Ill.), to name only a few.

In certain situations, the pharmaceutical composition can be delivered in a controlled release system, for example, with the use of a pump or polymeric materials. In another embodiment, a controlled release system can be placed in proximity of the composition's target, thus requiring only a fraction of the systemic dose.

Examples of the composition for oral administration include solid or liquid dosage forms, specifically, tablets (including dragees and film-coated tablets), pills, granules, powdery preparations, capsules (including soft capsules), syrup, emulsions, suspensions, etc. Such a composition is manufactured by publicly known methods and contains a vehicle, a diluent or an excipient conventionally used in the field of pharmaceutical preparations. Examples of the vehicle or excipient for tablets are lactose, starch, sucrose, magnesium stearate, and the like.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to 500 mg per dosage form in a unit dose; especially in the form of injection, it is preferred that the aforesaid antibody is contained in about 5 to 500 mg and in about 10 to 400 mg for the other dosage forms.

Therapeutic Uses of the Antibodies

The antibodies of the invention are useful, inter alia, for increasing lean muscle mass in a subject. In some embodiments, a method of increasing lean muscle mass comprises providing an exercise regimen for the subject, and administering a composition comprising an effective amount of a GDF-8 inhibitor. In embodiments, the subject is a subject that has not been placed on exercise limitation by a physician and/or does not have a condition or disorder for which exercise is contraindicated. In embodiments, a subject has a loss of lean muscle mass. In other embodiments, the subject is at least 50 years, 55 years, or 60 years of age or older.

In embodiments, the antibodies of the invention are useful, inter alia, for the treatment, prevention and/or amelioration of any disease or disorder associated with GDF8 activity. More specifically, the antibodies of the invention are useful for the treatment of any condition or affliction which can be improved by increasing muscle strength/power and/or muscle mass and/or muscle function in an individual, or by favorably altering metabolism (carbohydrate, lipid and protein processing) by blocking GDF8 activity. Exemplary diseases, disorders and conditions that can be treated with the anti-GDF8 antibodies of the invention include, but are not limited to, sarcopenia, cachexia (either idiopathic or secondary to other conditions, e.g., cancer, chronic renal failure, or chronic obstructive pulmonary disease), muscle injury, muscle wasting and muscle atrophy, e.g., muscle atrophy or wasting caused by or associated with disuse, immobilization, bed rest, injury, medical treatment or surgical intervention (e.g., hip fracture, hip replacement, knee replacement, etc.) or by necessity of mechanical ventilation. Additional disorders that can be treated with the anti-GDF8 antibodies of the invention include, but are not limited to, sIBM (Sporadic Inclusion Body Myositis).

The invention includes therapeutic administration regimens which comprise administering an anti-GDF8 antibody of the invention in combination with at least one additional therapeutically active component. Non-limiting examples of such additional therapeutically active components include other GDF8 antagonists (e.g., small molecule inhibitors of GDF8 or other GDF8 antibodies or binding molecules), growth factor inhibitors, immunosuppressants, anti-inflammatory agents, metabolic inhibitors, enzyme inhibitors, and cytotoxic/cytostatic agents. The additional therapeutically active component(s) may be administered prior to, concurrent with, or after the administration of the anti-GDF8 antibody of the invention.

In a related embodiment, a method comprises combining administration of an antibody or antigen binding fragment thereof to a subject that is exercising on a regular basis, such as weight bearing exercises. In embodiments, a method comprises providing an exercise regimen, such as a regimen that promotes an increase in lean muscle mass. In embodiments, the exercise regimen includes one or more of resistance training, strength training, pilates, aerobic exercise, weight training, and yoga. In a specific embodiment, the exercise regimen includes resistance training and/or weight training. In embodiments, an exercise regimen is provided in writing and/or by illustration, on a computer readable medium, by video, or in an exercise facility.

In embodiments, resistance training includes training of any muscles of the body including without limitation, the muscles of a non-dominant hand, a dominant hand, a leg, an arm, a back, an abdominal muscle, a quadricep, a calf, a bicep, a tricep, a shoulder, a gluteus muscle, and/or a chest muscle. Resistance training can include the use of weights, a resistance band, exercise machines, and/or the subject's own body weight. Exercises can include chest press, leg press, arm curl, leg curl, hand grip, abdominal crunch, calf press, bicep curl, tricep curl, plank, side plank, and/or stair climb.

In embodiment, the exercise regimen provides for at least one set of exercises per muscle group and in specific embodiments, more than one, two or three sets of exercises. In embodiments, a set of exercises include at least eight repetitions or more.

A subject follows the provided exercise regimen at least once a week, twice a week, three times a week, four times a week, or five times a week. In embodiments, the exercise regimen is followed for at least 12 weeks.

In embodiments, a subject follows a set of exercises at a minimal level of intensity, for example, at 50% or less of the maximum weight that can be lifted for that exercise (1RM). In embodiments, the intensity is progressively increased during the exercise regimen. In embodiments, a 1-RM for each exercise (chest press, leg press, leg curl, and arm curl) can be measured at the exercise facility on the equipment used for exercise training at various time intervals such as baseline, week 4, and week 8. In embodiments, intensity is increased about 10% of the 1RM per week. In embodiments, intensity is at least 50%, and is maintained at about 65-90% of maximum.

In embodiments, a method further comprises monitoring the subjects resistance training comprising providing a device that measures training and/or providing a log book or computer program for tracking the repetitions, the duration, the intensity, and the frequency of the resistance training. In embodiments, a device includes an accelerometer, a dynamometer, a linear positioning device, and an actigraph.

In embodiments, a method comprises administering a GDF-8 inhibitor in an amount effective to increase lean muscle mass without resulting in adverse side effects on cardiac muscle and/or function. As discussed previously, GDF-8 inhibitors could be associated with cardiac hypertrophy. However, in embodiments, a dose and administration regimen is selected to minimize any effects on cardiac muscle and/or function. In embodiments, markers such as creatinine kinase, troponin, and the like are monitored during treatment. In embodiments, the treatment is discontinued if cardiac hypertrophy is observed, and/or if cardiac markers indicative of cardiac damage are elevated at least 20%.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Generation of Human Antibodies to Human GDF-8

Human anti-GDF8 antibodies were generated as described in U.S. Pat. No. 8,840,894. The exemplary GDF8 inhibitor used in the following Example is the human anti-GDF-8 antibody designated "H4H1657N2" (also referred to as REGN1033). H4H1657N2 has the following amino acid sequence characteristics: heavy chain variable region (HCVR) comprising SEQ ID NO:360; light chain variable domain (LCVR) comprising SEQ ID NO:368. The CDRs of REGN1033 comprise heavy chain complementarity determining region 1 (HCDR1) comprising SEQ ID NO:362; HCDR2 comprising SEQ ID NO:364; HCDR3 comprising SEQ ID NO:366; light chain complementarity determining region 1 (LCDR1) comprising SEQ ID NO:370; LCDR2 comprising SEQ ID NO:372; and LCDR3 comprising SEQ ID NO:374.

Example 2

Clinical Trial of Safety and Bioeffect of Anti-GDF-8 with and without Exercise

A randomized, double-blind, placebo-controlled, multicenter, parallel-group study of repeated doses of subcutaneous REGN1033 treatment effects on safety, body composition and muscle volume, muscle strength and stair climb function in 120 healthy male and female subjects with a sedentary lifestyle, who were 60 years of age and older was conducted. A 2×2 factorial design was used; up to 120 subjects (4 arms of 30 subjects each) were to be randomized in a 1:1:1:1 ratio to Placebo alone, REGN1033 (400 mg SC Q2W×6 doses) alone, Placebo+resistance exercise training (RT), or REGN1033+RT. Randomization was stratified by sex and by study site. The RT consisted of a center-based low intensity resistance exercise training at 50% of 1-repetition maximum (1-RM) twice a week for a total of 12 weeks with at least one progressive adjustment of exercise load during the study.

The primary objective of the study was to assess the effect of REGN1033, with and without exercise, on total lean body mass as measured by dual-energy x-ray absorptiometry (DEXA). Secondary objects include assessments of effects on safety and tolerability; effects on appendicular lean mass and fat mass by DEXA, effects on thigh muscle volume measured by MRI, upper and lower body strength by 1-repetition maximum methods, maximum hand grip strength, and stair climb power.

Patient Selection

The target population for this study 120 healthy male and female subjects with a sedentary lifestyle, who were 60 years of age and older.

The inclusion criteria were as follows: 1. Men and women aged 60 years and older, with no significant health issues or conditions; 2. Sexually active males willing to use contraceptives and not to donate sperm during the study and through 4 months after the study; 3. Females require clinical confirmation of postmenopausal status (at least 12 months since last menses, confirmed by postmenopausal levels of FSH>20 mIU/ml, or surgically sterile); 4. Body mass index (BMI) between 19 and 35 kg/m2 inclusive; 5. With no condition that could limit participation in supervised resistance training exercise based on the PAR-Q; 6. Sedentary lifestyle defined by a score of <125 on the CHAMPS-18 physical activity questionnaire in the last 3 months; 7. Willing to maintain current diet and adhere to exercise programs described for the study and to not start any new dieting/weight management programs; 8. Willing and able to return for all clinic visits and complete all study-related procedures; 9. Provide complete study-related questionnaires; and 10. Provide the informed consent form (ICF).

The exclusion criteria for the study include those subjects that have been hospitalized or had major surgery, have osteoarthritis, rheumatologic diseases or orthopedic disorders which limit joint range of motion or ability to exercise; have gastrointestinal disorders, chronic kidney disease, cancer, pulmonary disease, cardiac disease, asthma, stroke with residual paresis, paralysis, multiple sclerosis, Parkinson Disease, cognitive impairment, psychiatric conditions that warrant acute or chronic therapeutic intervention (eg, major depressive disorder, bipolar disorder, panic disorder, schizophrenia), current or previous use of any drugs known to influence muscle mass or performance within 6 months, and unable to undergo MM of the thighs Drug Administration REGN1033 was supplied as a lyophilized drug product and was administered subcutaneously in this study. Each vial of lyophilized REGN1033 was reconstituted under aseptic conditions to a final concentration of 100 mg/mL. Placebo matching REGN1033 is prepared in the same formulation as REGN1033 without the addition of REGN1033. The volume for placebo was the same at each dose level. Subjects received 400 mg REGN1033 or placebo (combined with resistance training RT for subjects in groups 3 and 4) every 2 weeks for a total of 6 doses SC in the abdomen. The specific abdominal quadrant was documented.

Study Design

This study had a screening period of 28 days (day −28 to day −1, screening/pretreatment), a drug treatment period (day 1 to day 71) and a 10 week follow up period after the last dose administration. Baseline measures for weight, strength measures and stair climb function, and echocardiography, were obtained during the screening period (day −14 to day −1). Baseline measures for DEXA and MM were obtained between day −7±3 and day −1. For all other parameters, baseline measures were obtained on day 1 (baseline). The total duration of the study from first dose administration was approximately 20 weeks.

Subjects were screened from day −28 to day −1 and eligible subjects were randomized to 1 of the 4 groups on day 1: Placebo; Placebo and RT; REGN1033; REGN1033 and RT. Subject eligibility was determined by standard screening procedures as well as screening for cognitive impairment using the Mini-Mental State Examination (MMSE) questionnaire, and screening for a sedentary lifestyle using the Community Health Activities Model Program for Seniors (CHAMPS) 18 physical activity questionnaire.

Within 2 weeks prior to the start of dosing (day −14 to day −1) all subjects were familiarized with the exercises and muscle strength and function measurements: leg press, chest press, leg curl, arm curl, handgrip strength, and unloaded and loaded stair climb (8-steps). Baseline upper and lower body strength (as determined by 1-repetition maximum [1-RM] for chest press and leg press), maximum handgrip strength, and unloaded and loaded stair climb power were determined for all subjects within 2 weeks (day −14 to day −1) prior to the start of dosing. For each strength/function measure, 2 tests were conducted for subjects in all 4 treatment groups in 2 separate visits within 2 weeks before administration of the first dose of study drug to accommodate familiarization with and learning of the testing procedures. The average value of these 2 measures during these 2 testing sessions will be used as the baseline value.

The 1-RM for each RT exercise (chest press, leg press, leg curl, and arm curl) was measured at the exercise facility on the equipment was used for exercise training at baseline, week 4, and week 8 and which was used to calculate the load for RT training during weeks 1 to 4, 5 to 8, and 9 to 12. Exercise training was conducted twice weekly for the 12 week treatment period. At least 1 day separated each exercise session. Within 10 days prior to the start of dosing (day −7±3 days) all subjects underwent whole body DEXA to determine total and regional fat mass and appendicular lean mass. Subjects also underwent Mill of both thighs to determine muscle volume and SC and intramuscular fat. The values obtained served as the baseline for these parameters.

On day 1, and every 2 weeks thereafter for a total of 6 times, subjects received SC doses of study drug (400 mg of REGN1033 or placebo) administered in the abdomen as 2 injections of 2 ml each injection site. Subjects were observed for 30 minutes for vital signs and collection of adverse events (AEs), including occurrence of injection site reactions. Accelerometry was used to monitor subject's physical activity during the study.

Subjects in groups 3 and 4 returned to the site for supervised low-intensity resistance training of the major muscle groups of the upper and lower extremities using resistance training equipment twice a week for 12 weeks. All training exercises were performed at a relatively low intensity of 50% of the 1-RM for each exercise.

All subjects completing the study returned for laboratory and safety assessments at weeks 2, 4, 6, 8 and 10 on days 15, 29, 43, 57, and 71 (all with a visit window of ±3 days) when subsequent doses of study drug were administered. Subjects were followed for 10 weeks after the last dose administration (day 71) and returned to the clinic for laboratory and safety assessments at weeks 12, 14, 16, and 20 (days 85±3, 99±3, 113±3, and 141±3 [until the end of the last study visit]). Efficacy measures (DEXA, MM, muscle strength and physical function) were obtained at screening and at week 12 (day 85±3). DEXA and muscle strength (double leg press, chest press, and maximum handgrip) and physical function (stair climb power) were determined at week 6 and week 20. Electrocardiograms were administered at day 1, week 4, week 8, week 12 and at the end of the study. Echocardiograms were conducted at week 12 (day 85±3 days).

All subjects were instructed to wear a GT3X Actigraph device (set at 30 Hz sampling rate) on the hip for the first 2 weeks on study from day 1 until the day 15 visit and another 14 day period between day 71 and day 85 (excluding the periods for center-resistance training exercise and during sleep). Subjects returned the device to the study site for downloading of data (day 15 and day 85). Time spent at various activity levels was determined based on activity threshold analysis using pre-defined cut-offs. Estimates of metabolic rates and energy expenditure were determined by predefined algorithms (Actigraph Corp).

Sample Analysis and Statistics

The primary efficacy variable, i.e. the percent change in Total Lean Mass by dual energy x-ray absorptiometry (DEXA) from baseline to week 12, was analyzed using a mixed-effect model repeated measure (MMRM) approach. Secondary efficacy variables were analyzed in a similar fashion. The model included factors (fixed effects) for treatment (with 4 levels of R1033+RT, R1033 without RT, Placebo+RT and Placebo without RT), baseline stratum (gender), visit, baseline value and treatment-by-visit interaction as covariates. The comparison of the primary endpoint between REGN1033 without RT and Placebo without RT was made. Same comparison was made between REGN1033 with RT and Placebo with RT. The exercise effect was also explored.

Results

Across all 4 treatment groups, 93.8-96.6% of randomized subjects completed their Week 12 visit. There was only one subject, in the Placebo alone treatment group, who discontinued the study due to an adverse event. The % of subjects in each of Placebo (PLC), Placebo+RT (PLC+RT), REGN1033(R1033), and REGN1033+RT (R1033+RT) groups that received all 6 doses of study drug was: 87.5%, 93.1%, 84.4%, and 90.6%, respectively. There was no imbalance across groups in compliance with either treatment or RT. The demographics were balanced among the 4 groups except the Placebo group had a higher percentage (18.8%) of black subjects; and the Placebo+RT group had higher percentage (75.9%) and the REGN1033 group had lower percentage (56.3%) of subjects' age greater than 65 years. The baseline values for DEXA, MRI, muscle strength and physical function for each group did not significantly differ from one another. (data not shown)

The primary objective of the study was to assess the effect of REGN1033, with and without exercise, on total lean body mass as measured by dual-energy x-ray absorptiometry (DEXA). Secondary objects include assessments of effects on safety and tolerability; effects on appendicular lean mass and fat mass by DEXA, effects on thigh muscle volume measured by MRI, upper and lower body strength by 1-repetition maximum methods, maximum hand grip strength, and stair climb power. In addition, potential metabolic effects of REGN1033 on HbA1C and HOMA-IR were examined.

The primary efficacy variable, i.e. the percent change in Total Lean Mass by dual energy x-ray absorptiometry (DEXA) from baseline to week 12, was analyzed using a mixed-effect model repeated measure (MMRM) approach. The model included factors (fixed effects) for treatment (with 4 levels of R1033+RT, R1033 without RT, Placebo+RT and Placebo without RT), baseline stratum (gender), visit, baseline value and treatment-by-visit interaction as covariates. The comparison of the primary endpoint between REGN1033 without RT and Placebo without RT was made. Same comparison was made between REGN1033 with RT and Placebo with RT. The exercise effect was also explored. Secondary Efficacy Endpoints with continuous outcome were analyzed by a similar method for primary efficacy endpoint.

The doses and dose regimens for this study were selected based on the results from other studies.

In a completed SAD study, 76 healthy volunteers received REGN1033 at doses up to 10 mg/kg intravenously (IV) and 400 mg SC. Among these, an elderly cohort of 8 healthy volunteers 65 to 85 years old received 6 mg/kg IV of study drug. All doses were well tolerated; no clinically significant safety signals were observed. (data not shown)

Another study was designed to assesses the safety, tolerability, pharmacokinetics (PK), immunogenicity, and pharmacodynamic (PD) effects of REGN1033 administered SC in healthy volunteers 60 years of age and older. A total of 5 cohorts with 12 subjects enrolled in each cohort were studied. Subjects received SC doses of REGN1033 (n=9) or placebo (n=3). The planned REGN1033 dose regimens were 100, 200, or 400 mg Q2W for a total of 6 doses per subject and 200 mg or 400 mg Q4W for a total of 3 doses per subject. The results from the study, shown in FIG. 1A, suggest that these doses of REGN1033 are well tolerated and are associated with an increase in lean mass detected by DEXA.

From these studies, PK and total GDF8 PD data suggest that REGN1033 may achieve concentrations associated with saturation of target engagement throughout the dose interval for the 400 mg Q4W and 400 mg Q2W dose levels. At the 100 mg Q4W dose level, there is expected to be REGN1033 exposures clearly less than those achieved at the higher doses. PK and PD data from phase 1 studies suggest that this lower dose will not achieve concentrations associated with engagement of the target across the entire dose interval in all individuals.

Figure 1B:
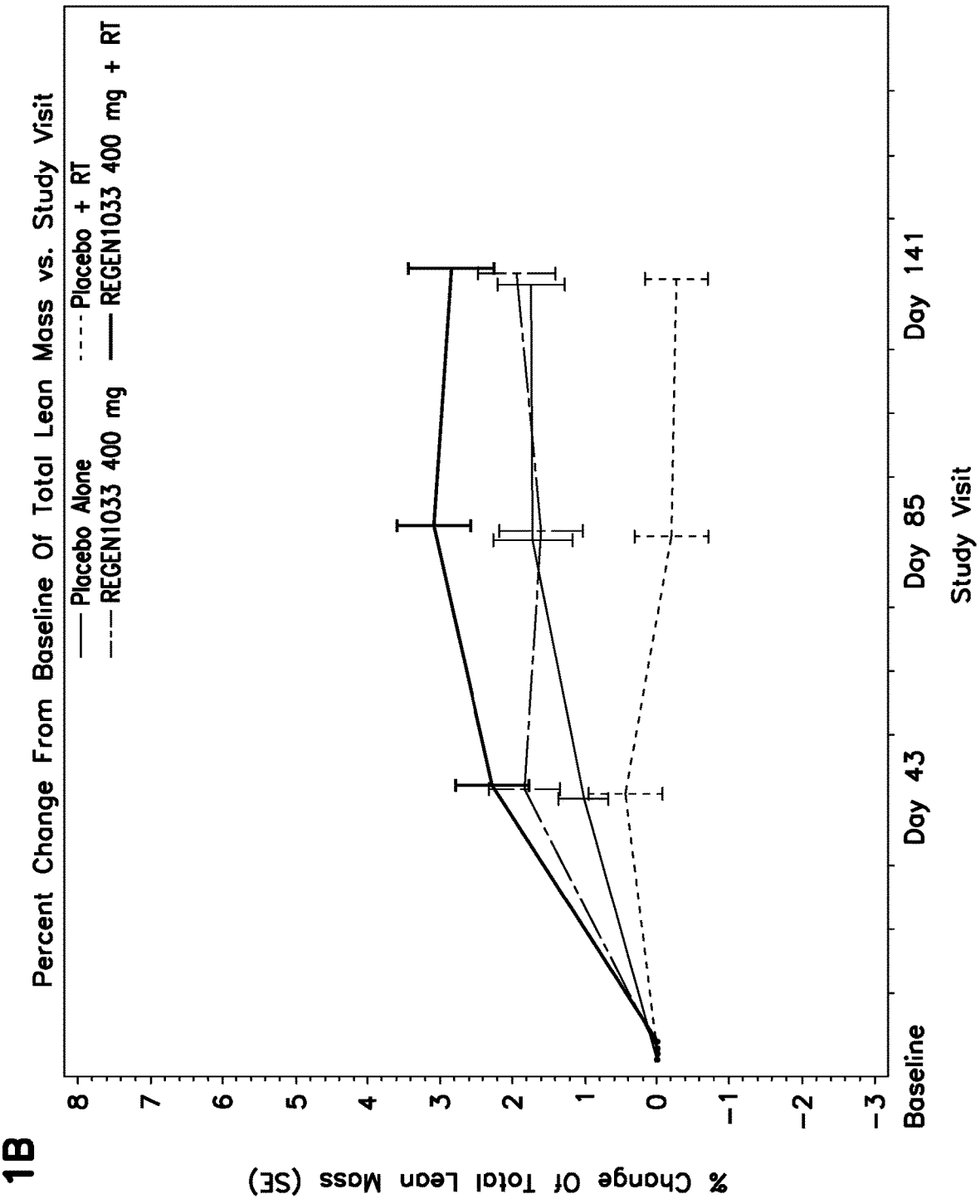

The results of the outcome of the primary efficacy variable are shown in Table 1 and FIG. 1B.

TABLE 1

| Summary of Primary Efficacy | Week 12 REGN alone vs. PBO alone | Week 12 REGN + RT vs. PBO + RT | Week 12 REGN combined vs. PBO combined | Week 12 PBO + RT vs. PBO | Week 12 REGN + RT vs. REGN | MMRM model REGN effect | MMRM model Exercise Effect | MMRM model REGN* Exercise Interaction |
|---|---|---|---|---|---|---|---|---|
| Percent change in total lean mass by dual energy x-ray absorptiometry (DXA) from baseline | 1.66% vs. 1.79% (p = 0.8640) | 3.10% vs. −0.25% (p < 0.0001) | 2.39% vs. 0.79% (p = 0.0048) | −0.25% vs. 1.79% (p = 0.0088) | 3.10% vs. 1.66% (p = 0.0609) | (p = 0.0008) | (p = 0.6333) | (p = 0.0124) |

Without exercise, REGN1033 (REGN) treatment did not increase total lean body mass measured by DEXA compared with Placebo (PBO) treatment (placebo adjusted change −0.13% p=0.8640, from baseline to week 12). With exercise, REGN1033 (REGN+RT) treatment significantly increased total lean body mass measured by DEXA from baseline to week 12 compared with Placebo (PBO+RT) treatment (placebo adjusted increase of 3.34%, p<0.0001). See Table 1 and FIG. 1B. The percent change in the 'Placebo+RT' group is significantly lower than in the 'Placebo alone' group: −0.25% vs. 1.79% (p=0.0088), but the 'REGN1033+RT' group is numerically higher than the 'REGN1033 alone' group: 3.10% vs. 1.66% (p=0.0609).

The factorial MMRM model also shows a significant REGN1033 treatment effect on percentage change of total lean body mass by DEXA from baseline to week 12 (P=0.0008) which is sustained at week 20 (P=0.0004). In addition, MMRM also shows an interaction effect (p=0.0124) between Exercise and Treatment.

Figure 2:
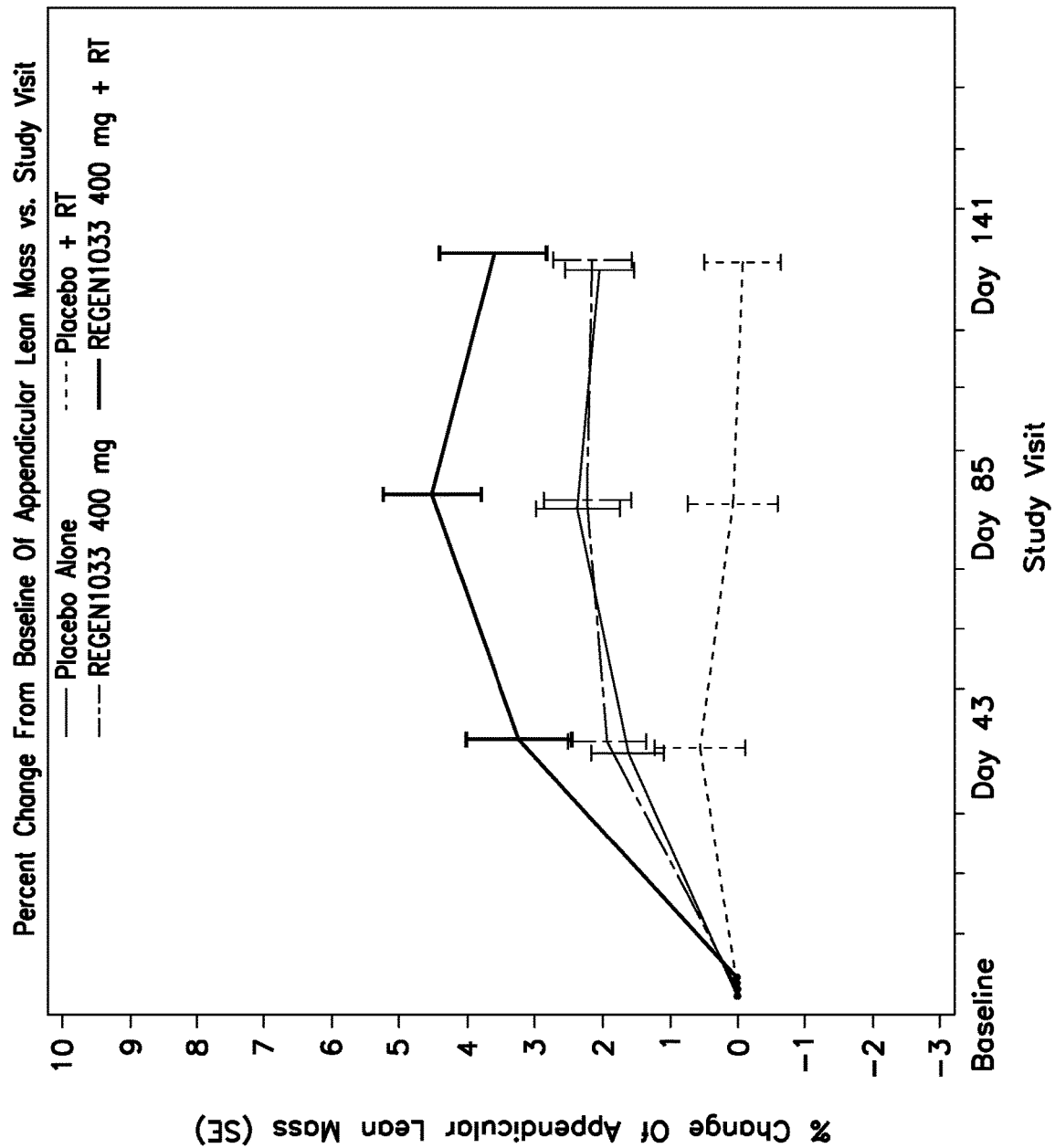
FIG. 2 shows the % change in appendicular fat mass per study visit for each group in subjects receiving Placebo alone (third line from top), Placebo plus resistance training (RT)(bottom line), 400 mg SC of REGN1033 alone (second line from top line), for a total of 6 doses over the study period, and 400 mg SC of REGN1033 plus RT (top line), for a total of 6 doses over the study period. Placebo alone and 400 mg SC of REGN1033 alone lines overlap one another.

In subjects randomized to receive progressive resistance training exercise, REGN1033(REGN+RT) treatment significantly increased the appendicular lean body mass measured by DEXA from baseline to week 12 compared with Placebo (PBO+RT) treatment (LS Mean difference vs Placebo 4.34%, P=0.001). As observed in the analysis of total lean body mass, the percent change in appendicular lean mass in the Placebo+RT group was significantly lower than in the Placebo alone group: 0.08% vs. 2.25% (p=0.0200), but the REGN1033+RT group was significantly higher than the REGN1033 alone group: 4.42% vs. 2.30% (p=0.0217). The factorial MMRM model also shows a significant treatment effect (0.0008) and interaction between treatment and exercise at week 12 (p=0.0040) which are sustained at week 20. See Table 2 and FIG. 2.

Figure 4:
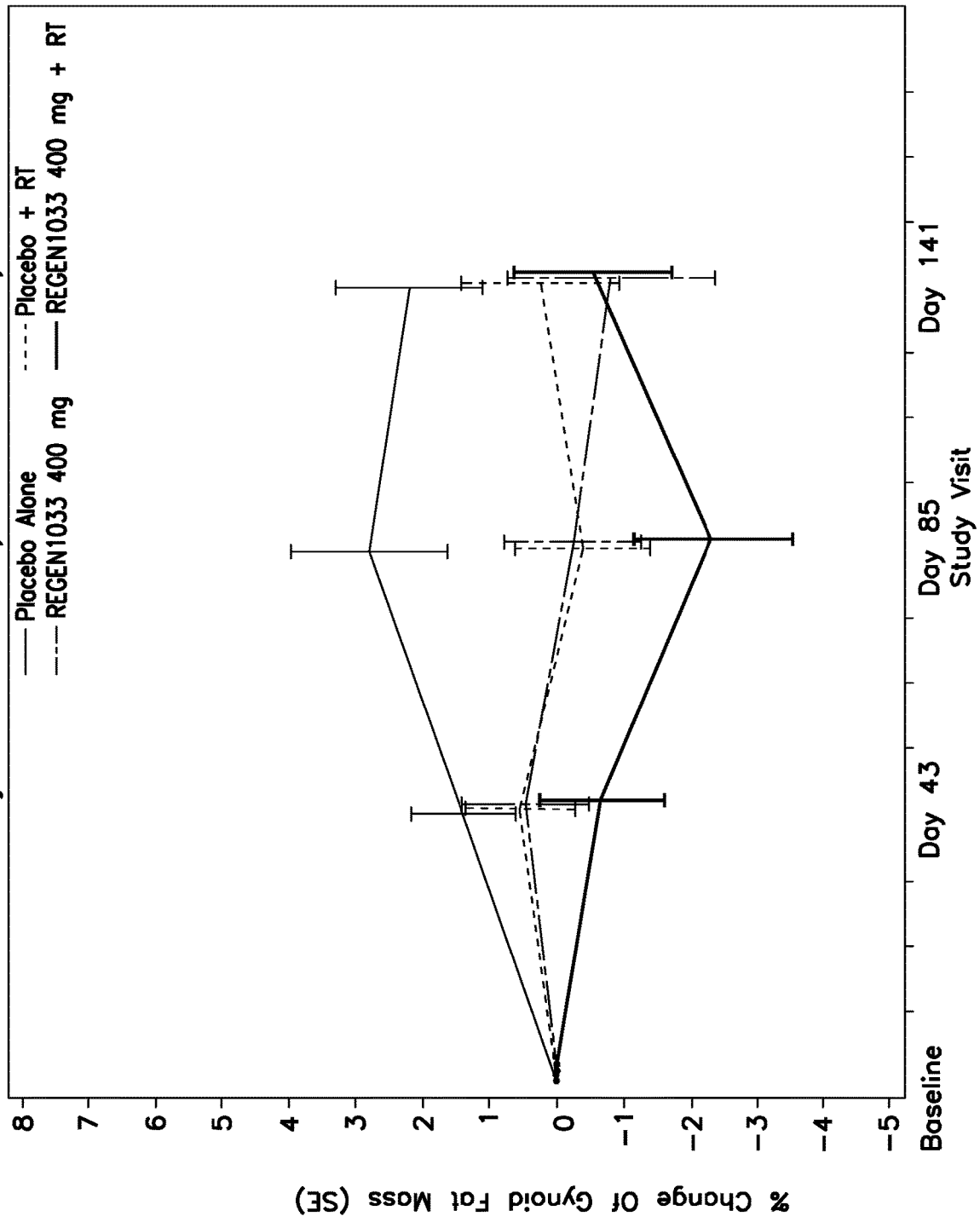
FIG. 4 shows percent change in gynoid fat per study visit per group in subjects receiving Placebo alone (top line), Placebo plus resistance training (RT)(second line from top), 400 mg SC of REGN1033 alone, for a total of 6 doses over the study period (third line from top), and 400 mg SC of REGN1033 plus RT, for a total of 6 doses over the study period (bottom line). Placebo plus RT and 400 mg SC of REGN1033 alone lines overlap one another.

REGN1033+RT group. At week 12, the LS Mean percentage (%) change from baseline in Placebo alone, Placebo+RT, REGN1033 alone, and REGN1033+RT groups are 2.42%, −0.49%, −0.27%, and −2.17% respectively. See FIG. 4. The factorial MMRM model shows trend significant treatment (p=0.0824) and exercise (0.0531) effects on gynoid fat mass but no interaction between Exercise and Treatment (p=0.8774).

Data from four muscle strength measures were also obtained. Equipment was standardized across all study sites for the chest press and leg press 1-RM measures and not for arm curl and leg curl measures. Furthermore, only a subset of subjects had arm curl and leg curl measures.

There was a trend of increase of leg press strength in all groups. At week 12, the LS Mean percentage (%) change from baseline in Placebo alone, Placebo+RT, REGN1033 alone, and REGN1033+RT groups are 4.7%, 8.9%, 6.7%,

TABLE 2

| | Week 12 REGN alone vs. PBO alone | Week 12 REGN + RT vs. PBO + RT | Week 12 REGN combined vs. PBO combined | Week 12 PBO + RT vs. PBO | Week 12 REGN + RT vs. REGN | MMRM model REGN effect | MMRM model Exercise Effect | MMRM model REGN* Exercise Interaction |
|---|---|---|---|---|---|---|---|---|
| Percent change in Appendicular lean mass (g) by DXA | 2.30% vs. 2.25% d = 0.04% (p = 0.9617) | 4.42% vs. 0.08% d = 4.34% (p < 0.0001) | 3.37% vs. 1.19% d = 2.18% (p = 0.0015). | 0.08% vs. 2.25% (p = 0.0200) | 4.42% vs. 2.30% (p = 0.0217) | (p = 0.0008) | (p = 0.9728) | (p = 0.0040) |

REGN1033 treatment, with or without exercise, resulted in statistically significant increases in MIII thigh muscle volume. See FIGS. 3A and 3B. The placebo adjusted effects on Mill thigh muscle volume (excluding intramuscular fat and vessels) at week 12 was +3.7%, p=0.0006 without exercise (REGN alone) and +4.5%, p<0.0001 with exercise (REGN+RT). There is a trend of increase of thigh muscle including intramuscular fat and vessels volume in the REGN1033 alone group compared to Placebo alone group and an increase of thigh muscle including intramuscular fat and vessels volume in the REGN1033+RT group as compared with Placebo+RT group. At week 12, the LS Mean percentage (%) change from baseline of thigh muscle including intramuscular fat and vessels volume (original scale) in Placebo alone, Placebo +RT, REGN1033 alone, and REGN1033+RT groups are −0.03%, −0.434%, 2.076%, and 3.405% respectively. In subjects randomized to not receive exercise, REGN1033 treatment significantly increased the thigh muscle including intramuscular fat and vessels volume measured by MM from baseline to week 12 compared with Placebo treatment (LS Mean difference vs Placebo 2.11%%, P=0.0139). In subjects randomized to receive progressive resistance training exercise, REGN1033 treatment significantly increased the thigh muscle including intramuscular fat and vessels volume measured by Mill from baseline to week 12 compared with Placebo treatment (LS Mean difference vs Placebo 3.84%, P<0.0001).

The factorial MMRM model also shows a significant treatment effect (<0.0001) but not exercise effect (p=0.4453). The interaction between treatment and exercise at week 12 is not significant (p=0.1651). There was an increase of lean body mass by DEXA measures in the placebo group which was not accompanied by an increase of muscle volume by MM measures. The reason for this discrepancy is unknown.

There is a trend of increase of Gynoid Fat Mass in the Placebo alone group at week 12 compared to other treatment groups and a decrease of Gynoid Fat Mass in the and 9.7% respectively. The factorial MMRM model did not show significant treatment effect (p=0.8389) but a borderline exercise effect (p=0.0541) on leg press. The interaction effect between Exercise and Treatment is not significant (p=0.8029).

There was a trend of increase of chest press strength in all groups. The REGN1033 alone group increased more as compared to Placebo alone group, and the REGN1033+RT group also increased more as compared to Placebo+RT. See FIG. 5. At week 12, the LS Mean percentage (%) change from baseline in Placebo alone, Placebo+RT, REGN1033 alone, and REGN1033+RT groups are 2.2%, 10.5%, 10.4%, and 15.3% respectively. In subjects randomized to not receive progressive resistance training exercise, REGN1033 treatment increased chess press strength from baseline to week 12 compared with Placebo treatment (LS Mean difference vs Placebo 8.2%, P=0.0524). In subjects randomized to receive progressive resistance training exercise, REGN1033 treatment numerically increased chest press from baseline to week 12 compared with Placebo treatment, but not significant (LS Mean difference vs Placebo 5.3%, P=0.2316). The factorial MMRM model showed a significant treatment effects (p=0.0525), and a statistically significant exercise effect (0.0272) on chest press and no interaction effect (p=0.5089) between Exercise and Treatment.

There was a trend of increase of leg curl strength in all groups up to week 12. At week 12, the LS Mean percentage (%) change from baseline in Placebo alone, Placebo+RT, REGN1033 alone, and REGN1033+RT groups were 5.3%, 16.3%, 10.4%, and 9.7% respectively. The change in leg curl strength REGN1033 alone was 5.1% higher than Placebo alone, however, REGN1033+RT was 6.6% lower than Placebo+RT. The percent change in the Placebo+RT group was significant higher than in the 'Placebo alone' group: 16.3% vs. 5.30% (p=0.0050), however the REGN1033+RT group was not higher than the REGN1033 alone group: 9.79% vs. 10.4% (p=0.8388). The factorial MMRM model did not show a significant interaction effect (p=0.0229) between Exercise and Treatment.

There was a trend of increase of arm curl in all groups. (data not shown). At week 12, the LS Mean percentage (%) change from baseline in Placebo alone, Placebo+RT, REGN1033 alone, and REGN1033+RT groups are 8.1%, 21.7%, 12.4%, and 15.7% respectively. In subjects randomized to not receive progressive resistance training exercise, REGN1033 treatment increased arm curl strength from baseline to week 12 compared with Placebo, but this difference was not statistically significant (LS Mean difference vs Placebo 4.3%, P=0.4589).

In subjects randomized to receive progressive resistance training exercise, REGN1033 treatment increased less in arm curl strength from baseline to week 12 compared with Placebo, but not significant (LS Mean difference vs Placebo −6.0%, P=0.3121). The factorial MMRM model showed no significant REGN1033 treatment effect (p=0.8958), a borderline exercise (p=0.053) effects, and no significant interaction effect (p=0.1318) between Exercise and Treatment.

There was a trend of increase of the dominate hand grip strength in REGN1033 groups. (data not shown). At week 12, the LS Mean percentage (%) change from baseline in Placebo alone, Placebo+RT, REGN1033 alone, and REGN1033+RT groups were 1.8%, 1.2%, 4.8%, and 5.0% respectively. In subjects randomized to not receive progressive resistance training exercise, REGN1033 treatment increased the dominate hand grip strength from baseline to week 12 compared with Placebo, but not significant (LS Mean difference vs Placebo 3.0%, P=0.4180). In subjects randomized to receive progressive resistance training exercise, REGN1033 treatment increased more in the dominate hand grip strength from baseline to week 12 compared with Placebo, but not significant (LS Mean difference vs Placebo 3.8%, P=0.3198). The factorial MMRM model shows a statistically significant REGN1033 treatment effect (p=0.0407), but no exercise effect (p=0.7033) or interaction between Exercise and Treatment (p=0.8283).

There was a trend of increase of the non-dominate hand grip strength in REGN1033 groups but not in Placebo groups. (data not shown). At week 12, the LS Mean percentage (%) change from baseline in Placebo alone, Placebo+RT, REGN1033 alone, and REGN1033+RT groups were 1.8%, −0.8%, 7.0%, and 4.2% respectively. In subjects randomized to not receive progressive resistance training exercise, REGN1033 treatment increased more in the non-dominate hand grip strength from baseline to week 12 compared with Placebo, but not significant (LS Mean difference vs Placebo 5.1%, P=0.1432). In subjects randomized to receive progressive resistance training exercise, REGN1033 treatment increased more in the non-dominate hand grip strength from baseline to week 12 compared with Placebo, but not significant (LS Mean difference vs Placebo 5.0%, P=0.1708). The factorial MMRM model showed a statistically significant REGN1033 treatment effect (p=0.0039) and a borderline significance exercise effect (p=0.0581) on the non-dominate hand grip strength. There was no interaction effect between Exercise and Treatment (p=0.6224).

There was a trend of increase of loaded stair climb power in all groups. (data not shown) At week 12, the LS Mean percentage (%) change from baseline in Placebo alone, Placebo+RT, REGN1033 alone, and REGN1033+RT groups were 5.6%, 12.9%, 12.2%, and 15.0% respectively. In subjects randomized to not receive progressive resistance training exercise, REGN1033 treatment increased more in the loaded stair climb power from baseline to week 12 compared with Placebo, but not significant (LS Mean difference vs Placebo 6.6%, P=0.1303). In subjects randomized to receive progressive resistance training exercise, REGN1033 treatment increased more in loaded stair climb power from baseline to week 12 compared with Placebo, but not significant (LS Mean difference vs Placebo 2.2%, P=0.6368). The factorial MMRM model did not show a statistically significant treatment effect (p=0.3612) or interaction between Exercise and Treatment (p=0.8043), but showed a statistically significant exercise effect (p=0.0151) in loaded stair climb.

There was a trend of increase of unloaded stair climb power in all groups. At week 12, the LS Mean percentage (%) change from baseline in Placebo alone, Placebo+RT, REGN1033 alone, and REGN1033+RT groups were 6.1%, 12.5%, 5.4%, and 9.8% respectively. There was not difference between REGN1033 and the Placebo groups. The factorial MMRM model did not show a statistically significant treatment effect (p=0.4670) or interaction between Treatment and Exercise (p=0.4180) but showed a statistically significance Exercise effect (p=0.0295). The percent change in the Placebo+RT group was higher than in the Placebo alone group 12.5% vs. 6.1% (p=0.0900), and the REGN1033+RT group is higher than 'REGN1033 alone' group: 9.8% vs. 5.4% (p=0.2253), however these differences are not statistically significant.

REGN1033 treatment and the resistance training (RT) exercises were generally well tolerated in the study. The results for Treatment Adverse Events (TEAS) are shown in Table 3.

TABLE 3

|  | Placebo | | REGN1033 400 mg + | |
| --- | --- | --- | --- | --- |
|  | Alone (N = 32) | RT (N = 29) | 400 mg (N = 32) | RT (N = 32) |
| Number of TEAEs | 151 | 103 | 129 | 98 |
| Number of serious TEAEs | 1 | 1 | 3 | 0 |
| Subjects with at least one TEAE | 26 (81.3%) | 27 (93.1%) | 27 (84.4%) | 28 (87.5%) |
| Subjects with at least one drug related TEAE | 10 (31.3%) | 6 (20.7%) | 14 (43.8%) | 10 (31.3%) |
| Subjects with at least one serious TEAE | 1 (3.1%) | 1 (3.4%) | 2 (6.3%) | 0 |
| Subjects with TEAEs resulting in discontinuation of study drug | 3 (9.4%) | 1 (3.4%) | 1 (3.1%) | 0 |
| Subjects with a TEAE resulting in death | 0 | 0 | 0 | 0 |

There were no deaths reported in this study and a total of 5 serious TEAS occurred in 4 subjects, including foot fracture in 1 subject in the Placebo Alone group; cholecystitis in 1 subject in the Placebo+RT group, stress cardiomyopathy in 1 subject in the REGN1033 group, and hypokalaemia and hypotension in 1 subject in the REGN1033 group. No serious TEAS were reported in the REGN1033+RT group. Subjects in Placebo Alone group reported more TEAEs and treatment-related TEAEs compared to other groups. The number and percentage of subjects experiencing at least one TEAE were similar across all treatment groups: 26 (81.3%) in placebo Alone, 27 (93.1%) in Placebo+RT, 27 (84.4%) in REGN1033, and 28 (87.5%) in REGN1033+RT group, respectively. A total of 5 subjects (3 and 1 in Placebo and Placebo+RT groups, compared to 1 and 0 subjects in REGN1033 and REGN1033+RT groups, respectively) discontinued drug treatment due to TEAEs.

Across the potentially clinically significant values (PCSV) categories of vital signs, ECG and hematology, there was no finding of an imbalance signaling higher frequency of PCSVs in the REGN1033 treatment groups. There were numerically more subjects with chemistry PCSVs in the REGN1033 Combined group than there were in the PLACEBO COMBINED group. Elevated Creatine Kinase values of >3×ULN occurred in 2 (6.3%). 1 (3.4%), 2 (6.3%) and 4 (12.5%) of subjects in the Placebo alone, Placebo+RT, REGN1033, and REGN1033+RT groups, respectively. There were no occurrence of Creatine Kinase values >10×ULN (Table 14.3.4.2.3). More subjects in the REGN1033 treated groups (7 [10.9%]) had a body weight increase >5% than in the Placebo groups (3, [4.9%], Table 14.3.5.1.2).

A review of echocardiogram parameters related to cardiac structure and function did not reveal any signal of cardiac hypertrophy or any other deleterious effects on cardiac function. REGN1033 treatment had no effect on left ventricular ejection fraction, LV wall thickness or interventricular septum thickness. There were no reported increases in LV mass or LV mass index in either the REGN1033 or the Placebo treatment groups. (data not shown)

Conclusions

With exercise, REGN1033 treatment significantly increased total lean body mass in healthy subjects measured by DEXA from baseline to week 12 compared with Placebo treatment (3.1% vs. −0.2%, <0.0001). Without exercise, REGN1033 treatment did not significantly increase total lean body mass measured by DEXA compared with Placebo treatment.

For secondary efficacy endpoints, the results of appendicular lean mass by DEXA are consistent with those observed in total lean body mass by DEXA. REGN1033 treatment, with or without exercise, resulted in statistically significant increases in MRI thigh muscle volume excluding intramuscular fat and vessels week 12 compared with Placebo treatment (placebo adjusted increase of 3.7%, P=0.0006 without exercise and 4.5%, P<0.0001 with exercise).

The resistance training (RT) exercises in this study were well tolerated in this elderly population. Significant exercise effects were shown by MMRM model in majority of the strength/function measures. This level of RT exercise did not result in significant increase of lean mass measured by DEXA or muscle volume measured by MRI. REGN1033 treatment also trended toward positive effects on several strength and functional endpoints examined in this study. Positive effects were seen in-chest press strength, handgrip strength, and loaded stair climb function.

Overall, REGN1033 SC 400 mg Q2W was generally well tolerated in this trial. The numbers of patients reporting TEAEs were comparable across treatment groups. A review of TEAEs did not reveal significant safety signal. Echocardiogram examinations did not reveal deleterious effects on cardiac structure or function.

Example 3

Clinical Trial Protocol of Anti-GDF-8 Treatment of Subjects with Sarcopenia with and without Exercise A randomized, double-blind, placebo-controlled, multi-center phase 2 study of the safety and efficacy of 3-month SC REGN1033 treatment in patients with sarcopenia was conducted. Two hundred fifty patients were enrolled, in 4 treatment groups. Eligible patients were males and females with sarcopenia and associated mobility impairment, 70 years of age and older, with an average age of 78 years old. Patients were randomized in a 1:1:1:1 ratio to receive placebo SC every 2 weeks (Q2W) for a total of 6 treatments, REGN1033 at 300 mg SC Q2W for a total of 6 treatments, REGN1033 at 300 mg SC every 4 weeks (Q4W) for a total of 3 treatments (with placebo on alternating weeks), and REGN1033 at 100 mg SC Q4W for a total of 3 treatments (with placebo on alternating weeks). The study had a screening/pretreatment period (day −28 to day −1), a 12-week treatment period (day 1 to day 85), and an 8-week follow-up period (through day 141).

Screening and Pretreatment Procedures (Day −28 to Day −1)

A sequential screening process took place across 3 visits, with initial eligibility determined at visit 1, and pretreatment procedures performed at visit 2 and visit 3. If feasible at the sites, visit 1 and visit 2 were conducted at the same time—if so, the visit 2 procedures were performed within 21 days of the first dose of study drug. Initial eligibility was determined at visit 1 by standard screening procedures, as well as 4-meter [4M] gait speed and the Mini-Mental State Examination (MMSE) score. Patients who met the initial eligibility criteria returned to the clinic at visit 2 and visit 3 for pretreatment baseline procedures and measurements.

The procedures included standard safety and laboratory assessments, DEXA scans, echocardiograms, strength measures (leg press, chest press, and handgrip strength), and function measures (stair climb, Short Physical Performance Battery [SPPB], 4M gait speed, and 6-Minute Walk Test [6MWT]).

Treatment Period and Study Drug Administration (Day 1 to Day 85)

Starting on day 1, patients were randomized to receive either REGN1033 or matching placebo. The doses were as follows:

300 mg SC Q2W for a total of 6 treatments
300 mg SC Q4W for a total of 3 treatments (with placebo on alternating weeks to maintain the blind)
100 mg SC Q4W for a total of 3 treatments (with placebo on alternating weeks to maintain the blind)
Matching placebo SC Q2W for a total of 6 treatments The injections were administered in the abdomen. Patients were observed for 30 minutes for vital signs and collection of adverse events (AEs), including occurrence of injection site reactions. Efficacy and safety procedures were performed, as well as patient-reported outcomes (PROs). Blood samples were collected for pharmacokinetics (PK), anti-drug antibodies (ADAs), and research. All blood samples were collected after an overnight fast and before dosing.

Follow-Up (Day 86 to Day 141)

Follow-up visits were on day 141, 8 weeks after the end of treatment visit on day 85.

Endpoints

The primary endpoint in the study was the percent change in total lean body mass measured by DEXA from baseline to week 12. The secondary endpoints were: TEAEs from baseline to the end of the study, changes from baseline in Appendicular lean mass by DEXA, maximal leg press strength, 1-repetition max (1-RM), maximal chest press strength (1-RM), 4M gait speed, SPPB and SPPB subscores, distance walked in the 6MWT, regional and total fat mass by DEXA, and hand grip strength by handheld dynamometer.

Procedures and Assessments

Safety and tolerability of REGN1033 were assessed by vital signs, electrocardiogram (ECG), echocardiogram, Adverse events (AEs), and clinical laboratory evaluations. Patients were asked to monitor and report all AEs experienced from the time the informed consent is signed until the end of study visit.

Efficacy was assessed by DEXA, strength measures (leg press, chest press, and handgrip strength), and function measures (stair climb, SPPB, 4Mgait speed, and 6MWT). Other measures used were accelerometry and PROs (the 10-item Physical Function Form [PF-10], the Functional Assessment of Chronic Illness Therapy[FACIT] Fatigue Scale, the Health Assessment Questionnaire Disability Index [HAQ-DI], the Mini-Nutritional Assessment short form [MNA-SF], and the Rapid Assessment of Physical Activity [RAPA] questionnaire).

Results

Ninety-five % of randomized patients completed the study. As shown below in Table 4, at each of the three dose regimens tested, REGN1033 treatment significantly increased total lean body mass from baseline to week 12 compared with placebo; mean differences from placebo were 1.7% (p=0.008), 1.8% (p=0.004) and 2.3% (p<0.001) for REGN1033 100 mg SC Q4W, 300 mg Q4W, and 300 mg Q2W respectively, corresponding to lean mass increases of 0.7, 0.8 and 1.0 kg. Appendicular lean mass also significantly increased in patients treated with REGN1033: placebo-adjusted changes ranged from 2.3-2.8%. DEXA-measured total fat mass, android fat mass, and gynoid fat mass all showed numerical decreases with REGN1033 treatment. REGN1033 treatment resulted in directionally greater mean changes from baseline in various measures of strength and function relative to placebo.

TABLE 4

| | REGN 100 mg Q4W (n = 62) vs. PBO (n = 65) | REGN 300 mg Q4W (n = 64) vs. PBO (n = 65) | REGN 300 mg Q2W (n = 59) vs. PBO (n = 65) |
|---|---|---|---|
| Primary Efficacy Endpoint: DEXA - Percent change from baseline to Week 12 | | | |
| Percent change in total lean mass by dual energy x-ray absorptiometry (DEXA) from baseline | 1.191% vs. −0.474%<br>d = 1.664% (p = 0.0077) | 1.308% vs. −0.474%<br>d = 1.781% (p = 0.0043) | 1.816% vs. −0.474%<br>d = 2.289% (p = 0.0004) |
| Summary of Secondary Efficacy: DEXA - Percent change from baseline to Week 12 | | | |
| Percent change in Appendicular lean mass (g) by DEXA | 2.162% vs. −0.249%<br>d = 2.412% (p = 0.0026) | 2.033% vs. −0.249%<br>d = 2.282% (p = 0.0043) | 2.502% vs. −0.249%<br>d = 2.751% (p = 0.0008) |
| Percent change in Total fat mass (g) determined by DEXA | −0.077% vs. −0.076%<br>d = −0.001% (p = 0.9993) | −2.666% vs. −0.076%<br>d = −2.590% (p = 0.0099) | −0.947% vs. −0.076%<br>d = −0.871% (p = 0.3945) |
| Percent change in Android fat mass (g) by DEXA | −0.496% vs. 2.501%<br>d = −2.998% (p = 0.0587) | −3.164% vs. 2.501%<br>d = −5.665% (p = 0.0004) | −2.209% vs. 2.501%<br>d = −4.710% (p = 0.0038) |
| Percent change from baseline in Gynoid fat mass (g) by DEXA | 0.022% vs. 0.156%<br>d = −0.135% (p = 0.9050) | −2.608% vs. 0.156%<br>d = −2.751% (p = 0.0152) | −2.185% vs. 0.156%<br>d = −2.341% (p = 0.0434) |

REGN1033 was generally safe and well tolerated. The frequency of adverse events was similar across treatment groups. The percentage of subjects experiencing at least one SAE was also similar across all treatment groups (7.7% in placebo group vs. 7.4% in REGN1033-treated groups). There was no discernable pattern to the distribution of SAEs. There were no clinically significant trends observed for laboratory tests, vital signs, ECGs and echocardiograms.

Conclusions

REGN1033 treatment significantly increased total lean and appendicular lean mass in patients with sarcopenia and was well tolerated.

The invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims. All publications referred to herein are hereby incorporated by reference.

What is claimed is:

1. A method for increasing lean body mass in a subject comprising:
   a. providing an exercise regimen for the subject, wherein the exercise regimen comprises resistance training; and
   b. administering a composition comprising an effective amount of a Growth and Differentiation Factor-8 (GDF-8) inhibitor to the subject, wherein the GDF-8 inhibitor is an antibody or antigen binding fragment thereof that specifically binds GDF-8, and comprises three heavy chain complementarity determining regions (HCDR1, HCDR2, HCDR3) contained within a heavy chain variable region (HCVR) comprising the amino acid sequence of SEQ ID NO: 360, and
   three light chain complementarity determining regions (LCDR1, LCDR2, LCDR3) contained within a light chain variable region (LCVR) comprising the amino acid sequence of SEQ ID NO:368,
   wherein the subject exhibits increased lean body mass compared to baseline value.

2. The method of claim 1, wherein the effective amount is at least 400 mg.

3. The method of claim 1, wherein the effective amount comprises a dosing regimen selected from a group consisting of at least 0.1 mg/kg to about 10 mg/kg, 1 mg/kg to about 10 mg/kg or 10 mg/kg to 100 mg/kg.

4. The method of claim 1, wherein the effective amount comprises a dosing regimen selected from a group consisting of a single dose of about 0.01 to about 20 mg/kg body weight, about 0.1 to about 10 mg/kg body weight, or about 0.1 to about 5 mg/kg body weight.

5. The method of claim 1, wherein the resistance training includes a set of exercises for training of a muscle selected from the group consisting of the dominant hand, non-dominant hand, leg, arm, chest and combinations thereof.

6. The method of claim 1, wherein the composition is administered at least once every four weeks, once every two weeks, once a week, twice a week, three times a week, four times a week, or five times a week.

7. The method of claim 1, wherein the composition is formulated for intravenous, subcutaneous, or oral administration.

8. The method of claim 7, wherein the composition is formulated for subcutaneous administration.

9. The method of claim 1, wherein the antibody or antigen binding fragment thereof comprises a HCVR amino acid sequence and a LCVR amino acid sequence, wherein the HCVR/LCVR sequence pair comprises the amino acid sequences of SEQ ID NO: 360/368.

10. The method of claim 1, wherein the antibody or antigen-binding fragment thereof comprises the HCDR3 amino acid sequence of SEQ ID NO: 366.

11. The method of claim 10, wherein the antibody or antigen-binding fragment thereof comprises the LCDR3 amino acid sequence of SEQ ID NO: 371.

12. The method of claim 10, wherein the antibody or antigen binding fragment thereof comprises the HCDR1 amino acid sequence of SEQ ID NO: 362.

13. The method of claim 12, wherein the antibody or antigen binding fragment thereof comprises the HCDR2 amino acid sequence of SEQ ID NO: 364.

14. The method of claim 11, wherein the antibody or antigen binding fragment thereof further comprises the LCDR1 amino acid sequence of SEQ ID NO: 370.

15. The method of claim 14, wherein the antibody or fragment thereof further comprises the LCDR2 amino acid sequence of SEQ ID NO: 372.

16. The method of claim 1, wherein the antibody or antigen binding fragment thereof comprises HCDR1, HCDR2 and HCDR3 amino acid sequences of SEQ ID NOs: 362/364/366 and LCDR1, LCDR2 and LCDR3 amino acid sequences of SEQ ID NOs: 370/372/374.

17. The method of claim 1, wherein the antibody or antigen binding fragment thereof comprises
three heavy chain CDRs (HCDR1, HCDR2, HCDR3) contained within the HCVR encoded by the nucleotide sequence of SEQ ID NO: 359, or a substantially similar sequence having at least 95% homology thereof, and
three light chain CDRs (LCDR1, LCDR2, LCDR3) contained within the LCVR encoded by the nucleotide sequence of SEQ ID NO: 367, or a substantially similar sequence having at least 95% homology thereof.

18. The method of claim 1, wherein the subject is experiencing age related loss of lean muscle mass and/or post-surgical muscle wasting.

19. The method of claim 1, wherein the subject is 60 years of age or older.

20. The method of claim 1, wherein the subject is a human subject.

21. The method of claim 1, wherein the antibody or antigen-binding fragment thereof specifically binds mature GDF8 protein comprising the amino acid sequence of SEQ ID NO: 340.

22. The method of claim 1, wherein the increase in lean body mass is determined by dual x-ray absorptiometry compared to baseline.

23. The method of claim 22, wherein the increase in lean body mass is an increase in total lean body mass determined by dual x-ray absorptiometry compared to baseline.

24. A method of treating a disease in a subject comprising
administering a composition comprising an effective amount of a Growth and Differentiation Factor-8 (GDF-8) inhibitor to the subject, wherein the GDF-8 inhibitor is an antibody or antigen binding fragment thereof that specifically binds GDF-8, and comprises
three heavy chain complementarity determining regions (HCDR1, HCDR2, HCDR3) contained within the heavy chain variable region (HCVR) comprising the amino acid sequence of SEQ ID NO: 360, and
three light chain complementarity determining regions (LCDR1, LCDR2, LCDR3) contained within a light chain variable region (LCVR) comprising the amino acid sequence of SEQ ID NO: 368; and
providing an exercise regimen for the subject, wherein the exercise regimen comprises resistance training, wherein the disease is selected from a group consisting of sarcopenia, cachexia, muscle injury, muscle wasting, muscle atrophy and Sporadic Inclusion Body Myositis (sIBM), and wherein the subject exhibits increased lean body mass compared to baseline value.

25. The method of claim 24, wherein the antibody or antigen binding fragment thereof comprises heavy and light chain variable domains (HCVR/LCVR) comprising amino acid sequences of SEQ ID NO: 360/368.

26. The method of claim 24, wherein the antibody or antigen binding fragment thereof comprises HCDR1, HCDR2 and HCDR3 amino acid sequences of SEQ ID NO: 362/364/366, respectively; and LCDR1, LCDR2 and LCDR3 amino acid sequences of SEQ ID NO: 370/372/374, respectively.

27. The method of claim 24, wherein the antibody or antigen-binding fragment thereof specifically binds mature GDF8 protein comprising the amino acid sequence of SEQ ID NO: 340.

28. The method of claim 24, wherein the increase in lean body mass is determined by dual x-ray absorptiometry compared to baseline.

29. The method of claim 28, wherein the increase in lean body mass is an increase in total lean body mass determined by dual x-ray absorptiometry compared to baseline.

* * * * *